United States Patent
Davis et al.

(10) Patent No.: US 11,998,616 B2
(45) Date of Patent: Jun. 4, 2024

(54) NANOPARTICLES FOR CROSSING THE BLOOD BRAIN BARRIER AND METHODS OF TREATMENT USING THE SAME

(71) Applicant: California Institute of Technology, Pasadena, CA (US)

(72) Inventors: Mark E. Davis, Pasadena, CA (US); Emily A. Wyent, Sherman Oaks, CA (US)

(73) Assignee: California Institute of Technology, Pasadena, CA (US)

( * ) Notice: Subject to any disclaimer, the term of this patent is extended or adjusted under 35 U.S.C. 154(b) by 219 days.

(21) Appl. No.: 17/215,443

(22) Filed: Mar. 29, 2021

(65) Prior Publication Data

US 2021/0220483 A1    Jul. 22, 2021

Related U.S. Application Data

(63) Continuation of application No. 16/438,762, filed on Jun. 12, 2019, now abandoned.

(60) Provisional application No. 62/684,593, filed on Jun. 13, 2018.

(51) Int. Cl.
| | |
|---|---|
| *A61K 47/69* | (2017.01) |
| *A61K 9/16* | (2006.01) |
| *A61K 31/137* | (2006.01) |
| *A61K 31/4045* | (2006.01) |
| *A61K 31/4745* | (2006.01) |

(Continued)

(52) U.S. Cl.
CPC ........ *A61K 47/6935* (2017.08); *A61K 9/1641* (2013.01); *A61K 31/137* (2013.01); *A61K 31/4045* (2013.01); *A61K 31/4745* (2013.01);

*C07K 16/32* (2013.01); *B82Y 5/00* (2013.01); *Y10S 977/773* (2013.01); *Y10S 977/906* (2013.01)

(58) Field of Classification Search
CPC .................................................. A61K 47/6935
See application file for complete search history.

(56) References Cited

U.S. PATENT DOCUMENTS

| | | |
|---|---|---|
| 4,631,190 A | 12/1986 | Shen et al. |
| 5,217,999 A | 6/1993 | Levitzki et al. |
| 5,302,606 A | 4/1994 | Spada et al. |
| | (Continued) | |

FOREIGN PATENT DOCUMENTS

| | | |
|---|---|---|
| CN | 102123698 A | 7/2011 |
| JP | 2000-514440 | 10/2000 |
| | (Continued) | |

OTHER PUBLICATIONS

Emily Ann Wyatt. "Targeted Nanoparticle Delivery of Therapeutics across the Blood-Brain and Blood-Tumor Barriers to Breast Cancer Brain Metastases." California Institute of Technology, PhD Thesis, 2018, pp. i-xxiii and 1-149. (Year: 2018).*

(Continued)

*Primary Examiner* — Isaac Shomer
(74) *Attorney, Agent, or Firm* — BakerHostetler

(57) ABSTRACT

The present application discloses nanoparticles carrying therapeutic agents, including chemotherapeutic agents, and targeting ligands suitable for delivering these therapeutic agents through the blood brain barrier and methods of using these patients on those patients in need of such treatment.

9 Claims, 14 Drawing Sheets

(51) Int. Cl.
*B82Y 5/00* (2011.01)
*C07K 16/32* (2006.01)

(56) References Cited

U.S. PATENT DOCUMENTS

| | | | |
|---|---|---|---|
| 5,330,992 | A | 7/1994 | Eissenstat et al. |
| 5,457,105 | A | 10/1995 | Barker |
| 5,578,325 | A | 11/1996 | Domb et al. |
| 5,596,878 | A | 1/1997 | Hanson et al. |
| 5,616,582 | A | 4/1997 | Barker |
| 5,693,631 | A | 12/1997 | Whittemore et al. |
| 5,710,173 | A | 1/1998 | Tang et al. |
| 5,747,498 | A | 5/1998 | Schnur et al. |
| 5,770,599 | A | 6/1998 | Gibson |
| 5,948,878 | A | 9/1999 | Burgess et al. |
| 5,972,707 | A | 10/1999 | Roy et al. |
| 6,007,845 | A | 12/1999 | Domb et al. |
| 6,034,081 | A | 3/2000 | Whittemore et al. |
| 6,048,736 | A | 4/2000 | Kosak |
| 6,060,466 | A | 5/2000 | Whittemore et al. |
| 6,225,346 | B1 | 5/2001 | Tang et al. |
| 6,391,874 | B1 | 5/2002 | Cockerill et al. |
| 6,596,878 | B2 | 7/2003 | Chen et al. |
| 6,645,944 | B2 | 11/2003 | Re et al. |
| 6,713,485 | B2 | 3/2004 | Carter et al. |
| 6,716,863 | B2 | 4/2004 | Tasaka et al. |
| 6,727,256 | B1 | 4/2004 | Carter et al. |
| 6,828,320 | B2 | 12/2004 | Cockerill et al. |
| 6,900,221 | B1 | 5/2005 | Norris et al. |
| 6,984,653 | B2 | 1/2006 | Tasaka et al. |
| 7,018,609 | B2 | 3/2006 | Hwang et al. |
| 7,087,613 | B2 | 8/2006 | Norris et al. |
| 7,091,192 | B1 | 8/2006 | Davis et al. |
| 7,094,427 | B2 | 8/2006 | Han et al. |
| 7,157,466 | B2 | 1/2007 | McClure et al. |
| 7,166,302 | B2 | 1/2007 | Hwang et al. |
| 7,270,808 | B2 | 9/2007 | Cheng et al. |
| 7,300,935 | B2 | 11/2007 | Cho et al. |
| 7,427,605 | B2 | 9/2008 | Davis et al. |
| RE41,065 | E | 12/2009 | Schnur et al. |
| 8,367,116 | B2 | 2/2013 | Pratt et al. |
| 8,367,166 | B2 | 2/2013 | Dahl et al. |
| 8,377,474 | B2 | 2/2013 | Hsu et al. |
| 8,557,292 | B2 | 10/2013 | Davis et al. |
| 8,746,999 | B2 | 6/2014 | Davis et al. |
| 8,758,810 | B2 | 6/2014 | Okada et al. |
| 8,968,714 | B2 | 3/2015 | Davis et al. |
| 9,132,097 | B2 | 9/2015 | Davis et al. |
| 9,186,327 | B2 | 11/2015 | Davis et al. |
| 9,334,367 | B2 | 5/2016 | Davis et al. |
| 9,446,149 | B2 | 9/2016 | Davis et al. |
| 9,468,681 | B2 | 10/2016 | Davis et al. |
| 9,610,355 | B2 | 4/2017 | Davis et al. |
| 9,913,911 | B2 | 3/2018 | Davis et al. |
| 10,155,051 | B2 | 12/2018 | Davis et al. |
| 10,166,291 | B2 | 1/2019 | Davis et al. |
| 10,287,401 | B2 | 5/2019 | Davis et al. |
| 10,717,825 | B2 | 7/2020 | Davis et al. |
| 11,738,092 | B2 * | 8/2023 | Wyent .................. A61K 47/549 536/53 |
| 2002/0054902 | A1 | 5/2002 | Pardridge |
| 2002/0061288 | A1 | 5/2002 | Hubbell et al. |
| 2003/0055212 | A1 | 3/2003 | Freund et al. |
| 2003/0059399 | A1 | 3/2003 | Holmes-Farley et al. |
| 2003/0147966 | A1 | 8/2003 | Franzen et al. |
| 2004/0023334 | A1 | 2/2004 | Prior |
| 2004/0126838 | A1 | 7/2004 | Defrees et al. |
| 2004/0220146 | A1 | 11/2004 | Freeman et al. |
| 2005/0090732 | A1 | 4/2005 | Ivkov et al. |
| 2005/0148607 | A1 | 7/2005 | Suzuki et al. |
| 2006/0055069 | A1 | 3/2006 | DiMatteo et al. |
| 2006/0078997 | A1 | 4/2006 | Lugade et al. |
| 2006/0134062 | A1 | 6/2006 | Huval et al. |
| 2006/0153907 | A1 | 7/2006 | Zalipsky et al. |
| 2006/0159736 | A1 | 7/2006 | Zalipsky et al. |
| 2006/0246524 | A1 | 11/2006 | Bauer et al. |
| 2006/0263435 | A1 | 11/2006 | Davis et al. |
| 2008/0099172 | A1 | 5/2008 | Pelton et al. |
| 2008/0214584 | A1 | 9/2008 | Ohta et al. |
| 2009/0169638 | A1 | 7/2009 | Davis et al. |
| 2009/0281024 | A1 | 11/2009 | Zankel et al. |
| 2010/0029545 | A1 | 2/2010 | Sumerlin et al. |
| 2010/0040556 | A1 | 2/2010 | Davis et al. |
| 2010/0069500 | A1 | 3/2010 | Dhal et al. |
| 2010/0166865 | A1 | 7/2010 | Kumar et al. |
| 2010/0303850 | A1 | 12/2010 | Lipford et al. |
| 2010/0309691 | A1 | 12/2010 | Baptiste et al. |
| 2010/0330686 | A1 | 12/2010 | Park |
| 2011/0086431 | A1 | 4/2011 | Lugade et al. |
| 2012/0225129 | A1 | 9/2012 | Eliasof et al. |
| 2012/0259021 | A1 | 10/2012 | Jiang et al. |
| 2012/0309691 | A1 | 12/2012 | Zhou et al. |
| 2012/0328564 | A1 | 12/2012 | Govindan et al. |
| 2014/0249202 | A1 | 9/2014 | Davis et al. |
| 2014/0249203 | A1 | 9/2014 | Davis et al. |
| 2014/0348754 | A1 | 11/2014 | Wiley et al. |
| 2015/0045419 | A1 | 2/2015 | Lam et al. |
| 2015/0376237 | A1 | 12/2015 | Borros et al. |
| 2016/0000934 | A1 | 1/2016 | Davis et al. |
| 2017/0071857 | A1 | 3/2017 | Wiley et al. |

FOREIGN PATENT DOCUMENTS

| | | | |
|---|---|---|---|
| JP | 2004-525858 | A | 11/2001 |
| JP | 2005-511761 | | 4/2005 |
| JP | 2005-119255 | | 5/2005 |
| JP | 2008-512640 | | 4/2008 |
| JP | 2008-516240 | A | 5/2008 |
| JP | 2010-501004 | A | 5/2008 |
| JP | 2009-508494 | | 3/2009 |
| JP | 2012-500208 | A | 1/2012 |
| JP | 2014-514431 | | 6/2014 |
| WO | 91/15495 | A1 | 10/1991 |
| WO | 92/20642 | A1 | 11/1992 |
| WO | 92/21660 | A1 | 12/1992 |
| WO | 94/03427 | A1 | 2/1994 |
| WO | 94/14808 | A1 | 7/1994 |
| WO | 96/00226 | A1 | 1/1996 |
| WO | 97/13771 | A1 | 4/1997 |
| WO | 97/47658 | A1 | 12/1997 |
| WO | 98/02437 | A1 | 1/1998 |
| WO | 99/10022 | A2 | 3/1999 |
| WO | 00/10007 | A2 | 2/2000 |
| WO | 00/44728 | A1 | 8/2000 |
| WO | 01/01921 | A1 | 1/2001 |
| WO | 01/77107 | A1 | 10/2001 |
| WO | 01/82900 | A1 | 11/2001 |
| WO | 01/98277 | A2 | 12/2001 |
| WO | 01/98299 | A1 | 12/2001 |
| WO | 02/02552 | A1 | 1/2002 |
| WO | 03/00688 | A1 | 1/2003 |
| WO | 03/31442 | A1 | 4/2003 |
| WO | 03/49740 | A1 | 6/2003 |
| WO | 03/50108 | A1 | 6/2003 |
| WO | 03/53446 | A1 | 7/2003 |
| WO | 2005/074887 | A2 | 8/2005 |
| WO | 2005/119255 | A2 | 12/2005 |
| WO | 2007/034479 | A2 | 3/2007 |
| WO | 2007/061919 | A2 | 5/2007 |
| WO | 2008/011561 | A2 | 1/2008 |
| WO | 2008/060734 | A2 | 5/2008 |
| WO | 2009/036022 | A1 | 3/2009 |
| WO | 2010/019718 | A2 | 2/2010 |
| WO | 2010/120262 | A1 | 10/2010 |
| WO | 2011/072133 | A1 | 6/2011 |
| WO | 2011/159161 | A2 | 12/2011 |
| WO | 2012/079047 | A2 | 6/2012 |
| WO | 2012/158622 | A2 | 11/2012 |
| WO | 2014/033549 | A2 | 3/2014 |
| WO | 2014/133547 | A1 | 9/2014 |
| WO | 2014/133549 | A1 | 9/2014 |
| WO | 2014/185964 | A1 | 11/2014 |

(56) References Cited

FOREIGN PATENT DOCUMENTS

| WO | 2016/037166 A1 | 3/2016 |
|---|---|---|
| WO | 2017/003668 A1 | 1/2017 |
| WO | 2020/173668 A1 | 9/2020 |

OTHER PUBLICATIONS

California Institute of Technology, https://thesis.library.caltech.edu/11033/ accessed Jun. 28, 2023, 2 printed pages. (Year: 2023).*
Andrew James Clark. "Delivery of Targeted Nanoparticles Across the Blood-Brain Barrier Using a Detachable Targeting Ligand." California Institute of Technology, PhD Thesis, 2016, pp. i-xxiii and 1-177. (Year: 2016).*
Han Han and Mark E. Davis. "Single-Antibody, Targeted Nanoparticle Delivery of Camptothecin." Molecular Pharmaceutics, vol. 10, 2013, pp. 2558-2567. (Year: 2013).*
Han Han. "Development of Targeted, Polymeric Delivery Vehicles for Camptothecin and siRNA via Boronic Acid-Diol Complexation." California Institute of Technology, PhD Thesis, 2013, pp. i-xv and 1-160. (Year: 2013).*
Emily Wyent (Wyatt)—LinkedIn. https://www.linkedin.com/in/emily-ann-wyent accessed Oct. 30, 2023, pp. 1-10. (Year: 2023).*
U.S. Appl. No. 16/438,762, filed Jun. 12, 2019.
Zhong et al. "Low molecular weight linear polyethyleneimine-b-poly(ethylene glycol)-b-polyethyleneimine triblock copolymers: Synthesis, characterization, and in vitro gene transfer properties", Biomacromolecules, 2005, 6, 3440-3448.
Zhou et al: Highly penetrative, drug-loaded nanocarriers improve treatment of glioblastoma. PNAS Early Edition, 2013, 1-6.
Zhu et al. "Amphiphilic cationic [dendritic poly(L-lysine)]-block-poly(L-lactide)-block-[dendritic poly(L-lysine)]s in aqueous solution: Self-aggregation and interaction with DNA as gene delivery carries", Macromol. Biosci., 2011, 11, 174-186.
Zuckerman et al., "Correlating animal and human phase Ia/Ib clinical data with CALAA-01, a targeted, polymer-based nanoparticle containing siRNA", Proc. Natl. Acad. Sci. USA, 2014, 111, 11449-11454.
Organ Biology, 2017, vol. 24(1), pp. 54-60 [English abstract included].
Adeli et al. "Tumor-targeted drug delivery systems based on supramolecular interactions between iron oxide-carbon nanotubes PAMAM-PEG-PAMAM linear-dendritic copolymers", J. Iran. Chem. Soc., 2013, 10, 701-708.
Adkins et al., "NKTR-102 efficacy versus irinotecan in a mouse model of brain metastases of breast cancer", BMC Cancer, 2015, 15, 685.
Allen, T.M. Ligand-Targeted Therapeutics in Anticancer Therapy. Nature Reviews, vol. 2, pp. 750-763, Oct. 2002.
Armstrong et al., "The Hydrodynamic Radii of Macromolecules and Their Effect on Red Blood Cell Aggregation", Biophysical Journal, 2004, 87(6), 4259-4270.
Aversa et al., "Metastatic breast cancer subtypes and central nervous system metastases", Breast, 2014, 23, 623-628.
Ballarin-Gonzalez et al. "Polycation-based nanoparticle delivery of RNAi therapeutics: Adverse effects and solutions", Advanced Drug Delivery Reviews, 2012, 64, 1717-1729.
Bao et al., "0X26 modified hyperbranched polyglycerol-conjugated poly(lactic-co-glycolic acid) nanoparticles: Synthesis, characterization and evaluation of its brain delivery ability", Journal of Materials Science: Materials in Medicine, May 9, 2012, vol. 23, No. 8, 1891-1901.
Barnholtz-Sloan et al., "Incidence Proportions of Bain Metastases in patients diagnosed (1973 to 2001) in the Metropolitan Detroit Center Surveillance System", J. Clin. Oncol., 2004, 22, 2865-2872.
Barros et al., "Safety profile of RNAi nanomedicines", Advanced Drug Delivery Reviews, 2012,64, 1730-1737.
Bartlett et al., "Physicochemical and Biological Characterization of Targeted, Nucleic Acid- Containing Nanoparticles", Bioconjugate Chemistry, 2007, 18, 456-468.

Bartlett, D.W. et al., "Impact of tumor-specific targeting on the biodistribution and efficacy of siRNA nanoparticles measured by multimodality in vivo imaging", PNAS, 2007, pp. 15549-15554.
Bellocq et al., "Transferrin-Containing Cyclodextrin Polymer-Based Particles For Tumor-Targeted Gene Delivery", Bioconjug Chem, 2003, 14, 1122-1132.
Bohn et al., "Semi-automated rapid quantification of brain vessel density using fluorescent microscopy", J. Neurosci. Methods, 2016, 270, 124-131.
Brissault et al., "Synthesis of polypropylene glycol)-block-polyethylenimine tri block copolymers for the delivery of nucleic acids", Macromol. Biosci., 2012, 11, 652-661.
Chang et al., "Characterization of endocytosis of transferrin-coated PLGA nano particles by the blood-brain barrier", International Journal of Pharmaceutics, Sep. 11, 2009, vol. 379, No. 2, 285-292.
Chen et al., "Modern Methods for delivery of drugs across the blood-brain barrier", Adv. Drug Deliv. Rev., 2012, 64, 640-665.
Chen et al., Acute Toxicological Effects of Copper Nanoparticles In Vivo", Toxicol. Letters, 2006, 163, 109-120."
Choi et al., "Mechanism of active targeting in solid tumors with transferrin-containing gold nanoparticles", PNAS, Jan. 2010, 107(3), 1235-1240.
Choi et al., Renal Clearance of Quantum Dots", Nat. Biotechnol., Sep. 2007, 25, 1165-1170."
Choi et al., Targeting Kidney Mesangium by Nanoparticles of Defined Size", P Natl Acad Sci, 2001, 108,6656-6661."
Choi et al., Tissue and Organ Selective Biodistribution of Nir Fluorescent Quantum Dots", Nano Letters, May 2009, 9, 2354-2359."
Christie et al., "Targeted polymeric micelles for siRNA treatment of experimental cancer by intravenous injection", ACS Nano., 2012, 6, 5174-5189.
Clark et al., "Increased brain uptake of targeted nanoparticles by adding an acid-cleavable linkage between transferrin and the nanoparticle core", Proc. Natl. Acad. Sci. USA, 2015, 112, 12486-12491.
Clark, Andrew James, "Delivery of Targeted Nanoparticles Across the Blood-Brain Barrier Using a Detachable Targeting Ligand." California Institute of Technology, PhD Thesis, 2016, pp. i-xxiii and 1-177 (200 total sheets). (Year: 2016).
Coderre et al., "The Radiation Biology of Boron Neutron Capture Therapy", Radiat Res, 1999, 151, 1-18.
D'Addio et al., "Effects of block copolymer properties on nanocarrier protection from in vivo clearance", Journal of Controlled Release, 2012, 162, 208-217.
Dautry-Varsat et al., "pH and the Recycling of Transferrin During Receptor-Mediated Endocytosis", P Natl Acad Sci, 1983, 80, 2258-2262.
Davis et al., "Evidence of RNAi in Humans from Systemically Administered siRNA Via Targeted Nanoparticles", Nature, 2010, 464, 1067-1070.
Davis et al., "Nanoparticle therapeutics: An emerging treatment modality for cancer", Nat. Rev. Drug Discov., Sep. 2008, 7, 771-782.
Davis et al., "The First Targeted Delivery of siRNA in Humans Via a Self-Assembling, Cyclodextrin Polymer-Based Nanoparticle: From Concept to Clinic", Molecular Pharmaceutics, 2009, 6, 659-668.
Duncan, R. Polymer conjugates as anticancer nanomedicines. Nature Reviews, vol. 6, pp. 688-701, Sep. 2006.
Friden et al., "Characterization, Receptor Mapping and Blood-Brain Barrier Transcytosis of Antibodies to the Human Transferrin Receptor", J Pharm Exp Ther, 1996, 278, 1491-1498.
Fujita, N. et al., Boronic Acids in Molecular Self-Assembly, Chem. Asian J., 2008, vol. 3, pp. 1076-1091.
Gallas et al., "Chemistry and formulations for siRNA therapeutics", Chem. Soc. Rev., 2012, 42, 7983-7997.
Georgieva et al., "Smuggling Drugs into the Brain: An Overview of Ligands Targeting Transcytosis for Drug Delivery Across the Blood Brain Barrier", Pharmaceutics, 2014, 6(4), 557-583.
Goldman, C.K. et al., "In Vitro And In Vivo Gene Delivery Mediated By A Synthetic Polycationic Amino Polymer", Nature, Biotechnology, May 1997, 15, 462-466.

(56) References Cited

OTHER PUBLICATIONS

Gomes-da-Silva et al., "Challenging the future of siRNA therapeutics against cancer: the crucial role of nanotechnology", Cell. Mol. Life. Sci., 2013, 71, 1417-1438.
Gosh, P., et al., "Gold nanoparticles in delivery applications", 2008, Adv., Drug Deliv. Rev., pp. 1307-1315.
Gu et al., "Cationic amphiphilic macromolecule (CAM)-lipid complexes for efficient siRNA gene silencing", Journal of Controlled Release, 2014, 184, 28-35.
Han et al., "Single-Antibody, Targeted Nanoparticle Delivery of Camptothecin", Molecular Pharmaceuticals, Jul. 1, 2013, vol. 10, No. 7, 2558-2567.
Han et al., "Targeted Nanoparticles Assembled via Complexation of Boronic-Acid-Containing Targeting Moieties to Dial-Containing Polymers", Bioconjugate Chemistry, Mar. 6, 2013, vol. 24, No. 4, 669-677.
Han et al., "Targeted polymer-based nanoparticles containing camptothecin: Development and function", American Association for Cancer Research, Apr. 15, 2012, vol. 72, Issue 8 Supplement, 1-2.
Han, Development of targeted, polymeric delivery vehicles for camptothecin and siRNA via boronic acid-diol complexation, Han han, Thesis (Dissertation Ph.D) of California Institute of Technology, pp. 125-128,2013.
Hou et al., "Development of Zeptomole and Attomolar Detection Sensitivity of Biotin-Peptide Using a Dot-Blot GoldNanoparticle Immunoassay", Anal. Chem., 2007, 79(3), 980-985.
Jiang et al., "Nanoparticle-Mediated Cellular Response is Size-Dependent", Nature Nanotech, 2008, 3(3), 145-150.
Kale et. al., "Design, Synthesis, and Characterization of pH-Sensitive PEG-PE Conjugates for Stimuli-Sensitive Pharmaceutical Nanocarriers: The Effect of Substitutes at the Hydrazone Linkage on the pH Stability of PEG-PE Conjugates", Bioconjugate Chem. 2007, 18, 363-370.
Kamaly et al., "Targed Polymeric Therapeutic Nanoparticles: Design, Development and Clinical Translation", Chem Soc. Rev, 2012, 41, 2971.
Kanasty et al., "Delivery materials for siRNA therapeutics", Nat. Mater., 2013, 12, 967-977.
Kennecke et al., "Metastatic Behavior of breast cancer subtypes", J. Clin. Oncol., 2010, 28, 3271-3277.
Kumar et al., Journal of Neurosurgery, Mar. 1974, vol. 40, pp. 365-371.
Lin et al., "Brain Metastases: the HER2 paradigm", Clin. Cancer Res., 2007, 13, 1648-1655.
Lytton-Jean et al., "Five Years of siRNA delivery: Spotlight on gold nanoparticles", Small, 2011, 7(14), 1932-1937.
Malek et al., "In Vivo Pharmacokinetics, Tissue Distribution and Underlying Mechanisms of Various PEI(-PEG)/siRNA Complexes", Toxicology and Applied Pharmacology, 2009, 236, 97-108.
Mangani et al., "EXAFS Studies on Copper Transferrin", J Inorganic Biochem, 1992, 48(1), 33-40.
Mehta et al., Therapeutic approaches for HER2-positive brain metastases: Circumventing the blood-brain barrier, Cancer Treat. Rev., 2013, 39, 261-269.
Merkel et al., "Stability of siRNA Polyplexes from Poly(ethylenimine) and Poly(ethylenimine)-g-poly(ethlene glycol) Under in Vivo Conditions: Effects on Pharmacokinetics and Biodistribution Measured by Fluorescence Fluctuation Spectroscopy and Single Photon Emission Computed Tomography (SPECT) Imaging", Journal of Controlled Release, 2009, 138, 148-159.
Mikado et al., "Application of Neutron Capture Autoradiography to Boron Delivery Seeking Techniques For Selective Accumulation of Boron Compounds to Tumor with Intra-Arterial Administration of Boron Entrapped Water-in-Oil-Water Emulsion", Nucl Instrum Meth A, 2009, 605, 171-174.
Mittapalli et al., "Paclitaxel-hyaluronic nanoconjugates prolong overall survival in a preclinical brain metastases of breast cancer model", Mol. Cancer Ther., 2013, 12, 2389-2399.

Mittapalli et al., "Quantitative Fluroescence microscopy measures vascular pore size in primary and metastatic brain tumors", Cancer Res., 2017, 77, 238-246.
Mohammad et al., "Liosomal irinotecan accumulates in metastatic lesions, crosses the blood-tumor barrier (BTB) and prolongs survival in an experimental model of brain metastases of triple negative breast cancer", Pharm. Res. 2018, 35.
Morikawa et al., "Capecitabine and lapatinib uptake in surgically resected brain metastases from metastatic breast cancer patients: a prospective study", Neuro. Oncol., 2015, 17, 289-295.
Nelson et al., "Balancing cationic and hydrophobic content of PEGylated siRNA polyplexes enhances endosome escape, stability, blood circulation time, and bioactivity in vivo", ACS Nano., 2013, 7, 8870-8880.
Neuwelt et al., "Strategies to Advance Translational Research into Brain Barriers", Lancet Neural, 2008, 7(1), 84-96.
Oehrlich et al., "Clinical outcome of brain metastases differs significantly among breast cancer subtypes", Oncol. Lett., 2017, 14, 194-200.
Office Action issued for China Patent Application No. 200980131484.0 filed Feb. 12, 2011 dated Feb. 21, 2012 with English translation attached.
Osswald et al., "Impact of blood-brain barrier integrity on tumor growth and therapy response in brain metastases", Clin Cancer Res., 2016, 22, 6078-6087.
Pan et al., "Cationic Mucic acid polymer-based siRNA delivery systems", Bioconjugate Chemistry, 2015, 26(8), 1791-1803.
Pardridge et al., "Delivery of Biologics across the blood-brain barrier with molecular trojan horse technology", BioDrugs, 2017, 31, 503-519.
Pardridge et al., "Drug targeting to the brain", Pharm. Res., 2007, 24, 1733-1744.
Pardridge, "Blood-Brain Barrier Drug targeting: The Future of Brain Drug Development", Molecular Interventions, Mar. 2003, vol. 3, No. 2, 90-105.
Pardridge, "The Blood-Brain Barrier: Bottleneck in Brain Drug Development", NeuroRX, 2005, 2(1), 3-14.
Peer et al., "Nanocarriers as an emerging platform for cancer therapy", Nat. Nanotechnol., Dec. 2007, 2, 751-760.
Pun et al., "Development of a nonviral gene delivery vehicle for systemic application", Bioconjugate Chem., 2002, 13, 630-639.
Pun et al., "Targeted Delivery of RNA-Cleaving DNA Enzyme (DNAzyme) to Tumor Tissue by Transferrin-Modified, Cyclodextrin-Based Particles", Cancer Biology and Therapy, 3, 7, Jul. 2004, 641-650.
Ramakrishna et al., "Recommendations on disease management for patients with advanced human epidermal growth factor receptor 2-positive breast cancer and brain metastases: American Society of Clinical Oncology Clinical Practice Guideline", J. Clin. Oncol., 2014, 32, 2100-2108.
Reineke et al., "Structural Effects of Carbohydrate-Containing Polycations on Gene Delivery. 1. Carbohydrate Size and its Distance from Charge Centers", Bioconjugate Chem, 2003, 14, 247-254.
Rostami et al., "Brain metastasis in breast cancer: a comprehensive literature review", J. Neurooncol., 2016, 127, 407-414.
Sapsford et al. "Functionalizing Nanoparticles with Biological Molecules: Developing Chemistries that Facilitate Nanotechnology", emical Reviews, Feb. 22, 2013, 113, pp. 1904-2074.
Saraiva et al., "Nanoparticle-mediated brain drug delivery: Overcoming -blood-brain barrier to treat neurodegenerative diseases", Journal of Controlled Release, 2016, 235, 34-47.
Sato et al., "Polymer brush-stabilized polyplex for a siRNA carrier with long circulatory half-life," Journal of Controlled Release, 2007, 122, 209-216.
Sawyer et al: Convection-enhanced delivery of camptothecin-loaded polymer nanoparticles for treatment of intracranial tumors, Drug DelivTransl Res. Feb. 1, 2011; 1(1): 34-42.
Sawyer et al: New Methods for Direct Delivery of Chemotherapy for Treating Brain Tumors, Yale Journal of Biology and Medicine 79, 2006, 141-152.

(56) References Cited

OTHER PUBLICATIONS

Shah et al., "Investigational chemotherapy and novel pharmacokinetic mechanisms for the treatment of breast cancer brain metastases", Pharmacol. Res., 2018, 132, 47-68.
Shimizu et al., "siRNA-Based Therapy Ameliorates Glomerulonephritis", J. Am. Soc. Nephrol., 2010, 21, 622-633.
Sonavane, G., et al. "Biodistribution of colloidal gold nanoparticles after intravenous administration: Effect of particle size", Colloids and Surfaces B: Biointerfaces, 2008, pp. 276-280.
Taskar et al., "Lapatinib distribution in HER2 Overexpressing experimental brain metastases of breast cancer", Pharm. Res., 2012, 29, 770-781.
Terrell-Hall et al., "Trastuzumab distribution in an in-vivo and in-vitro model of brain metastases of breast cancer", Oncotarget, 2017, 8, 83734-83744.
Torchilin et al., "TAT Peptide On The Surface Of Liposomes Affords Their Efficient Intracellular Delivery Even At Low Temperature And In The Presence Of Metabolic Inhibitors", PNAS, Jul. 2001, 98(15), 8786-8791.
Tuffin et al., "Immunoliposome Targeting to Mesangial Cells: A Promising Strategy for Specific Drug Delivery to the Kidney", J. Am. Soc. Nephrol., 2005, 16, 3295-3305.
Uchida et al., "Quantitative targeted absolute proteomics of human blood-brain barrier transporters and receptors", J. Neurochem., 2011, 117, 333-345.
Van Rooy et al., "Identification of Peptide Ligands for Targeting the Blood-Brain Barrier", Pharmaceutical Research, Apr. 2010, 27(4), 673-682.
Walburg et al., "Epithelial and Endothelial Barriers in the Olfactory Region of the Nasal Cavity of the Rat", Histochem Cell Biol, 2008, 130(1), 127-140.
Wiley et al: "Transcytosis and brain uptake of transferrincontaining nanoparticles by tuning avidity to transferrin receptor", Proceedings of the National Academy of Sciences, vol. 110, No. 21, May 6, 2013 (May 6, 2013), pp. 8662-8667.
Wolf, W. et al., "F-MRS Studies Of Fluorinated Drugs In Humans", Advanced Drug Delivery Reviews, 2000, 41, 55-74.
Wu et al., "Recent progress in copolymer-mediated siRNA delivery", Journal of Drug Targeting, 2012, 20(7), 551-560.
Wu et al., "RNAi Therapies: Drugging the Undruggable", Science Transl. Med., 2014, 6, 240ps7, 1-8.
Wyatt et al., "Method of establishing breast cancer brain metastases affects brain uptake and efficacy of targeted, therapeutic nanoparticles", Bioeng. Tranls. Med., 2018, doi: 10.1002/btm2.10108.
Xiao et al., "The Effect of Surface Charge on in Vivo Biodistribution of PEG-oligocholic Acid Based Micellar Nanoparticles", Biomaterials, 2011, 32, 3435-3446.
Xue et al. "Highlighting the role of polymer length, carbohydrate size, and nucleic acid type in potency of glycopolycation agents for pDNA and siRNA delivery", Biomacromolecules, 2013, 14, 3903-3915.
Yu et al., "Boosting Brain Uptake of a Therapeutic Antibody by Reducing Its Affinity for a Transcytosis Target", Sci Transl Med, 2011, 3(84), 1-8.
Devi, "siRNA-based Approaches in Cancer Therapy", Cancer Gene Therapy, 2006, vol. 13, pp. 819-829.
"Study on PEGylated polyethyleneimine as a pulmonary gene delivery carrier", Jia Cai, Master's Thesis of Fudan University, Dec. 31, 2006 [English Abstract and Concise Statement of Relevance included].
Venditto et al., Cancer Therapies Utilizing the Camptothecins: A Review of in Vivo Literature, Mol Pharm. Apr. 5, 2010, 7(2), 307-349.
Han Han et al.: "Single-Antibody, Targeted Nanoparticle Delivery of Camptothecin", Molecular Pharmaceutics, vol. 10, No. 7, Jul. 1, 2013 (Jul. 1, 2013), pp. 2558-2567, XP055191493, ISSN: 1543-8384, DOI: 10.1021/mp300702x p. 2559-p. 2560; table 1.
Wyatt Emily A. et al.: "Abstract 4641: Improved chemotherapeutic delivery to brain metastases with targeted nanoparticles in preclinical breast cancer brain metastasis models", American Association for Cancer Research (AACR) Annual Conference, Apr. 17-18, 2018, Chicago, Cancer Research 13 Supplement, [Online] vol. 78, Jul. 1, 2018 (Jul. 1, 2018), p. 1, XP055895586, Retrieved from the Internet: URL: https://aacrjournals.org/cancerres/article/78/13_Supplement/4641/629155/Abstract-4641-improved-chemotherapeutic-delivery.

* cited by examiner

Intracranial (IC)

Intracardiac (ICD)

Intravenous (IV)

NANOPARTICLES FOR CROSSING THE BLOOD BRAIN BARRIER AND METHODS OF TREATMENT USING THE SAME

CROSS REFERENCE TO RELATED APPLICATIONS

This application is a continuation of U.S. patent application Ser. No. 16/438,752 filed Jun. 12, 2019 which application claims priority to U.S. Patent Application No. 62/684,593 filed Jun. 13, 2018, the contents of which are incorporated by reference herein for all purposes.

GOVERNMENT RIGHTS

This invention was made with government support under Grant No. CA151819 awarded by the National Institutes of Health. The government has certain rights in the invention.

TECHNICAL FIELD

The present disclosure is directed to the nanoparticles capable of and for use in delivering therapeutic agents across the blood brain barrier.

BACKGROUND

Chronic diseases of the central nervous system (CNS) are a major cause of morbidity and mortality in the developed world. Alzheimer's disease alone affects over five million people in the United States and is expected to increase to over thirteen million by 2050. Moreover, while the proportion of deaths from many other leading causes of mortality in the United States, such as heart disease and stroke, have seen significant decreases over the last decade, the proportion of deaths from Alzheimer's disease has increased 68%. A similar trend, in both high economic cost and a relative lack of progress in treatment, is seen with many other neurodegenerative diseases, including Huntington's disease, Parkinson's disease, multiple sclerosis, and brain cancers.

Brain metastases of breast cancer are also presenting an increasing challenge in the clinic. Historically, brain metastases were not a major problem for most breast cancer patients because they usually developed late during the disease, and lack of systemic control limited survival. However, new therapies have improved clinical outcomes in some subsets of patients, and brain progression has become a more significant threat to long-term survival. Certain of these cancers are caused by the overexpression HER2, EGFR, HER3, and/or HER4 complexes. For example, in women with human epidermal growth factor 2 (HER2)-positive breast cancer, improved control of systemic disease with new therapies has unmasked brain metastases that historically would have remained clinically silent. Efficacy of therapeutic agents against brain metastases is limited by their inability to permeate the blood-brain and blood-tumor barriers (BBB and BTB) in therapeutic amounts.

Although HER2-targeted therapies can effectively control extracranial disease, they have limited distribution to brain metastases and demonstrate poor efficacy in this setting. That is, while HER2-targeted therapies effectively control systemic disease, their efficacy against brain metastases is hindered by their inability to penetrate the blood-brain and blood-tumor barriers (BBB and BTB). Current therapeutic options such as surgery, radiation and chemotherapy are considered palliative, and rarely provide a significant increase in survival.

As with the delivery of most chemotherapeutics to the brain, delivery of HER2-inhibitors to brain metastases is limited by poor drug penetration across the blood-brain barrier (BBB), a selective cellular barrier that acts as a regulator for the movement of molecules into and out of the brain. The tumor microvasculature associated with brain metastases, often referred to as the blood-tumor barrier (BTB), has increased passive permeability relative to the intact BBB; however, the loss in barrier integrity is limited and highly variable from tumor to tumor and even within the metastatic lesion. Many drugs commonly used to treat HER2-positive breast cancer are unable to reach therapeutic concentrations in the brain and circumventing the BBB and BTB remains a major obstacle in effective treatment of brain metastases.

A major reason for the lack of progress in treating these diseases is due to the presence of the blood-brain barrier (BBB). The BBB is a physical barrier between the CNS parenchyma and vasculature that plays a critical role in maintaining homeostasis within the CNS. The BBB consists of several barriers in parallel, with the two that are best described being the vascular BBB, consisting primarily of the capillary bed, and the blood-cerebrospinal fluid (blood-CSF) barrier, consisting primarily of the choroid plexus. Tight junctions exist between endothelial cells that inhibit paracellular diffusion of polar molecules, macromolecules and cells. This forces solute transport into the CNS to occur primarily across individual endothelial cells. Though critically important for maintaining CNS homeostasis, the impermeability of the BBB to most solutes has proven a tremendous obstacle for drug delivery to the CNS. Currently, 98% of small molecule therapeutics and essentially 100% of large-molecule therapeutics, including, monoclonal antibodies, proteins and gene therapies, do not cross the BBB. Only a small class of drugs-small molecules with high lipid solubility and a low molecular mass (Mr) of <400-500 Daltons (Da)-actually cross the BBB by themselves.

While a low molecular weight and high degree of lipid solubility favor crossing by this mechanism, a drug taken up by the membranes that form the BBB must then partition into the aqueous environment of the brain's interstitial fluid to exert an effect. As a result, a substance that is too lipid soluble can be sequestered by the capillary bed of the barrier and not reach the cells behind the BBB. Thus, while lipid solubility can increase transport rate across the BBB, it can also lower the concentration of the drug in the blood. The percent of administered drug entering the brain is determined by both the rate of transport across the BBB and the amount of drug presented to the brain. Use of lipid solubility to improve drug delivery to the brain must thus find the balance between increased permeation of the BBB and decreased concentrations in blood.

There are only a few diseases of the brain that consistently respond to this category of small molecules, and these include depression, chronic pain, and epilepsy. In contrast, many other serious illness disorders of the brain do not respond to the conventional lipid-soluble-low-Mr small-molecule therapeutics, and these include Alzheimer disease, stroke/neuroprotection, brain and spinal cord injury, brain cancer, HIV infection of the brain, various ataxia-producing disorders, amytrophic lateral sclerosis (ALS), Huntington disease, Parkinson disease (PD), multiple sclerosis (MS). and childhood inborn genetic errors affecting the brain.

The present disclosure is directed to addressing some of these challenges and concerns.

SUMMARY

The present disclosure is directed to nanoparticles suitable for delivering therapeutics and imaging agents across the blood brain barrier to treat a range of neurological conditions and diseases that would benefit from the systemic delivery of these therapeutics and imaging agents across the blood brain barrier. Certain embodiments of the disclosure includes polymer, polymer conjugate, or nanoparticle compositions comprising a polymer or nanoparticle core to which is bonded: (a) at least one targeting agent, the targeting agent comprising a ligand attached to an external surface of the nanoparticle core by a linker; the ligand having an affinity for binding to a receptor expressed by endothelial cells of the blood-brain barrier; and the linker being cleavable when subject to conditions inside an endothelial cell of the blood-brain barrier, wherein the cleavage comprises hydrolysis, chemical reduction, or enzymatic cleavage of the linker; and one or both of (b) at least one small molecule therapeutic agent, optionally linked to the nanoparticle core by way of an optional linker; and/or (c) at least one large molecule therapeutic agent, linked to the nanoparticle by way of an optional linker; wherein the large molecule therapeutic agent, when present, and the targeting agent comprise different chemical entities. In certain preferred embodiments, the composition is a nanoparticle comprises the polymer or nanoparticle core to which is bonded at least one targeting agent, the at least one small molecule therapeutic agent, and the at least one large molecule therapeutic agent.

In other independent embodiments, the polymer or nanoparticle core comprises, consists essentially of, or consists of a polyol containing polymer, a poly(lactic-co-glycolic acid) (PLGA), chitosan, polyethyleneimine, polysaccharide, polyester, polyamide, polyether, polycarbonate, polyacrylate, iron oxide, or gold. In such preferred embodiments, the polymer or nanoparticle core comprises, consists essentially of, or consists of a polyol-containing polymer, preferably a sugar-containing polymer, for example, a polymer derived from glucose, fructose, mannitol, mucic acid, sucrose, galactose, sorbitol. xylose or galactose, more preferably from mucic acid. A wide range of such structures are set forth herein.

Additionally, or alternatively, the polymer or nanoparticle core independently comprises units of the formula:

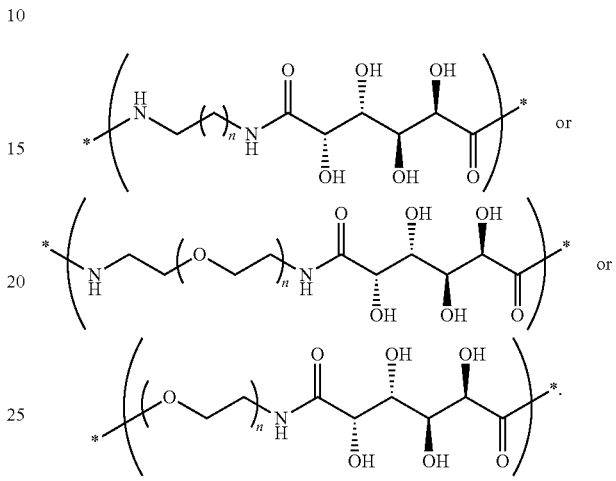

Additionally, or alternatively, in some embodiments, the polymer or nanoparticle core comprises a polymer containing a polyol, wherein the polymer containing the polyol is derived from the coupling of a compound of Formula A:

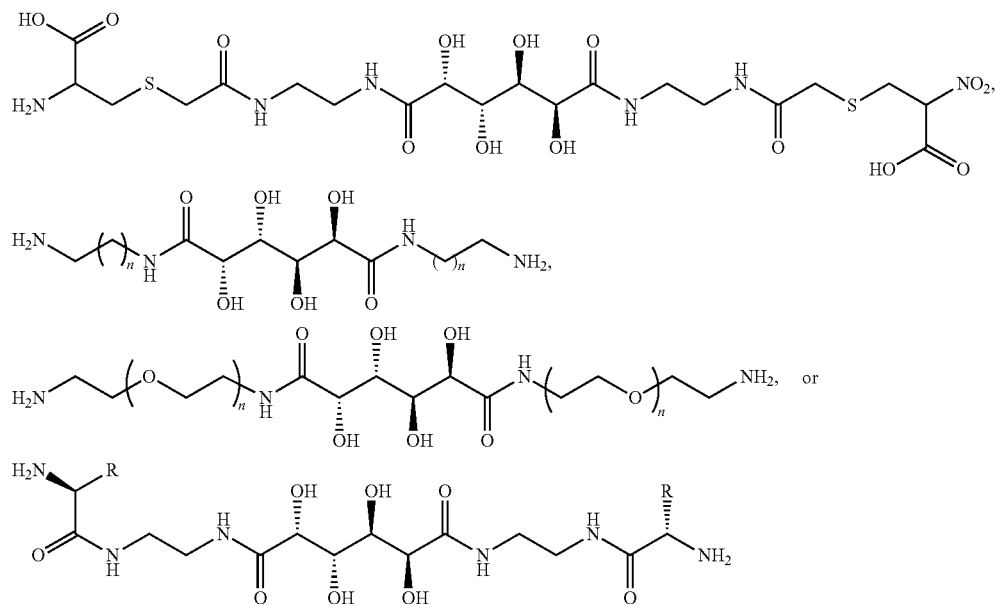

with a compound of Formula B:

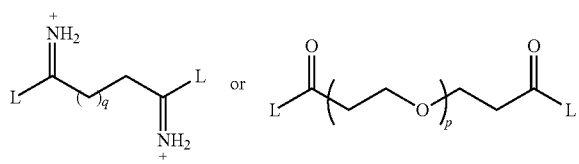

wherein n, q, p, L, and R are described elsewhere herein. Additionally, or alternatively, in some embodiments, the compound of Formula B does not include:

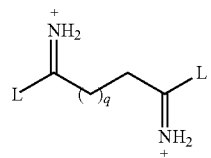

Additionally, or alternatively, in some embodiments, the polymer or nanoparticle core comprises a polymer or nanoparticle core polymer comprises a polyol structure:

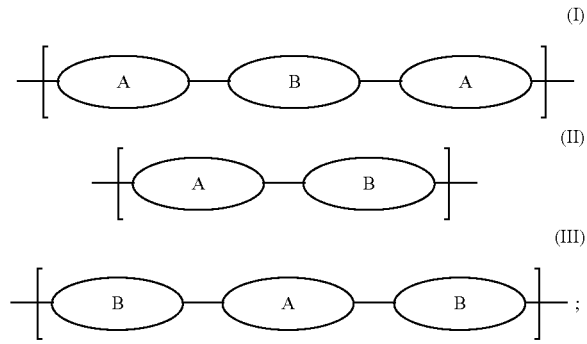

where X, Y, and R are defined elsewhere herein.

Additionally, or alternatively, in some embodiments, the polymer or nanoparticle core comprises a polymer or nanoparticle core polymer comprises alternating charged and uncharged segments comprising one or more of the following structural units of Formula (I) or Formula (II) or Formula (III):

$$\left[ A - B - A \right] \quad (I)$$

$$\left[ A - B \right] \quad (II)$$

$$\left[ B - A - B \right] \quad (III)$$

where A is an uncharged segment comprising polyalkylene glycol; and B is a cationically charged segment comprising at least one polyhydroxy linkage comprising at least one pair of vicinal diols. In some of these embodiments, the B segment comprises at least one repeating subunit comprising a caionic mucic acid polymer (cMAP) residue structure. Various structures and permutations of these A and B segments, and their associated structures, are set forth elsewhere herein.

Additionally, or alternatively, in some independent embodiments, the cleavable linker between the targeting ligand and the polymer or nanoparticle core comprises one or more of an acetal, borate ester, a carboxylic ester, a diaminoketal, a disulfide, a ketal, a hydrazone, an imine, a ketal, an orthoester, or a peptide linkage. These linkages are variously susceptible to cleavage under the conditions associated with a brain endothelial cell, for example by hydrolysis, chemical reduction, enzymatic cleavage, or other means. In certain specific embodiments, the cleavable linkage comprises at least one borate ester of a (nitro)phenyl boronic acid-containing polymer comprising a structure:

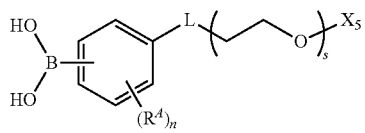

where $R^4$, n, S, and $X^5$ are set forth elsewhere herein. Various additional configurations of such linkages are set forth herein. This linkage, cleavable within the endothelial cell, is critical to these nanoparticles' ability to ferry cargo across the blood brain barrier and other barriers.

In some embodiments the at least one targeting ligand independently comprises or consists of a nucleotide, polynucleotide, aptamer, peptide, oligopeptide, polypeptide, protein, polysaccharide, antibody or antibody fragment. Additionally, or alternatively, and as described elsewhere herein, the at least one of the targeting ligands is one known to specifically bind to receptor or surface protein expressed by a brain endothelial cell that undergoes transcytosis. A wide variety of useful targeting ligands are set forth elsewhere within this disclosure. In certain additional or alternative embodiments comprise or consist of, but are not limited to, chemical entities that specifically bind to certain identified targeted receptors. Transferrin is an attractive option for this targeting ligand and serves as a specific embodiment in this capacity.

Each polymer or nanoparticle core can be conjugated to a single targeting ligand (per core) or to several thousand such targeting ligands (per core). Moreover, the polymer or nanoparticle core can be conjugated to a single type of targeting ligand or multiple types. Further, while at least one targeting ligand must be conjugated to each polymer or nanoparticle core by a cleavable linkage, as set forth elsewhere herein, additional targeting ligands can also be linked to the core with non-cleavable linkages, offering added functionality to the structures. Still further, the polymer or nanoparticle core may further comprise free pendant moieties capable of acting as linking groups (cleavable or otherwise) to which no targeting linkages are attached. Such linkable groups offer the possibility for attaching other biological, chemical, or imaging agents to the core, or may link such biological, chemical, or imaging agents to the core.

In certain independent embodiments, the small molecule optionally attached to the polymer or nanoparticle core is a pharmaceutical compound useful in the treatment of Alzheimer's disease, Huntington's disease, Parkinson's disease, multiple sclerosis, and brain cancer. Such compounds include neurotransmitters, chemotherapeutic, and other biologically active materials. Compounds such as dopamine, serotonin, camptothecin, irinotecan, SN-38, or a derivative, metabolite, or prodrug thereof are but a small list of compounds set forth in this disclosure.

Alternatively, or additionally, the small molecule can also be "tagged" with radio-isotopes for molecular imaging of the tumor marker in vivo.

In certain independent additive or alternative embodiments, the small molecule therapeutic compound may be chemically or electrostatically bonded to the polymer or nanoparticle core or may be encapsulated within the structure of the nanoparticle core without being chemically or electrostatically bonded thereto. When chemically linked, the small molecule linker may be either chemically stable (i.e., able to maintain its structure in its presented or intended environment) or may be cleavable by any of the mechanisms associated with the term "cleavable" as set forth elsewhere herein. Additionally, or alternatively, this linking group may comprise one or more amino acid residues, such as a residue of arginine, histidine, lysine, aspartic acid, glutamic acid, serine, threonine, asparagine, glutamine, tyrosine, tryptophan, or a salt thereof.

In certain independent embodiments, the large molecule therapeutic agent is a nucleotide, polynucleotide, aptamer, peptide, oligopeptide, polypeptide, protein (including fusion proteins), polysaccharide, antibody or antibody fragment useful in the treatment of Alzheimer's disease, Huntington's disease, Parkinson's disease, multiple sclerosis, and cancer. In certain Aspects of this Embodiment, the large molecule is an antibody. In this regard, the present disclosure exemplifies the use of trastuzumab (Herceptin®) in this capacity, though the large molecule therapeutic agent is not so limited to this material, and the disclosure sets for a wide range of materials useful in this capacity.

As with the small molecule compound, the large molecule therapeutic compound may be attached to the polymer or nanoparticle core either by a direct chemical bond or via a linking group. The linking group may be either chemically stable (i.e., able to maintain its structure in its presented or intended environment) or may be cleavable by any of the mechanisms associated with the term "cleavable" as set forth elsewhere herein. Additionally, or alternatively, this linking group may comprise one or more amino acid residues, such as for example arginine, histidine, lysine, aspartic acid, glutamic acid, serine, threonine, asparagine, glutamine, tyrosine, tryptophan, or a salt thereof.

While the compositions have been disclosed in terms of a polymer, polymer conjugate, or nanoparticle composition in preferred embodiments, the composition is a nanoparticle. The disclosure also embraces populations of nanoparticles, and pharmaceutical compositions derived therefrom.

Additionally, the disclosure embraces methods of using these nanoparticle compositions for systemically delivering enhanced levels of therapeutics, including the combination of small and large molecule therapeutics, past the blood brain barrier and into the brain parenchyma. Such methods are directed to specific patient populations, previously identified for such treatment. These methods comprise systematically administering to such a subject having a neurological brain disorder and in need of such treatment the nanoparticles as disclosed herein. In this context, the enhanced level of the therapeutic agent delivered by the nanoparticles to the brain parenchyma can be defined as an amount that is greater than is delivered using otherwise equivalent nanoparticles that do not contain the cleavable linker under the same conditions. Several means for determining the effectiveness are set forth elsewhere herein.

In some embodiments, the disclosed treatments include those where the attached small or large molecule therapeutic agent is otherwise incapable of passing through the blood brain barrier to deliver therapeutically effective amounts of the agent. In still other embodiments, this administration is accompanied by the co-administration of a therapeutic or imaging agent that is itself able to pass the blood brain barrier and deliver therapeutic amounts in the brain parenchyma. This tandem administration may be provided at the same time, in the same delivery vehicle, or at different times, in different delivery vehicles during a given treatment regime. In this context, the enhanced level of the therapeutic agent delivered by the nanoparticles to the brain parenchyma can be defined as an amount that is greater than is delivered using otherwise equivalent nanoparticles that do not contain the cleavable linker under the same conditions.

The methods of administering these compositions, and the certain neurological conditions suitable for treatment are set forth elsewhere herein.

BRIEF DESCRIPTION OF THE DRAWINGS

The present application is further understood when read in conjunction with the appended drawings. For illustrating the subject matter, there are shown in the drawings exemplary embodiments of the subject matter; however, the presently disclosed subject matter is not limited to the specific methods, devices, and systems disclosed. In addition, the drawings are not necessarily drawn to scale. In the drawings:

FIGS. 5(A-C) illustrates of breast cancer brain metastasis models.

FIGS. 12(A-B) show brain uptake of therapeutics is model-dependent in tumor, but not healthy tissue.

FIG. 14(A-B) shows synthetic schemes for nitroPBA conjugates.

DETAILED DESCRIPTION OF ILLUSTRATIVE EMBODIMENTS

The present disclosure is directed to nanoparticles comprising targeting agents and therapeutics and/or imaging agents, suitable for, but not limited to, delivering the therapeutics and/or imaging agents to the brain of a subject. In some embodiments, the described nanoparticles are loaded with the therapeutic agent and/or imaging agent of interest prior to administration of the nanoparticle to the subject. Following delivery of the loaded nanoparticle, the targeting ligand facilitates delivery of the nanoparticle to a target cell of interest, such as a brain endothelial cell. Following internalization by the target cell, the nanoparticle dissociates from the targeting agent. In the case of brain endothelial cells, the internalized nanoparticle will then be excreted from the cell into the interstitial space of the brain where the particle will destabilize and secrete the loaded agent, thereby delivering the agent to the brain or other target location. In some embodiments the described methods may be carried out to deliver a neurotransmitter such as serotonin or dopamine to the brain, which may be used to treat a neurological disorder. Other agents for use in treating neurological disorders may also be delivered to the brain via the described methods. Imaging agents that might not readily access the brain on their own may also be delivered using the described methods. In some embodiments the described methods may be used to deliver a nanoparticle carrying the imaging agent Cu64 to the brain of a subject to allow for imaging. Further, the described methods may be used to deliver a combination of one or more therapeutic agents, imaging agents, or both therapeutic agents, imaging agent to the brain of a subject.

In certain embodiments, the nanoparticles contain therapeutics suitable for the control and treatment of cancer-tumors, especially cancer-tumors of the brain. More specifically, the instant disclosure materials and methods which allow therapeutics to cross the blood-brain-barrier (BBB) and blood-tumor-barriers (BTB) for the treatment of conditions including metastatic, HER2-positive brain tumors.

There has been significant interest in engineering nanoparticles and other nanoscale or polymeric drug formulations to enhance the delivery of therapeutic agents to the brain following systemic administration. The use of endogenous transport mechanisms at the BBB such as receptor-mediated transcytosis (RMT) has emerged as a promising approach to shuttle a variety of payloads across the BBB. In particular, transferrin receptor (TfR) has been one of the primary targets investigated for RMT because of its high expression on the blood side of the BBB endothelium.

Figure 1A:
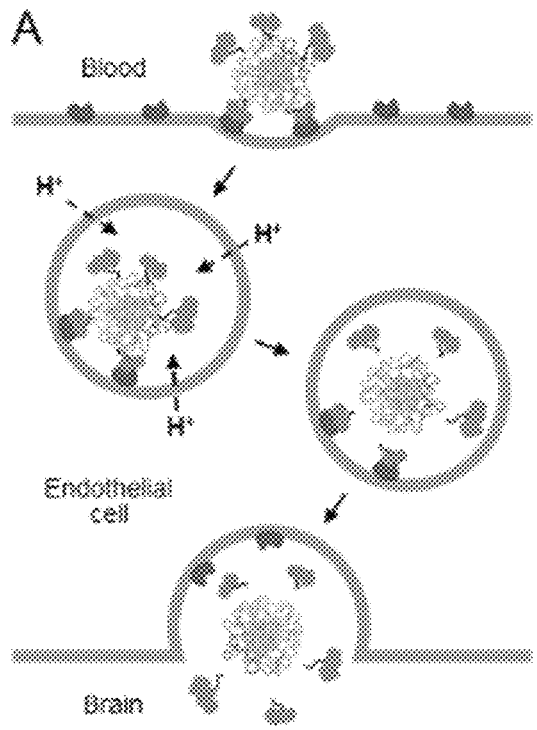
FIG. 1(A) shows a scheme of acid-cleavable targeting strategy. Following endocytosis, rapid acidification of endosome triggers separation of Tf ligands from the nanoparticle core, allowing free diffusion of the nanoparticle into the brain parenchyma after transcytosis.
Figure 1B:
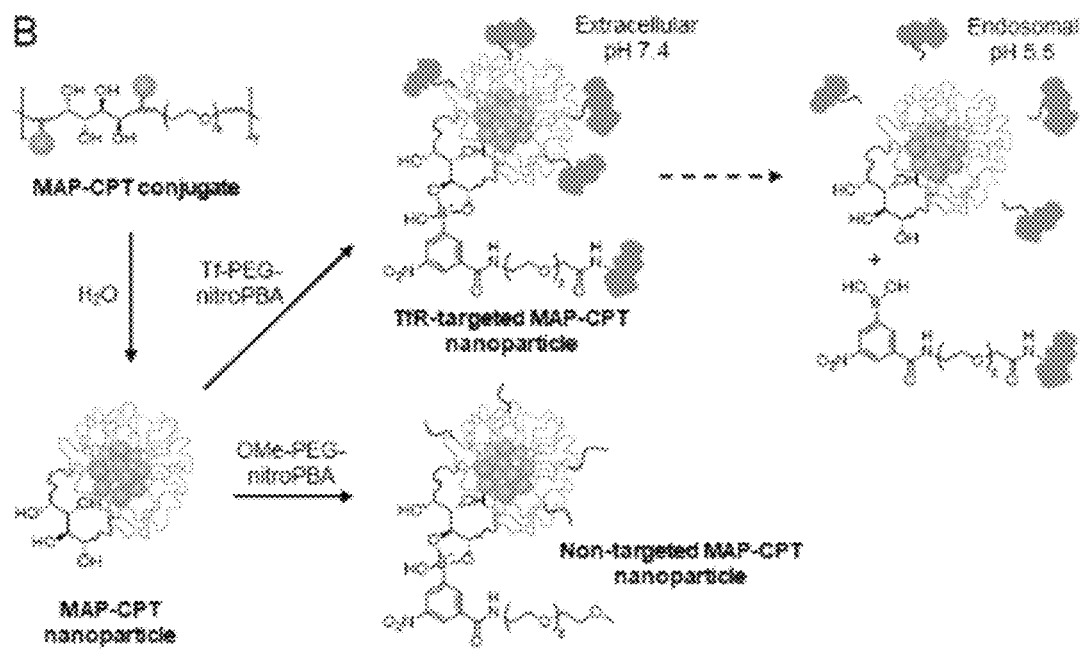
FIG. 1(B) illustrates the preparation of TfR-targeted and non-targeted MAP-CPT nanoparticles and pH-dependence of nitroPBA-diol complex. x~82 for 3.4 kDa PEG; y~20 for material used in this study; z~120 for 5 kDa PEG.

As described herein, the inventors investigated the brain uptake and efficacy of TfR-targeted therapeutic nanoparticles designed to transcytose the BBB/BTB. Transferrin (Tf) was attached to nanoparticles consisting of a mucic acid polymer (MAP) conjugate of camptothecin (CPT), denoted MAP-CPT, through a pH-dependent, boronic acid-diol complexation to the vicinal diols contained within the mucic acid portions of the polymer. With this acid-cleavable targeting strategy, nanoparticles retain high avidity to TfR on the blood side of the BBB to enable practical, systemic dosing, yet release the targeting agents upon acidification during transcytosis to allow their release into the brain. FIGS. 1(A-B). The present inventors have demonstrated that these targeted nanoparticles, administered systemically, were able to deliver CPT to HER2-positive breast cancer brain metastases in mice and eliciting a considerable antitumor response.

Figure 2:
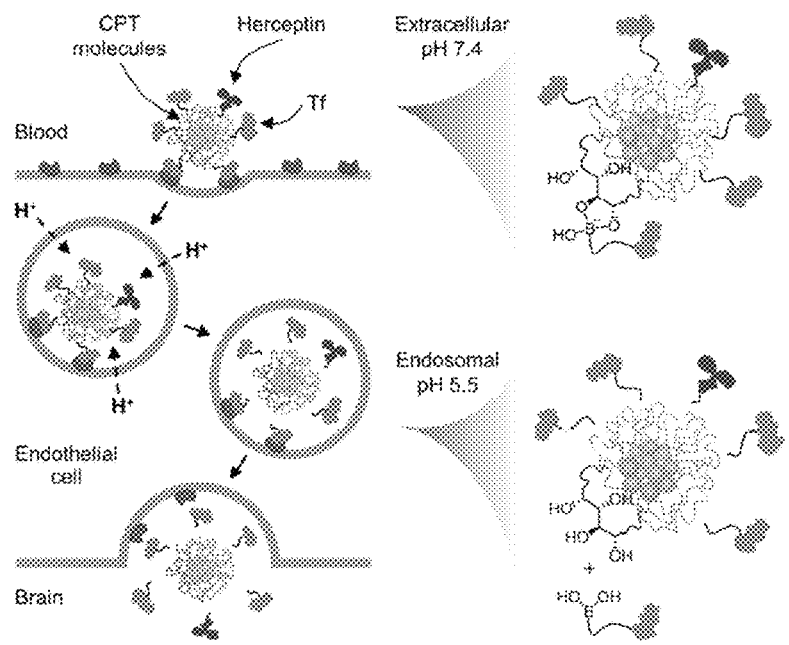
FIG. 2 illustrates a proposed mechanism for delivery of drug and antibody combination to brain metastases using acid-cleavable targeting ligands. At extracellular pH 7.4, Tf ligands and Herceptin remain bound to the diols on the nanoparticle surface. After endocytosis, rapid acidification of the endosome to pH 5.5 triggers their dissociation from the nanoparticle core, allowing free diffusion into the brain once transcytosis is complete.

The present inventors further hypothesized that TfR-targeted nanoparticles carrying more potent therapeutic agents would reveal even greater tumor size reductions. In this disclosure, an exemplary delivery system was investigated for its ability to shuttle an anti-HER2 monoclonal antibody, Herceptin, alone or in combination with a CPT payload, across the BBB to achieve enhanced antitumor activity over the previously reported efficacy of CPT alone (FIG. 2).

The present application discloses nanoparticles carrying therapeutic agents, including chemotherapeutic agent, and targeting ligands, where the nanoparticles are suitable for delivering these chemotherapeutic agents throughout a patient, including through the blood the blood brain barrier and methods of using these patients on those patients in need of such treatment. While described in terms of chemotherapy, it is appreciated that some of the nanoparticles are also capable of carrying therapeutics not directed to cancer across the blood brain barrier for treatment of other neurological conditions, for example serotonin or dopanine for treatment of diseases such as Parkinson's disease, Huntington disease, and multiple sclerosis, such as described in U.S. Patent Application Publ. No. 2014/0348754, which is incorporated by reference herein for all purposes, but at least for the use of the nanoparticles for this purpose.

The present disclosure in its full context, includes sections labeled General Terms, General Embodiments of the Present Disclosure, and Examples. These sections more fully describe the following enumerated aspects of the present disclosure, as well as embodiments not listed as follows. None of these sections, or provisions that follow, are to be interpreted as limiting the disclosure to any particular section, and should be considered in total for the teachings of the present disclosure.

ASPECT 1: A method of treating a neurological disorder in a patient, the method comprising systemically administering a first small molecule therapeutic agent and/or a large molecule therapeutic agent to the patient in need of such treatment, wherein (a) the first small molecule therapeutic agent and/or the large molecule therapeutic agent is attached to a nanoparticle comprising a nanoparticle core and a targeting agent, the targeting agent comprising at least one targeting ligand attached to an external surface of the nanoparticle core by a linker having a cleavable linkage;

(i) the external surface of the nanoparticle comprising a neutral and/or negatively charged mucic acid-containing polymer (MAP) (including where the nanoparticle core and/or surface is substantially free of cationic mucic-acid containing polymer (cMAP));

(ii) the at least one targeting ligand having an affinity for binding to a receptor expressed by endothelial cells of the blood-brain barrier; and (iii) the cleavable linkage being cleavable when subject to conditions inside an endothelial cell of the blood-brain barrier, wherein the cleavage comprises hydrolysis, chemical reduction, or enzymatic cleavage of the linker; and wherein one or both of (iv) the small molecule therapeutic agent is optionally linked to the nanoparticle core by way of an optional linker; and/or (v) the large molecule therapeutic agent is linked to the nanoparticle by way of an optional linker; and (b) the administration of the first small molecule therapeutic agent and/or the large molecule therapeutic agent attached to the nanoparticle results in the delivery of the first small molecule therapeutic agent and/or the large molecule therapeutic agent past the blood brain barrier and into the subject's brain parenchyma in an amount is greater than would be delivered were the first small molecule therapeutic agent and/or the large molecule therapeutic agent not attached to the nanoparticle.

ASPECT 2. The method of ASPECT 1, wherein the method comprises delivering the large molecule therapeutic agent attached to the nanoparticle, such that the large molecule therapeutic agent is delivered past the blood brain barrier and into the subject's brain parenchyma in an amount that is greater than would be delivered were the large molecule therapeutic agent not attached to the nanoparticle.

ASPECT 3. The method of ASPECT 1 or 2, wherein the amount of the large molecule therapeutic agent that passes the blood brain barrier and into the subject's brain parenchyma is a therapeutically effective amount for the neurological disorder.

ASPECT 4. The method of any one of ASPECTS 1 to 3, further comprising systemically administering to the patient a second small molecule therapeutic agent that itself able to pass the blood brain barrier and be delivered into the subject's brain parenchyma in a therapeutically effective amount, wherein the second small molecule therapeutic agent is not attached to the nanoparticle.

ASPECT 5. The method of any one of ASPECTS 1 to 4, wherein the first and second small molecule therapeutic agents are not the same.

ASPECT 6. The method of any one of ASPECTS 1 to 5, wherein the method comprises delivering both the first small molecule therapeutic agent and the large molecule therapeutic agent, both attached to the nanoparticle, such that both the first small molecule therapeutic agent and the large molecule therapeutic agent are delivered past the blood brain barrier and into the subject's brain parenchyma in amounts that are individually greater than would be delivered were the small molecule therapeutic agent and the large molecule therapeutic agent large molecule therapeutic agent not attached to the nanoparticle.

ASPECT 7. The method of any one of ASPECTS 1 to 6, wherein the amount of first small molecule therapeutic agent and the large molecule therapeutic agent that passes the blood brain barrier and into the subject's brain parenchyma are individually a therapeutically effective amount for the neurological disorder.

ASPECT 8. The method of any one of ASPECTS 1 to 7, wherein the neurological disorder is brain cancer, including brain cancer metastasized other systemic, extracranial cancers, including brain cancer metastasized from HER2-positive breast cancer.

ASPECT 9. The method of any one of ASPECTS 1 to 8, wherein the nanoparticle core comprises a polymer comprising units of the formula:

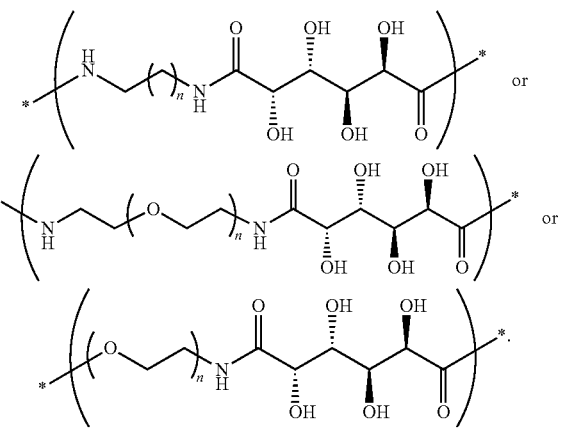

ASPECT 10. The method of anyone of ASPECTS to 9, wherein the nanoparticle core comprises a polyol structure:

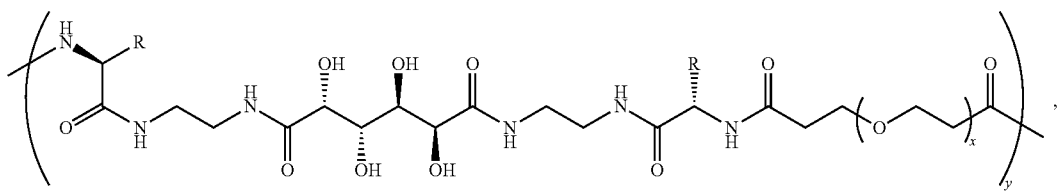

where y is in a range of from 10 to 25;
where R is afunctional group residue corresponding to that of an amino acid containing a third functional group, for example arginine (R is $CH_2CH_2CH_2NHC(NH_2)_2^+$), histidine (R is $CH_2$-imidazolyl), lysine (R is $CH_2$—$CH_2$—$CH_2$—$CH_2$—$NH_2$), aspartic acid (R is $CH_2$—COOH), glutamic acid (R is $CH_2$—$CH_2$—COOH), serine (R is $CH_2$—OH), threonine (R is CH(OH)($CH_3$)) asparagine (R is $CH_2$—C(O)$NH_2$), glutamine (R is $CH_2$—$CH_2$—C(O)$NH_2$), tyrosine (R is $CH_2$-Ph-OH), tryptophan (R is $CH_2$-indolyl), or a salt thereof, and/or where R is coupled to one or more of the targeting agent, the first small molecule therapeutic agent, and/or the large molecule therapeutic agent.

ASPECT 11. The method of any one of ASPECTS 1 to 10, wherein the nanoparticle core comprises a polymer derived from the coupling of a compound of Formula A with a compound of Formula B; wherein the compound of Formula A is:

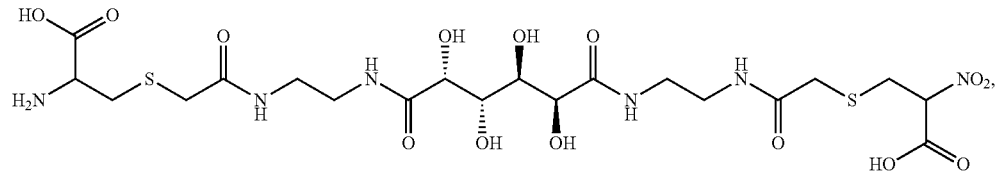

-continued

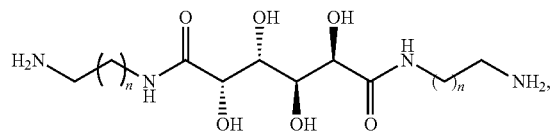

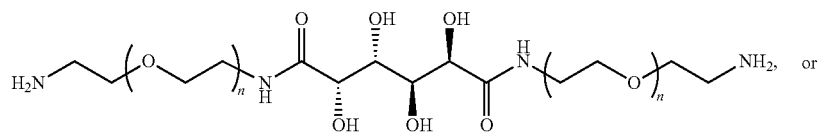

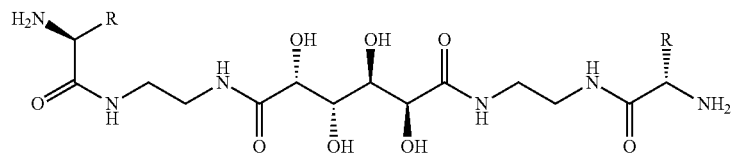

wherein n is a number from 1 to 20; and
R is a functional group residue (e.g., —COOH, —NH$_2$, —OH) corresponding to that of an amino acid containing a third functional group, for example arginine (R is CH$_2$CH$_2$CH$_2$NHC(NH$_2$)$_2$$^+$), histidine (R is CH$_2$-imidazolyl), lysine (R is CH$_2$—CH$_2$—CH$_2$—CH$_2$—NH$_2$), aspartic acid (R is CH$_2$—COOH), glutamic acid (R is CH$_2$—CH$_2$—COOH), serine (R is CH$_2$—OH), threonine (R is CH(OH)(CH$_3$)) asparagine (R is CH$_2$—C(O)NH$_2$), glutamine (R is CH$_2$—CH$_2$—C(O)NH$_2$), tyrosine (R is CH$_2$-Ph-OH), tryptophan (R is CH$_2$-indolyl), or a salt thereof, and the compound of Formula B is:

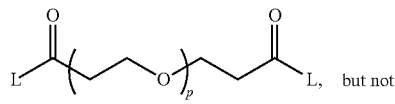 but not

-continued

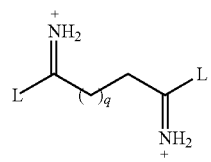

in which
p is a number from 20 to 200; and
L is a leaving group.

ASPECT 12. The method of any one of ASPECTS 1 to 11, wherein the nanoparticle core comprises a polymer comprises units of the formula:

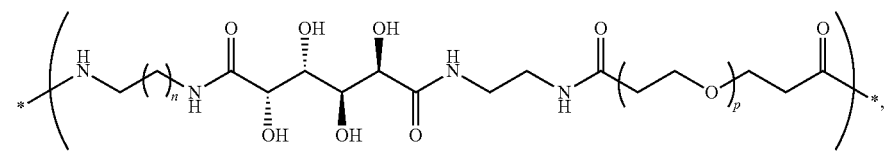

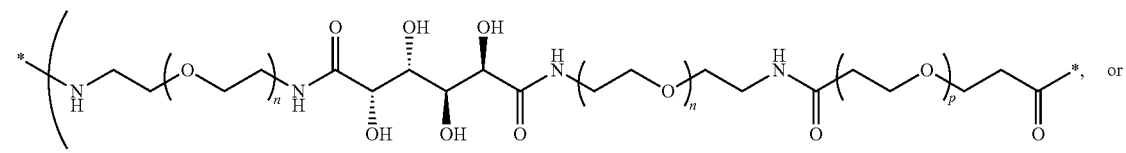

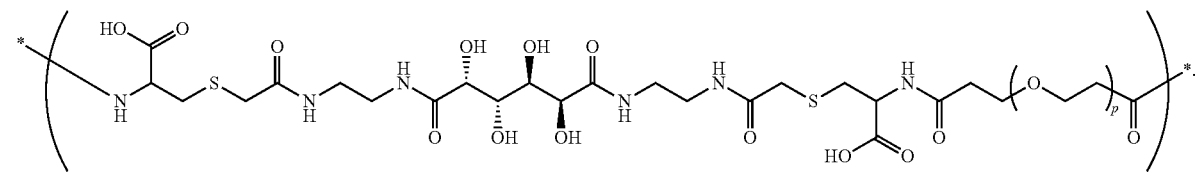

wherein n is a number from 1 to 20 and p is a number from 20 to 200.

ASPECT 13. The method of any one of ASPECTS 1 to 13, wherein the cleavable linkage comprises an acetal, a borate ester, a carbonate, a carboxylic acid ester, a diamino ketal, a disulfide, a hydrazone, an imine, a ketal, an orthoester, or a peptide linkage.

ASPECT 14. The method of any one of ASPECTS 1 to 13, wherein the at least one targeting agent comprises at least one borate ester of a (nitro)phenyl boronic acid-containing polymer comprising a structure:

ASPECT 16. The method of any one of ASPECTS 1 to 15, wherein the first small molecule therapeutic agent is a neurotransmitter or a chemotherapeutic agent.

ASPECT 17. The method of any one of ASPECTS 1 to 16, wherein the first small molecule therapeutic agent is dopamine, serotonin, camptothecin, irinotecan, SN-38, or a metabolite, or prodrug thereof.

ASPECT 18. The method of any one of ASPECTS 1 to 17, wherein the nanoparticle comprises a unit structure:

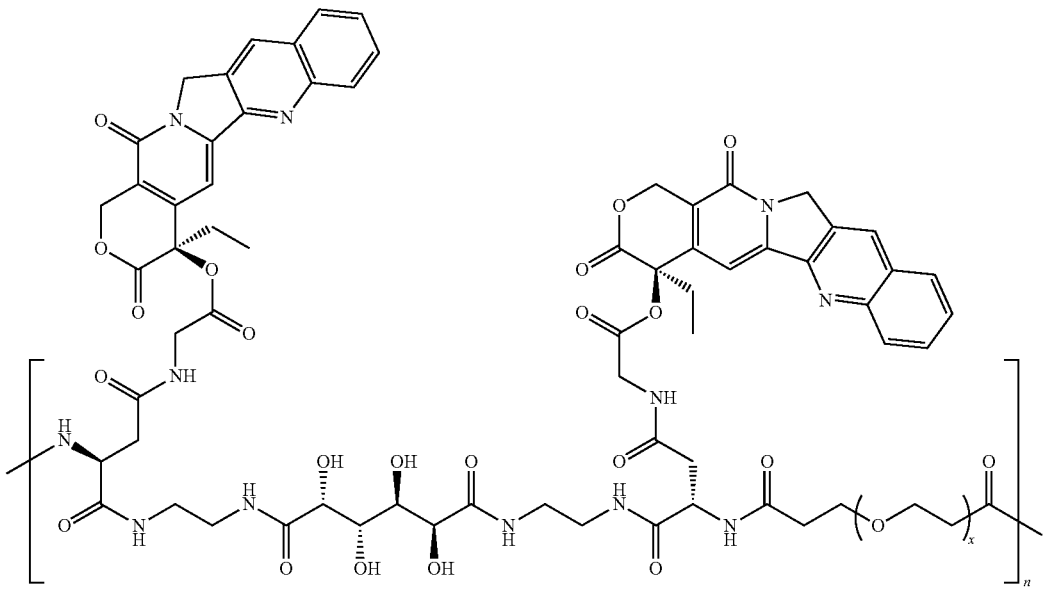

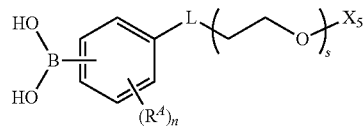

wherein
the nanoparticle core and the (nitro)phenyl boronic acid-containing polymer are reversible connected to one another by the borate condensation linkage between the (nitro)phenyl boronic acid moieties of the (nitro)phenyl boronic acid-containing polymer and at least one pair of vicinal diols of the nanoparticle core, $X_5$ being at the distal end of this connection;
$R^A$ is nitro;
n is 1;
s is a number in a range of from 2 to 2000;
L is a linking group between the phenyl ring and the polyethylene oxide linkage, the linking group comprising an amide, carbonate, ester, or disulfide group; and
$X_5$ is a $C_{1-6}$ alkyl, optionally substituted with —OH, —COOH, —B(OH)$_2$—, —C(=O)O(alkyl), —C(=O)O(aryl), —NH$_2$, —NH(alkyl), —N(alkyl)$_2$, or —SH, wherein the at least one targeting agent is coupled thereto.

ASPECT 15. The method of any one of ASPECTS 1 to 14, wherein the first small molecule therapeutic agent is linked to the nanoparticle core by a linker comprising an amino acid residue.

ASPECT 19. The method of any one of ASPECTS 1 to 18, wherein the targeting ligand is transferrin.

ASPECT 20. The method of any one of ASPECTS 1 to 19, wherein the large molecule therapeutic agent is trastuzumab (Herceptin).

ASPECT 21. The method of any one of ASPECTS 1 to 20, wherein the first small molecule therapeutic agent is camptothecin, irinotecan, SN-38, or a metabolite, or prodrug thereof and the large molecule therapeutic agent is trastuzumab (Herceptin).

General Terms

In the present disclosure the singular forms "a," "an," and "the" include the plural reference, and reference to a particular numerical value includes at least that particular value, unless the context clearly indicates otherwise. Thus, for example, a reference to "a material" is a reference to at least one of such materials and equivalents thereof known to those skilled in the art.

When a value is expressed as an approximation by use of the descriptor "about," it will be understood that the particular value forms another embodiment. In general, use of the term "about" indicates approximations that can vary depending on the desired properties sought to be obtained by the disclosed subject matter and is to be interpreted in the specific context in which it is used, based on its function. The person skilled in the art will be able to interpret this as a matter of routine. In some cases, the number of significant figures used for a particular value may be one non-limiting method of determining the extent of the word "about." In other cases, the gradations used in a series of values may be used to determine the intended range available to the term "about" for each value. Where present, all ranges are inclusive and combinable. That is, references to values stated in ranges include every value within that range.

It is to be appreciated that certain features of the invention which are, for clarity, described herein in the context of separate embodiments, may also be provided in combination in a single embodiment. That is, unless obviously incompatible or specifically excluded, each individual embodiment is deemed to be combinable with any other embodiment(s) and such a combination is considered to be another embodiment. Conversely, various features of the invention that are, for brevity, described in the context of a single embodiment, aspects, Embodiment, or Aspect may also be provided separately or in any sub-combination. Finally, while an embodiment may be described as part of a series of steps or part of a more general structure, each said step may also be considered an independent embodiment in itself, combinable with others. Still further, where certain features are described in terms of a one category (e.g., in terms of a method or composition), it is to be understood that that feature is equally applicable to all categories (e.g., features described in the context of compositions are also applicable to methods, and vice versa).

The transitional terms "comprising," "consisting essentially of," and "consisting" are intended to connote their generally in accepted meanings in the patent vernacular; that is, (i) "comprising," which is synonymous with "including," "containing," or "characterized by," is inclusive or open-ended and does not exclude additional, unrecited elements or method steps; (ii) "consisting of" excludes any element, step, or ingredient not specified in the claim; and (iii) "consisting essentially of" limits the scope of a claim to the specified materials or steps and those that do not materially affect the basic and novel characteristic(s) of the claimed invention. Embodiments described in terms of the phrase "comprising" (or its equivalents), also provide, as embodiments, those which are independently described in terms of "consisting of" and "consisting essentially of." For those composition embodiments provided in terms of "consisting essentially of," the basic and novel characteristic(s) is the ability to provide the described effect associated with the description as described herein or as explicitly specified. In particular here, the basic and novel characteristic of the methods and compositions are the ability, at least, to deliver cargo across the blood brain barrier using systemic administrations at levels that would not be achieved by the systemic administration of the cargo by itself.

When a list is presented, unless stated otherwise, it is to be understood that each individual element of that list, and every combination of that list, is a separate embodiment. For example, a list of embodiments presented as "A, B, or C" is to be interpreted as including the embodiments, "A," "B," "C," "A or B," "A or C," "B or C," or "A, B, or C." That is, where lists are provided within an embodiment, additional embodiments include those lists that exclude one or more elements of the first list, without the need for specific exclusions. For example, embodiments described in terms of the amino acid residues arginine, histidine, lysine, aspartic acid, glutamic acid, serine, threonine, asparagine, glutamine, tyrosine, tryptophan, or a salt thereof also include, as separate embodiments, lists where one or more of these amino acids are excluded Throughout this specification, words are to be afforded their normal meaning, as would be understood by those skilled in the relevant art.

Where a composition is administered to a patient or subject, the term "administration" means application of the composition to the patient or subject. The terms "systemic administration," "administered systemically," "peripheral administration" and "administered peripherally" as used herein mean the administration of a nanoparticle or composition thereof other than directly into the central nervous system, such that it enters the individual's system and, thus, is subject to metabolism and other like processes, for example, subcutaneous administration. The terms "parenteral administration" and "administered parenterally" as used herein means modes of administration other than enteral and topical administration, usually by injection, and includes, without limitation, intravenous, intramuscular, intra-arterial, intrathecal, intracapsular, intraorbital, intracardiac, intradermal, intraperitoneal, transtracheal, subcutaneous, subcuticular, intraarticular, subcapsular, subarachnoid, and intrastemal, injection and infusion.

Formulations suitable for parenteral administration usually comprise a sterile aqueous preparation of the active compound, which preferably is isotonic with the blood of the recipient (e.g., physiological saline solution). Such formulations may be presented in unit-dose or multi-dose form.

Actual dosage levels of the active ingredient or agent in the pharmaceutical compositions herein described may be varied to obtain an amount of the active ingredient which is effective to achieve the desired therapeutic response for a particular individual, composition, and mode of administration, without being toxic to the individual.

In some embodiments, the patients or subjects are administered at least one of the described nanoparticles or populations of nanoparticles in an individual or daily dose in a range of from about 0.01 µg to 5000 mg per dose or per kg of the weight of the subject. In additional or alternative embodiments, the patient or subject is administered at least one of the nanoparticles or populations of nanoparticles set forth herein at a daily or individual dose in a range of from 0.01 µg to 0.1 µg, from 0.1 µg to 1 µg, from 1 µg to 10 µg, from 10 µg to 100 µg, from 100 µg to 1000 µg, from 1 mg to 5 mg, from 5 mg to 10 mg, from 10 mg to 50 mg, from 50 mg to 100 mg, from 100 mg to 150 mg, from 150 mg to 200 mg, from 200 mg to 250 mg, from 250 mg to 500 mg, from 500 mg to 750 mg, from 750 mg to 1000 mg, from 1000 mg to 2000 mg, from 2000 mg to 3000 mg, from 3000 mg to 4000 mg, or from 4000 mg to 5000 mg per dose or per kg of the weight of the subject, or the daily or individual dose is defined by two or more of the foregoing ranges, for example, from 0.1 µg to 1 mg per kg of body weight or from 1 mg to 10 mg per dose or from 10 mg to 1000 mg per day. In some embodiments, the described methods may be carried out so the nanoparticles described herein is administered to a subject weekly, bi-weekly, monthly, bi-month, semiannually, or annually. Treatment may be initiated with smaller dosages that are less than the optimum dose followed by an increase in dosage over the course of the treatment until the optimum effect under the circumstances is reached.

The term "agent" as used herein indicates a compound capable of exhibiting a chemical or biological activity associated to the target. The term "chemical activity" as used herein indicates the ability of the molecule to perform a chemical reaction. The term biological activity as used herein indicates the ability of the molecule to affect a living matter. Exemplary chemical activities of agents comprise formation of a covalent or electrostatic interaction. Exemplary biological activities of agents comprise production and secretion of endogenous molecules, absorption and metabolization of endogenous or exogenous molecules and activation or deactivation of genetic expression including transcription and translation of a gene of interest.

The term "antibody" includes reference to an immunoglobulin molecule that is reactive with a particular antigen. The term also includes genetically engineered forms such as chimeric antibodies (e.g., humanized murine antibodies), heteroconjugate antibodies (e.g., bispecific antibodies) and recombinant single chain Fv fragments (scFv), disulfide stabilized (dsFv) Fv fragments, or pFv fragments. The term "antibody" also includes antigen binding forms of antibodies (e.g., Fab', F(ab')2, Fab, Fv and rIgG). In the present disclosure, trastuzumab (Herceptin®) is a useful antibody, and a preferred embodiment, for the treatment of breast cancer, and for cancers that are HER2 positive.

An antibody immunologically reactive with, or "specific for," a particular antigen is a relative term and means that the antibody binds to that antigen with an affinity that is at least 10-old higher than would be observed for non-specific binding exhibited by the antibody. Thus, an antibody said to be "specific for" a given antigen may in fact selectively bind other antigens with an affinity that is 10-fold-high than it exhibits in nonspecific interactions.

The term "attach", "attached" or "attachment" as used herein, refers to connecting or uniting by a bond, link, force or tie in order to keep two or more components together, which encompasses either direct or indirect attachment such that for example where a first compound is directly bound to a second compound, and the embodiments wherein one or more intermediate compounds, and in particular molecules, are disposed between the first compound and the second compound.

Where used herein, the term "cargo" refers to the therapeutic or imaging agents being delivered (as if by "ferry") by the nanoparticles described herein In the nanoparticles herein described polyols polymers are coupled to the boronic acid polymers. The term "coupled" or "coupling" as used herein with reference to attachment between two molecules indicates an interaction forming a reversible covalent linkage. In the presence of a suitable medium, a boronic acid presented on the boronic acid polymer interact with hydroxyl groups of the polyols associated with the nanoparticle core via a rapid and reversible pair-wise covalent interaction to form boronic esters in a suitable medium. Typically, the boronic acid moieties are suitable for forming borate esters with the hydroxy groups of the nanoparticle surfaces, and for hydrolyzing under certain triggering events (e.g., changes in pH). Suitable media include water and several aqueous solutions and additional organic media identifiable by a skilled person. Typically, when contacted in an aqueous medium boronic acid polymers and polyols polymers react in a condensation reaction producing water as a side product. The boronic acid polyol interaction is generally more favorable in aqueous solutions but is also known to proceed in organic media. In addition, cyclic esters formed with 1,2 and 1,3 diols are generally more stable than their acyclic ester counterparts.

The term "brain cancer" refers to a condition where the cancer cells are present in the brain of the patient or subject, typically arising from metastases from other cancers outside the brain ("extracranial cancers"). When the brain cancer arises from the metastases of other extracranial cancers (for example, breast cancer), the methods and compositions disclosed herein allow for the use of those therapeutic agents, suitable for treating these extracranial cancers, but which are otherwise unable to pass the BBB, to deliver therapeutic levels of the metastasized brain cancers.

The tem "conjugated" as used herein indicates that one molecule has formed a covalent bond with a second molecule. The term also refers to linkages where atoms covalently bond with alternating single and multiple (e.g. double) bonds (e.g., C=C—C=C—C) and influence each other to produce electron delocalization. The person of skill in the art would be able to understand and distinguish these meanings, depending on the context.

The terms "deliver" and "delivery," as used herein, indicate the activity of affecting the spatial location of a compound, and, in particular, specifying the preferred location of a compound. Accordingly, delivering a compound in the sense of the present disclosure indicates the ability to affect positioning and movement of the compound at a certain time under a certain set of conditions, so that the compound's positioning and movement under those conditions are altered with respect to the positioning and movement that the compound would otherwise have.

In particular, delivery of a compound with respect to a reference endpoint indicates the ability to control positioning and movement of the compound so that the compound is eventually positioned on the selected reference endpoint. In an in vitro system, delivery of a compound is usually associated to a corresponding modification of the chemical and/or biological detectable properties and activities of the compound. In an in vivo system, delivery of a compound is also typically associated with modification of the pharmacokinetics and possibly pharmacodynamics of the compound.

Pharmacokinetic of a compound indicates absorption, distribution, metabolism and excretion of the compound from the system, typically provided by the body of an individual. In particular the term "absorption" indicates the process of a substance entering the body, the term "distribution" indicates the dispersion or dissemination of substances throughout the fluids and tissues of the body, the term "metabolism" indicates the irreversible transformation of parent compounds into daughter metabolites and the term "excretion" indicates the elimination of the substances from the body. If the compound is in a formulation, pharmacokinetics also comprises liberation of the compound from the formulation which indicates process of release of the compound, typically a drug, from the formulation. The term "pharmacodynamic" indicates physiological effects of a compound on the body or on microorganisms or parasites within or on the body and the mechanisms of drug action and the relationship between drug concentration and effect. A skilled person will be able to identify the techniques and procedures suitable to detect pharmacokinetics and pharmacodynamic features and properties of a compound of interest and in particular of an agent of interest such as a drug.

The described method may be used to deliver therapeutic agents to the brain of a subject, by loading the described nanoparticles with a therapeutic agent of interest prior to administration of the nanoparticle to the subject. Following delivery of the loaded nanoparticle, the targeting agent will facilitate delivery to a target cell of interest, such as a brain endothelial cell. Following internalization by the target cell, the nanoparticle will dissociate from the targeting agent. In the case of brain endothelial cells, the internalized nanoparticle will then be excreted from the cell into the interstitial space of the brain where the particle will destabilize and secrete the loaded agent, thereby delivering the agent to the brain or other target location. In some embodiments the described methods may be carried out to deliver a neurotransmitter such as serotonin or dopamine to the brain, which may be used to treat a neurological disorder. Other agents for use in treating neurological disorders may also be delivered to the brain via the described methods. Imaging agents that might not readily access the brain on their own may also be delivered using the described methods. In some embodiments the described methods may be used to deliver a nanoparticle carrying the imaging agent Cu-64 to the brain of a subject to allow for imaging. Further, the described methods may be used to deliver a combination of one or more therapeutic agents, imaging agents, or both therapeutic agents and imaging agent to the brain of a subject.

The subject may be any animal, and preferably is a mammal such as a mouse, rat, hamster, guinea pig, rabbit, cat, dog, monkey, donkey, cow, horse, pig, and the like. Most preferably, the mammal is a human. Importantly, the subject is one known to have a condition that would benefit by the treatment being administered; i.e., would benefit from delivery of the therapeutic agent to the brain of the patient by systemic means (direct injection of the therapeutic into the brain is one option, but the nanoparticle delivery systems are intended to allow for the systemic delivery of the therapeutics, and it is in this context that delivery is envisioned). That is, such a patient has a disease or condition of the brain where conventional treatments (i.e., without the use of the nanoparticles described herein) are unable to deliver sufficient quantities of the therapeutic agent systemically. This pre-recognition of the disease or condition in the subject is implicit in the definition of the subject or patient.

In some embodiments, subjects may be administered at least one of the described nanoparticles in a daily dose range of 0.01 µg to 500 mg per kg of the weight of the subject. The dose administered to the subject may also be measured in terms of total amount of at least one of the described nanoparticles administered per day. In some embodiments, a subject is administered 5 to 5000 milligrams of at least one of the described nanoparticles per dose. In some embodiments, a subject is administered up to 10 milligrams of at least one of the described nanoparticles per dose. In some embodiments, a subject is administered up to 100 milligrams of at least one of the described nanoparticles per dose. In some embodiments, a subject is administered up to 250 milligrams of at least one of the described nanoparticles per dose. In some embodiments, a subject is administered up to 500 milligrams of at least one of the described nanoparticles per dose. In some embodiments, a subject is administered up to 750 milligrams of at least one of the described nanoparticles per dose. In some embodiments, a subject is administered up to 1000 milligrams of at least one of the described nanoparticles per dose. In some embodiments, a subject is administered up to 1500 milligrams of at least one of the described nanoparticles per dose. In some embodiments, a subject is administered up to 2000 milligrams of at least one of the described nanoparticles per dose. In some embodiments, a subject is administered up to 2500 milligrams of at least one of the described nanoparticles per dose. In some embodiments, a subject is administered up to 3000 milligrams of at least one of the described nanoparticles per dose. In some embodiments, a subject is administered up to 3500 milligrams of at least one of the described nanoparticles per dose. In some embodiments, a subject is administered up to 4000 milligrams of at least one of the described nanoparticles per dose. In some embodiments, a subject is administered up to 4500 milligrams of at least one of the described nanoparticles per dose. In some embodiments, a subject is administered up to 5000 milligrams of at least one of the described nanoparticles per dose. In some embodiments, the described methods may be carried out so the nanoparticles described herein is administered to a subject weekly, bi-weekly, monthly, bi-month, semi-annually, or annually. Treatment may be initiated with smaller dosages that are less than the optimum dose followed by an increase in dosage over the course of the treatment until the optimum effect under the circumstances is reached.

When discussing the beneficial aspects of the ability of the nanoparticles to deliver the therapeutic (or any other) agent across the blood brain barrier (BBB), several criteria may be used. Given the otherwise impenetrability of the BBB to therapeutics or other agents, one such criterion is the ability of the nanoparticle(s) to deliver the pharmaceutical agent in an amount to be therapeutically useful, under conditions where the delivery of the pharmaceutical agent by itself is unsuccessful in doing so. In such embodiments, the methods may comprise the systemic administration of a plurality of nanoparticles to a subject having the neurological brain disorder (e.g., a disease such as cancer) and in need of delivery of the therapeutic agent across a blood-brain barrier to the subject's brain parenchyma, the plurality of nanoparticles being administered at a dose rate sufficient to enhance the delivery of the therapeutic agent to the brain parenchyma in therapeutically useful quantities that are higher than available using the free therapeutic agent alone. In separate embodiments, depending on the efficiency of the brain parenchyma in blocking the passage of the therapeutic agent alone, this in increase in delivery of the therapeutic agent using the nanoparticles can be at least 2 times, at least 5 time, at least 10 times, at least 100 times, or at least 1000 times higher than with the therapeutic agent alone. In some cases, the therapeutic agent may, by itself, be unable to cross the blood-brain barrier (or such delivery is imperceptively small), such that any improvement in the delivery of y such agent by means of the nanoparticle(s) disclosed herein is considered to constitute delivery.

The nanoparticles described herein may be administered orally in any acceptable dosage form such as capsules, tablets, aqueous suspensions, solutions or the like. The nanoparticles may also be administered parenterally including but not limited to: subcutaneous, intravenous, intramuscular, intra-articular, intra-synovial, and intrasternal injection or infusion techniques. Alternatively, the nanoparticles will be administered intravenously or intraperitoneally, for example, by injection. In independent exemplary embodiments, the nanoparticles are administered by intravenous and intracardiac injection.

The term "diluent" as used herein indicates a diluting agent which is issued to dilute or carry an active ingredient of a composition. Suitable diluents include any substance that can decrease the viscosity of a medicinal preparation.

The term "excipient" as used herein indicates an inactive substance used as a carrier for the active ingredients of a medication. Suitable excipients for the pharmaceutical compositions herein disclosed include any substance that enhances the ability of the body of an individual to absorb the nanoparticle. Suitable excipients also include any substance that can be used to bulk up formulations with nanoparticles to allow for convenient and accurate dosage. In addition to their use in the single-dosage quantity, excipients can be used in the manufacturing process to aid in the handling of nanoparticles. Depending on the route of administration, and form of medication, different excipients may be used. Exemplary excipients include but are not limited to antiadherents, binders, coatings disintegrants, fillers, flavors (such as sweeteners) and colors, glidants, lubricants, preservatives, sorbents.

The term "functional group" as used herein indicates specific groups of atoms within a molecular structure or portion thereof that are responsible for the characteristic chemical reactions of that structure or portion thereof. Exemplary functional groups include hydrocarbons, groups containing halogen, groups containing oxygen, groups containing nitrogen and groups containing phosphorus and sulfur all identifiable by a skilled person. Functional groups in the sense of the present disclosure include a carboxylic acid, amine, triarylphosphine, azide, acetylene, sulfonyl azide, thio acid and aldehyde. For example, a functional group able to bind a corresponding functional group in a targeting ligand can be selected to comprise the following binding partners: carboxylic acid group and amine group, azide and acetylene groups, azide and triarylphosphine group, sulfonyl azide and thio acid, and aldehyde and primary amine. Additional functional groups can be identified by a skilled person upon reading of the present disclosure. As used herein, the term "corresponding functional group" refers to a functional group that can react to another functional group. Thus, functional groups that can react with each other can be referred to as corresponding functional groups.

An end-group indicates a constitutional unit that is an extremity of a macromolecule or oligomer molecule. For example the end-group of a PET polyester may be an alcohol group or a carboxylic acid group. End groups can be used to determine molar mass. Exemplary end groups comprise —OH. —COOH, $NH_2$, and $OCH_3$, The term "leaving group," as understood by persons skilled in the art of organic synthesis, refers to a functional group susceptible to displacement by a nucleophile. Leaving groups can be anions or neutral moieties, but in either case it is crucial that the leaving group be able to stabilize the additional electron density that results from bond heterolysis. Exemplary leaving groups include halides such as chloride, bromide, and iodide, sulfonate esters such as mesylate and tosylate, water, and cationic amines.

The term "ligand" or "targeting ligand" as used in the present disclosure indicates any molecule that can be presented on the surface of a nanoparticle for the purpose of engaging a specific target, and in particular specific cellular recognition, for example by enabling cell receptor attachment of the nanoparticle. Examples of suitable ligands include, but are not limited to, vitamins (e.g. folic acid), proteins (e.g. transferrin, monoclonal antibodies), monosaccharides (e.g. galactose), peptides, and polysaccharides. In particular targeting ligands can be antibodies against certain surface cell receptors such as transferrin receptor ("TfR").

The term "nanoparticle" as used herein indicates a composite structure of nanoscale dimensions. In particular, nanoparticles are typically particles of a size in the range of from about 1 to about 1000 nm and are usually spherical although different morphologies are possible depending on the nanoparticle composition. The portion of the nanoparticle contacting an environment external to the nanoparticle is generally identified as the surface of the nanoparticle. In nanoparticles herein described, the size limitation can be restricted to two dimensions and so that nanoparticles herein described include composite structure having a diameter from about 1 to about 1000 nm, where the specific diameter depends on the nanoparticle composition and on the intended use of the nanoparticle according to the experimental design. For example, nanoparticles to be used in several therapeutic applications typically have a size of about 200 nm or below. In certain embodiments where the nanoparticles are for delivery associated to cancer treatment typically have a diameter from about 80 nm to about 120 nm.

Additional desirable properties of the nanoparticle(s), such as surface charges and steric stabilization, can also vary in view of the specific application of interest. Properties of the particles may be understood by a skilled person upon reading of the present disclosure. Nanoparticle dimensions and properties can be detected by techniques known in the art. Exemplary techniques to detect particles dimensions include but are not limited to dynamic light scattering (DLS) and nanoparticle tracking analysis (NTA) and a variety of microscopies such at transmission electron microscopy (TEM) and atomic force microscopy (AFM). Exemplary techniques to detect particle morphology include but are not limited to TEM and AFM. Exemplary techniques to detect surface charges of the nanoparticle include but are not limited to zeta potential method. Additional techniques suitable to detect other chemical properties comprise by $^1$H, $^{11}$B, $^{13}$C and $^{19}$F NMR, UV/Vis and infrared/Raman spectroscopies and fluorescence spectroscopy (when nanoparticle is used in combination with fluorescent labels) and additional techniques identifiable by a skilled person "Optional" or "optionally" means that the subsequently described circumstance may or may not occur, so that the description includes those embodiments where the circumstance occurs and instances where it does not. For example, in the phrase "at least one small molecule therapeutic agent, optionally linked to the nanoparticle core by way of an optional linker," the term "optionally linked" is interpreted to mean that the therapeutic agent may or may not be linked to the nanoparticle, and embraces both embodiments in the alternative. Similarly, the term "optional linker" embraces both embodiments, in the alternative, where the linker is either present or absent (in this case, since the optional linker refers to the linking of the therapeutic agent and the nanoparticle core, where the linker is absent, the linkage is a direct bond.

The term a "polymer" as used at least in the context of the nanoparticle core, herein embraces its generally recognized meaning and indicates a large molecule composed of repeating structural units typically connected by covalent chemical bonds. A suitable polymer may be a linear and/or branched and can take the form of a homopolymer or a co-polymer. If a co-polymer is used, the co-polymer may be a random copolymer or a branched co-polymer. Exemplary polymers comprise water-dispersible and, in particular, water-soluble polymers. For example, suitable polymers include, but are not limited to polysaccharides, polyesters, polyamides, polyethers, polycarbonates, polyacrylates, etc. For therapeutic and/or pharmaceutical uses and applications, the polymer should have a low toxicity profile and that are not toxic or cytotoxic. Suitable polymers include polymers having a molecular weight of about 500,000 or below. Suitable polymers can have a molecular weight of about 100,000 and below.

The term "polymer containing a boronic acid" or a "linker having a boronic acid" and the like as used herein indicate containing at least one boronic acid group presented for binding to a hydroxyl group of a polymer containing polyols. In particular, polymers containing boronic acids of the nanoparticles herein described include a polymer comprising in at least one structural unit an alkyl or aryl substituted boronic acid containing a carbon to boron chemical bond. Suitable boronic acid polymers comprise polymers wherein boronic acid is in a terminal structural unit or in any other suitable position to provide the resulting polymer with hydrophilic properties. In this regard, the (nitro)phenyl boronic acids, and especially nitrophenyl boronic acids, are preferred. As used herein, in the context of "(nitro)phenylboronic acid," the parenthetical "nitro" reflects separate embodiments where the phenylboronic acid moiety has at least one nitro group appended to the phenyl group (i.e., a nitrophenylboronic acid moiety) and where the phenylboronic acid group does not contain a nitro group (i.e., a phenylboronic acid moiety).

The term "polymer containing a polyol" or "polyol-containing polymer" refers to a polymer refers to a polymer presenting multiple hydroxyl functional groups. These multiple hydroxyl groups can serve to improve the hydrophilicity of the core, making the it better dispersible in aqueous media and/or may provide sites for linking the various linking groups described herein. In certain embodiments, the polymer containing a polyol suitable to form the nanoparticles here described comprise polymers presenting at least a portion of the hydroxyl functional groups for a coupling interaction with at least one boronic acid of a polymer containing a boronic acid.

In certain embodiments, the polyols comprise monomeric polyols such as pentaerythritol, ethylene glycol, glycerin, and various sugars, including mucic acid. Exemplary polymers containing polyols comprise polyesters, polyethers and polysaccharides. Exemplary suitable polyethers include but are not limited to diols, such as polyethylene glycol, polypropylene glycol, and polytetramethylene ether)glycol. Exemplary, suitable polysaccharides include but are not limited to cyclodextrins, starch, glycogen, cellulose, chitin and β-Glucans. Exemplary, suitable polyesters include but are not limited to polycarbonate, polybutyrate and polyethylene terephthalate, all terminated with hydroxyl end groups. Exemplary polymers containing polyols comprise polymers of about 500,000 or less molecular weight and in particular from about 300 to about 100,000.

The term "polypeptide" as used herein indicates an organic linear, circular, or branched polymer composed of two or more amino acid monomers and/or analogs thereof. The term "polypeptide" includes amino acid polymers of any length including full length proteins and peptides, as well as analogs and fragments thereof. A polypeptide of three or more amino acids is also called a protein oligomer, peptide or oligopeptide. In particular, the terms "peptide" and "oligopeptide" usually indicate a polypeptide with less than 50 amino acid monomers. As used herein the term "amino acid", "amino acidic monomer", or "amino acid residue" refers to any of the twenty naturally occurring amino acids, ion-natural amino acids, and artificial amino acids and includes both D an L optical isomers. In particular, non-natural amino acids include D-stereoisomers of naturally occurring amino acids (these including useful ligand building blocks because they are not susceptible to enzymatic degradation). The term "artificial amino acids" indicate molecules that can be readily coupled together using standard amino acid coupling chemistry, but with molecular structures that do not resemble the naturally occurring amino acids. The term "amino acid analog" refers to an amino acid in which one or more individual atoms have been replaced, either with a different atom, isotope, or with a different functional group but is otherwise identical to original amino acid from which the analog is derived. All of these amino acids can be synthetically incorporated into a peptide or polypeptide using standard amino acid coupling chemistries. The term "polypeptide" as used herein includes polymers comprising one or more monomer or building blocks other than an amino acid monomer. The terms monomer, subunit, or building blocks indicate chemical compounds that under appropriate conditions can become chemically bonded to another monomer of the same or different chemical nature to form a polymer the term "poly peptide" is further intended to comprise a polymer wherein one or more of the building blocks is covalently bound to another by a chemical bond other than amide or peptide bond.

The term "protein" as used herein indicates a polypeptide with a particular secondary and tertiary structure that car participate in, but not limited to, interactions with other biomolecules including other proteins, DNA, RNA, lipids, metabolites, hormones, chemokines, and small molecules Exemplary proteins herein described are antibodies. The term protein embraces fusion proteins.

The term "prevent" as used herein to describe the action of inhibiting cell proliferation or the growth of tumors, or ameliorating the symptoms, prolonging the survival of, or otherwise mitigating the undesirable effects of the disease for which the patient is being treated.

The distinction between the terms "small molecule therapeutic" and "large molecule therapeutic" should be apparent to a person of skill in the art, as based on molecular weight of the molecule. In certain embodiments, the demarcation may be defined as a molecular weight of about 600 Da, 800 Da, 1000 Da, or 1200 Da. In the context of "small molecules capable of passing the blood brain barrier," unless the molecule is specifically known to be incapable of passing the blood brain barrier, this is normally defined by a "Rule of Five," typically attributed to Lipinski, that describes the physical parameters seen as necessary or essential for a small molecule to pass. According to this Rule, a good absorption and permeability is likely if:

Molecular weight is ≤600;

Oil/water distribution coefficient (Log P) is ≤5;

Hydrogen bond donors≤3-5 (expressed as the sum of OHs and NHs);

Hydrogen bond acceptor≤7-10 (expressed as the sum of Ns and Os); and

Number of rotatable bonds≤5-10.

For the purposes of this disclosure, a small molecule therapeutic will be considered capable of passing the blood brain barrier without the disclosed nanoparticle systems if it is otherwise known to pass or meets these criteria. Likewise, unless otherwise stated, a small molecule will be deemed incapable of passing through the blood brain barrier to deliver therapeutically effect amounts without the nanoparticles set forth herein, if it does not satisfy these criteria. Against this context, a review by H. Pajouhesh, et al., "Medicinal Chemical Properties of Successful Central Nervous System Drugs" *NeuroRx,* 2005 October; 2(4) 541-553, which is incorporated by reference herein for its teaching in this regard, based on literature surveys concluded that successful CNS drugs had:

Molecular weight—preferably below a 400 to 600-Da range;

Oil/water distribution coefficient (Log P)—preferably in the range of 1.5-2.7;

Hydrogen bond donors and acceptors—collectively (O+N)=4.32:2.12 hydrogen bond acceptors and 1.5 hydrogen bond donors;

PSA (polar surface area) (defined as the surface area (A2) occupied by nitrogen and oxygen atoms and the polar hydrogens attached to them and is strongly reflective of hydrogen bonding capacity and polarity—less than 60-70 Å$^2$ Aqueous solubility>60 µg/ml;

Number of rotatable bonds—less than 5.

The number of (OH+NH) bonds (≤1.5 to 2), number of (O+N) bonds (≤4.3 to 6), hydrogen bond acceptors (≤2.5 to 4), and rotatable bonds (≤4.7 to 7) appeared to distinguish CNS (74) and gastrointestinal-metabolic (38) drugs marketed between 1983 and 2002, suggesting these parameters are most important. Generally, marketed CNS drugs tend to smaller with a more compact and less flexible structure, the surface having fewer polar groups able to function as hydrogen bond donors and acceptors and compared to the total surface area, the PSA is reduced. These can give further definition to the small molecules capable of passing the blood brain barrier.

The term "substantially free" as in "where the nanoparticle core and/or surface is substantially free of cationic mucic-acid containing polymer (cMAP)" refers to a composition in which the core or surface composition contains less than 3 mol % of the cMAP polymer, preferably less than 1%, and more preferably no cMAP polymer. Unless otherwise indicated, the term refers to the absence of cMAP polymer.

The term "target" as used herein indicates a biological system of interest including organs, tissues, or any portion thereof and may include in vitro or in vivo biological systems or any portion thereof. In certain embodiments, the target is a tumor or cancer cells within the brain itself.

As used herein, the terms "therapeutic agent" and "chemotherapeutic agent" are intended to mean a compound that, when present in a therapeutically effective amount, produces a desired therapeutic effect on a patient; for example, utilized to treat, combat, ameliorate, prevent or improve an unwanted condition or disease of a patient or subject. In the case of cancer, this includes stopping the progression of the cancer and/or a reduction in the presence of corresponding tumors or cancer cells. Such inhibition may occur for example, and without limitation, via a direct interaction, and/or through a competitive interaction, or via an allosteric interaction with a corresponding receptor. The term "[chemo]therapeutic agent" is intended to embrace the separate embodiments of the general term "therapeutic agent" and the more specific "chemotherapeutic agent," the latter term generally associated with cytotoxic agents for use in chemotherapy for cancer. More generally, the use of brackets or parentheses, in this way, is intended to refer to separate embodiments where the bracketed or parenthetical text is both present and absent.

In addition to the therapeutic agents disclosed elsewhere herein, the term more generally encompasses any lipophilic or hydrophilic, synthetic or naturally occurring biologically active therapeutic agent including those known in the art. The Merck Index, An Encyclopedia of Chemicals, Drugs, and Biologicals, 13th Edition, 2001, Merck and Co., Inc., Whitehouse Station, N.J. Examples of such therapeutic agents include, but are not limited to, small molecule pharmaceuticals, antibiotics, steroids, polynucleotides (e.g. genomic DNA, cDNA, mRNA, siRNA, shRNA, miRNA, antisense oligonucleotides, viruses, and chimeric polynucleotides), plasmids, peptides, peptide fragments, small molecules (e.g. doxorubicin), chelating agents (e.g. desferrioxamine, ethylenediaminetetraacetic acid (EDTA), natural products (e.g. Taxol, Amphotericin), and other biologically active macromolecules such as, for example, proteins and enzymes. See also U.S. Pat. No. 6,048,736 which lists active agents (therapeutic agents) that can be used as therapeutic agent with nanoparticles herein described Small molecule therapeutic agents may not only be the therapeutic agent within the composite particle but, in an additional embodiment, may be covalently bound to a polymer in the composite. In several embodiments, the covalent bond is reversible (e.g. through a prodrug form or biodegradable linkage such as a disulfide) and provides another way of delivering the therapeutic agent. In several embodiments therapeutic agent that can be delivered with the nanoparticles herein described include chemotherapeutics such as epothilones, camptothecin-based drugs, taxol, or a nucleic acid such as a plasmid, siRNA, sbRNA, miRNA, antisense oligonucleotides aptamers or their combination, and additional drugs identifiable by a skilled person upon reading of the present disclosure.

A "therapeutically effective amount" or "effective amount" of a composition is a predetermined amount calculated to achieve the desired effect. The activity contemplated by the present methods includes both medical therapeutic and/or prophylactic treatment, as appropriate. As used herein, "therapeutically effective amount" refers to the amount of active compound or pharmaceutical agent that elicits a biological or medicinal response in a tissue, system, animal, individual or human that is being sought by a researcher, veterinarian, medical doctor or other clinician, which includes one or more of the following as specified in the particular methodology: (1) preventing the disease; for example, preventing a disease, condition or disorder in an individual that may be predisposed to the disease, condition or disorder but does not yet experience or display the pathology or symptomatology of the disease, (2) inhibiting the disease; for example, inhibiting a disease, condition or disorder in an individual that is experiencing or displaying the pathology or symptomatology of the disease, condition or disorder (i.e., arresting further development of the pathology and/or symptomatology), and (3) ameliorating the disease; for example, ameliorating a disease, condition or disorder in an individual that is experiencing or displaying the pathology or symptomatology of the disease, condition or disorder (i.e., reducing the severity of the pathology and/or symptomatology).

As used herein, the term "transferrin" (abbreviated "Tf") is meant to encompass variants and isoforms of the protein, as well as fragments of the protein capable of binding to the transferrin receptor ("TfR"). For example, the term would include holo-transferrin as well as transferrin itself.

The terms "treat," "treated," or "treating" as used herein refers to both therapeutic treatment and prophylactic or preventative measures, wherein the object is to prevent or slow down (lessen) an undesired physiological condition, disorder or disease, or to obtain beneficial or desired clinical results. For the purposes of this invention, beneficial or desired clinical results include, but are not limited to, diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment includes eliciting a clinically significant response with or without excessive levels of side effects.

The term "vehicle" as used herein indicates any of various media acting usually as solvents, carriers, binders, excipients or diluents for a nanoparticle comprised in the composition as an active ingredient.

General Embodiments of the Present Disclosure

The following listing of embodiments is intended to complement, rather than displace or supersede, the previous descriptions.

Embodiment 1. A polymer, polymer conjugate, or nanoparticle composition comprising:
a polymer or nanoparticle core to which is bonded
(a) at least one targeting agent, the targeting agent comprising a ligand attached to an external surface of the nanoparticle core by a linker;
the ligand having an affinity for binding to a receptor expressed by endothelial cells of the blood-brain barrier; and
the linker being cleavable when subject to conditions inside an endothelial cell of the blood-brain barrier, wherein the cleavage comprises hydrolysis, chemical reduction, or enzymatic cleavage of the linker;
and one or both of
(b) at least one small molecule therapeutic agent, optionally linked to the nanoparticle core by way of an optional linker; and/or
(c) at least one large molecule therapeutic agent, linked to the nanoparticle by way of an optional linker;
wherein the nanoparticle comprises polyol-containing polymer, such as a mucic acid-containing polymer (MAP) or a cationic mucic acid polymer (cMAP), a peptide, a poly(lactic-co-glycolic acid) (PLGA) polymer, chitosan, a synthetic polymer such as a polyamide, a polycarbonate, a polyethylene, a polyethyleneimine, gold, and/or iron oxide, or any combination thereof, and further wherein
the large molecule therapeutic agent, when present, and the targeting agent comprise different chemical entities. Additionally, or alternatively, in certain independent Aspects of this Embodiment, the presence of a cationic mucic acid polymer (cMAP) is specifically excluded.

Additionally, or alternatively, in certain independent Aspects of this Embodiment, the composition is or can be independently characterized as a polymer (i.e., without regard to any specific second order structure) comprising the single polymer or more polymers, for example a mucic acid polymer linked to a small molecule therapeutic agent.

Additionally, or alternatively, in certain independent Aspects of this Embodiment, the composition is or can be characterized as a polymer chain (i.e., without regard to any specific second order structure) comprising the coupling of two or more polymers, for example a mucic acid polymer and a (nitro-boronic acid polymer).

Additionally, or alternatively, in certain independent Aspects of this Embodiment, the composition is or can be characterized as a nanoparticle or population of nanoparticles.

Additionally, or alternatively, in certain independent Aspects of this Embodiment, the core is independently characterized simply as a polymer. In other independent Aspects of this Embodiment, the core is independently characterized as a nanoparticle.

Additionally, or alternatively, in certain independent Aspects of this Embodiment, the polymer, polymer conjugate, or nanoparticle composition comprises the polymer or nanoparticle core to which is bonded at least one targeting agent and the at least one small molecule therapeutic agent.

Additionally, or alternatively, in other independent Aspects of this Embodiment, the polymer, polymer conjugate, or nanoparticle composition comprises the polymer or nanoparticle core to which is bonded at least one targeting agent and the at least one large molecule therapeutic agent.

Additionally, or alternatively, in other independent Aspects of this Embodiment, the polymer, polymer conjugate, or nanoparticle composition comprises the polymer or nanoparticle core to which is bonded at least one targeting agent, the at least one small molecule therapeutic agent, and the at least one large molecule therapeutic agent.

Additionally, or alternatively, in other independent Aspects of this Embodiment, the linker comprises a polyethylene glycol (PEG) polymer moiety conjugated to the surface of the nanoparticle core by a pH sensitive linkage selected from the group consisting of an acetal, a borate ester, a carbonate, a carboxylic acid ester, a diamino ketal, a disulfide, a hydrazone, an imine, a ketal, an orthoester, or a peptide linkage.

Additionally, or alternatively, in other independent Aspects of this Embodiment, the linker comprises, when the pH sensitive linkage is carboxylic acid ester linkage, the surface of the nanoparticle core comprises poly(lactic-co-glycolic acid) (PLGA) polymers, wherein the linker is dissociable when subject to pH conditions inside an endothelial cell of the blood-brain barrier.

Additionally, or alternatively, in other independent Aspects of this Embodiment, the linker comprises a polyethylene glycol (PEG) polymer moiety conjugated to the surface of the nanoparticle core by a peptide linkage, wherein the peptide linkage can be enzymatically cleaved to cause dissociation of the ligand from the nanoparticle when the nanoparticle is inside a brain endothelial cell.

Additionally, or alternatively, in other independent Aspects of this Embodiment, one or both of the therapeutic agents characterized as small molecule therapeutic agent and the large molecule therapeutic agent is a small molecule chemotherapeutic agent and large molecule chemotherapeutic agent, respectively.

Additionally, or alternatively, in other independent Aspects of this Embodiment, the polymer, polymer conjugate, or nanoparticle composition comprises a structure as described in any one of the structures described in U.S. Pat. No. 8,557,292; 8,746,999; 8,968,714; 9,186,327; 9,334,367; 9,610,355; or 9,913,911 (CIT-5200); PCT application PCT/US2009/053620 (CIT-5200); U.S. Pat. No. 9,468,681; PCT application PCT/US2013/028663 (CIT-6456); U.S. Pat. No. 9,132,097; PCT application PCT/US2013/028681 (CIT-6455); U.S. patent application Ser. No. 14/120,309; PCT application PCT/US2014/000099 (CIT-6566); U.S. patent application Ser. No. 15/180,201; or PCT application PCT/US2016/037166 (CIT-7222). These references are incorporated by reference herein for all purposes, but at least for the descriptions of the nanoparticles and uses thereof described therein.

Embodiment 2. The polymer, polymer conjugate, or nanoparticle composition of Embodiment 1, wherein the polymer or nanoparticle core comprises, consists essentially of, or consists of mucic acid polymer (MAP), a cationic mucic acid polymer (cMAP), a poly(lactic-co-glycolic acid) (PLGA), chitosan, polyethyleneimine, polysaccharide, polyester, polyamide, polyether, polycarbonate, polyacrylate, iron oxide, or gold. Each of these materials constitute independent Aspects of this Embodiment.

Additionally, or alternatively, other water-dispersible and in particular water-soluble polymers may be considered for this purpose. For therapeutic and/or pharmaceutical uses and applications, the polymer should have a low toxicity profile and in particular that are not toxic or cytotoxic. Additionally, or alternatively, such polymers include those having a molecular weight of about 500,000 or below. In particular, suitable polymers can have a molecular weight of about 100,000 and below.

Further, in additional or alternative Aspects of this Embodiment, the polymer or nanoparticle core by itself (i.e., without the targeting ligand, or small or large molecule therapeutic compounds), as further characterized herein, is considered an independent aspect of this Embodiment.

Embodiment 3. The polymer, polymer conjugate, or nanoparticle composition of Embodiment 1 or 2, wherein the polymer or nanoparticle core comprises, consists essentially of, or consists of a polyol-containing polymer, preferably a sugar-containing polymer, for example, a polymer derived from glucose, fructose, mannitol, mucic acid, sucrose, galactose, sorbitol. xylose or galactose, more preferably from mucic acid. Additionally, or alternatively, in certain Aspects of this Embodiment, the polyol-containing polymer of the polymer, polymer conjugate, or nanoparticle composition further comprises dihydroxy, hydroxy-amine, and/or diamine linkages between the polyol moieties, wherein the dihydroxy, hydroxy-amine, and/or diamine linkages independently comprise 1 to 6 carbon atoms between the respective hydroxy and amine functional groups.

Embodiment 4. The polymer, polymer conjugate, or nanoparticle composition of any one of Embodiments 1 to 3, wherein the polymer or nanoparticle core is charge neutral and/or negatively charged. In certain Aspects of this Embodiment, the polymer or nanoparticle core contains no cationic moieties (e.g., does not contain any cationic mucic acid polymers (cMAP) or polymer portions.

Embodiment 5. The polymer, polymer conjugate, or nanoparticle composition of any one of Embodiments 1 to 3, wherein the polymer or nanoparticle core comprises at least one cationic and/or at least one anionic moiety. Additionally, or alternatively, in independent Aspects of this Embodiment, the polymer or nanoparticle core contains a net cationic charge, a net anionic charge, or is charge-balanced neutral.

In certain independent Aspects within this Embodiment, a net cationic charge may be provided by the incorporation of amidines, quaternary ammoniums, primary, secondary, or tertiary amine groups (protonated below their pKa's), and imidazolium groups. In certain independent Aspects within this Embodiment, a net anionic charge may be provided by the incorporation of functional groups including sulfonates, nitrates, carboxylates, and phosphonates.

Embodiment 6. The polymer, polymer conjugate, or nanoparticle composition of any one of Embodiments 1 to 5, wherein the polymer or nanoparticle core independently comprises units of the formula:

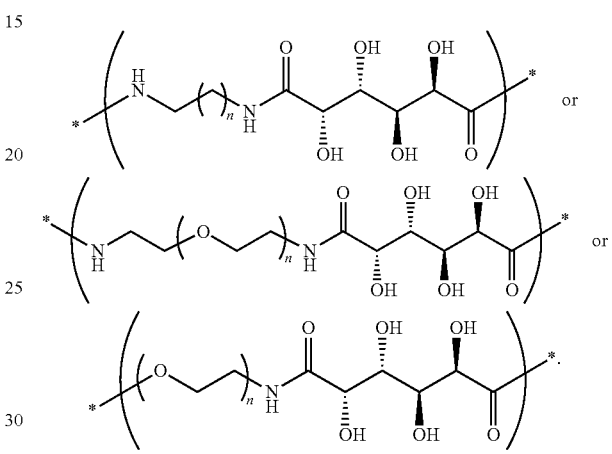

Embodiment 7. The polymer, polymer conjugate, or nanoparticle composition of any one of Embodiments 1 to 6, wherein the polymer or nanoparticle core comprises a polymer containing a polyol, wherein the polymer containing the polyol is derived from the coupling of a compound of Formula A with a compound of Formula B; wherein the compound of Formula A is:

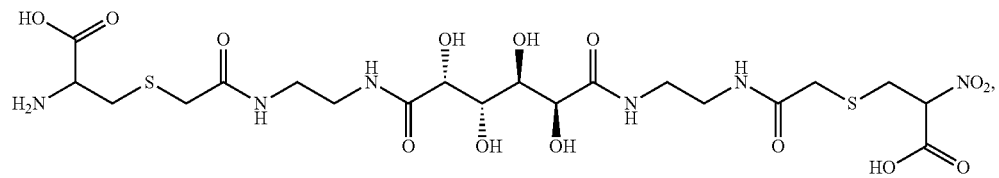

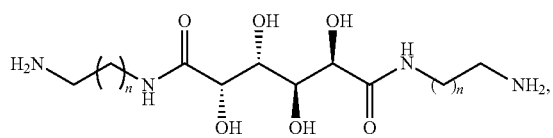

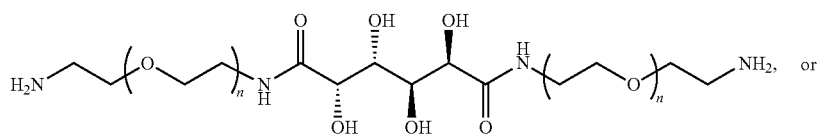

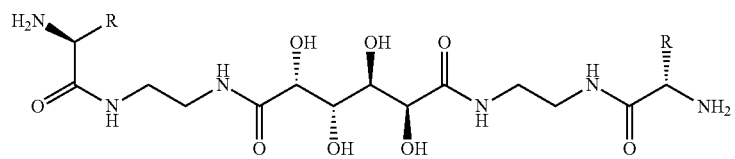

wherein n is a number from 1 to 20; and
R is a functional group residue (e.g., —COOH, —NH$_2$, —OH) corresponding to that of an amino acid containing a third functional group, for example arginine (R is CH$_2$CH$_2$CH$_2$NHC(NH$_2$)$_2$+), histidine (R is CH$_2$-imidazolyl), lysine (R is CH$_2$—CH$_2$—CH$_2$—CH$_2$—NH$_2$), aspartic acid (R is CH$_2$—COOH), glutamic acid (R is CH$_2$—CH$_2$—COOH), serine (R is CH$_2$—OH), threonine (R is CH(OH)(CH$_3$)) asparagine (R is CH$_2$—C(O)NH$_2$), glutamine (R is CH$_2$—CH$_2$—C(O)NH$_2$), tyrosine (R is CH$_2$-Ph-OH), tryptophan (R is CH$_2$-indolyl), or a salt thereof, and
the compound of Formula B is:

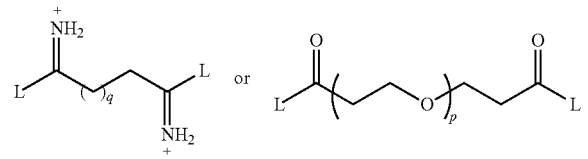

in which
q is a number from 1 to 20;
p is a number from 20 to 200; and
L is a leaving group.
Additionally, or alternatively, in independent Aspects of this Embodiment, the compound of Formula B is:

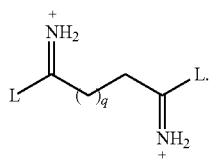

Additionally, or alternatively, in some Aspects of this Embodiment, the compound of Formula B specifically excludes:

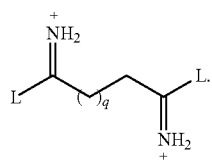

Additionally, or alternatively, in independent Aspects of this Embodiment, the compound of Formula B is:

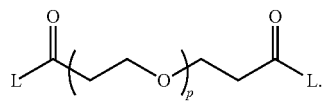

Embodiment 8. The polymer, polymer conjugate, or nanoparticle composition of any one of Embodiments 1 to 7, wherein the polymer or nanoparticle core independently comprises units of the formula:

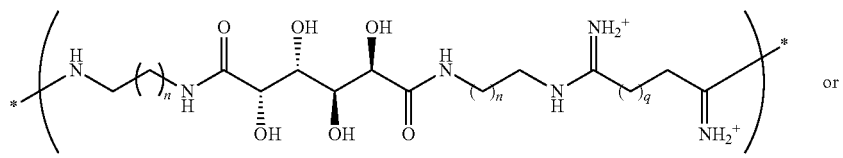

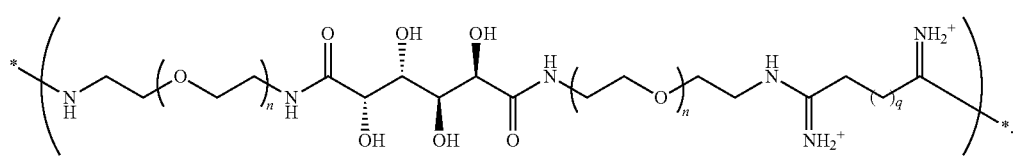

Embodiment 9. The polymer, polymer conjugate, or nanoparticle composition of any one of Embodiments 1 to 8, wherein the polymer or nanoparticle core independently comprises units of the formula:

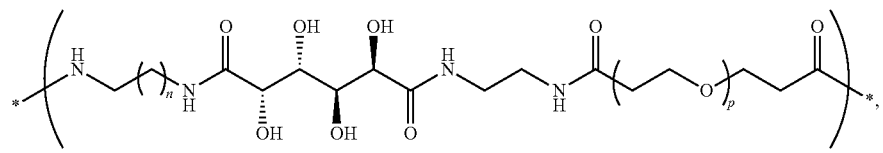

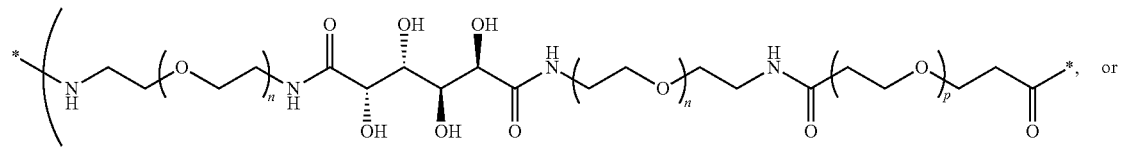

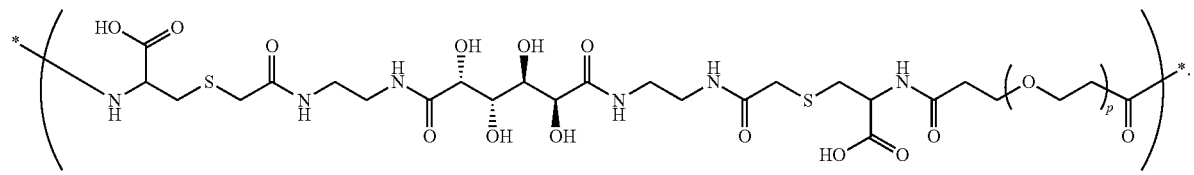

Additionally, or alternatively, in independent Aspects of any one of Embodiments 7 to 9, q is a number from 1 to 20 and p is a number from 20 to 200. Additionally, or alternatively, in other independent Aspects any one of Embodiments 7 to 9, n is 1 and q is 1.

Embodiment 10. The polymer, polymer conjugate, or nanoparticle composition of any one of Embodiments 1 to 9, wherein the polymer or nanoparticle core independently comprises units derived from the coupling of:

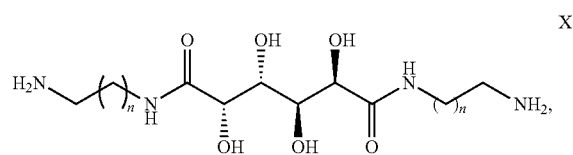

X

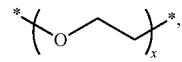

where n is a number from 1 to 20 with a trifunctional amino acid, for example including arginine, histidine, lysine, aspartic acid, glutamic acid, serine, threonine, asparagine, or glutamine, or a moiety derived therefrom, preferably from aspartic acid, or a moiety derived therefrom.

Embodiment 11. The polymer, polymer conjugate, or nanoparticle composition of any one of Embodiments 1 to 10, wherein the polymer or nanoparticle core polymer comprises a polyol and a polyethylene oxide linkage:

where x is in a range of from 15 to 100, preferably 20 to 85.

Embodiment 12. The polymer, polymer conjugate, or nanoparticle composition of any one of Embodiments 1 to 11, wherein the polymer or nanoparticle core polymer comprises a polyol structure:

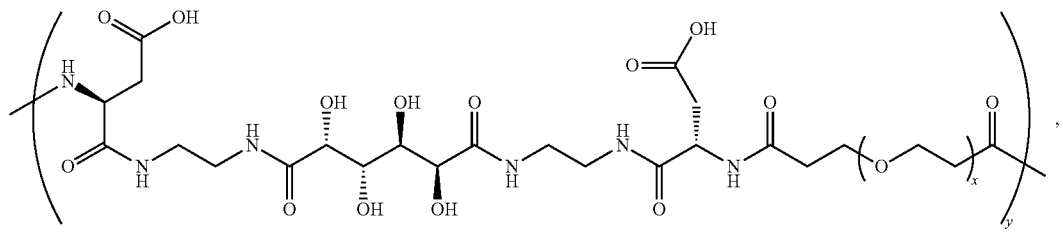

where y is in a range of from 10 to 25, preferably 15 to 25, more preferably about 20, or more broadly:

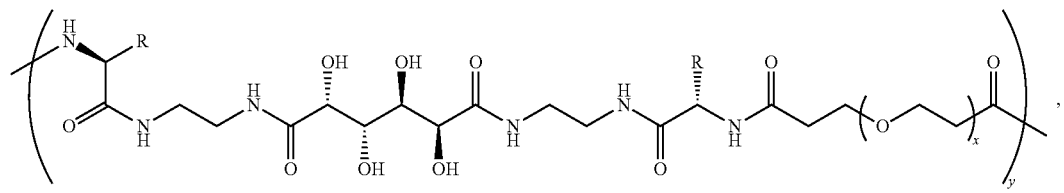

where R is a functional group residue (containing, e.g., a —COOH, —NH₂, —OH residue) corresponding to that of an amino acid containing a third functional group, for example arginine (R is CH₂CH₂CH₂NHC(NH₂)₂+), histidine (R is CH₂-imidazolyl), lysine (R is CH₂—CH₂—CH₂—CH₂—NH₂), aspartic acid (R is CH₂—COOH), glutamic acid (R is CH₂—CH₂—COOH), serine (R is CH₂—OH), threonine (R is CH(OH)(CH₃)) asparagine (R is CH₂—C(O)NH₂), glutamine (R is CH₂—CH₂—C(O)NH₂), tyrosine (R is CH₂-Ph-OH), tryptophan (R is CH₂-indolyl), or a salt thereof.

Additionally, or alternatively, in certain Aspects of this Embodiment, R is independently linked to one or more of the targeting agent, the small molecule [chemo]therapeutic agent, and/or the large molecule [chemo]therapeutic agent.

Embodiment 13. The polymer, polymer conjugate, or nanoparticle composition of any one of Embodiments 1 to 12, wherein the polymer or nanoparticle core copolymer comprises residues of lactic acid, glycolic acid, or a combination thereof. In certain additional or alternative Aspects of this Embodiment, the residues of the lactic acid, glycolic acid, or a combination thereof are arranged as polymers or co-polymers of these materials. Additionally, or alternatively, the polymer or nanoparticle core copolymer consists of these polymers or co-polymers. Additionally, or alternatively, the polymer or nanoparticle core copolymer comprise one or more sugar polyol (including mucic acid), lactic acid, and/or glycolic acid residues. That is, in some Aspects of this Embodiment, poly(lactic-co-glycolic acid) (PLGA) core is further modified to incorporate sugars having suitable hydroxyl groups to allow the particle to be conjugated to a boronic acid-containing targeting agent.

Embodiment 14. The polymer, polymer conjugate, or nanoparticle composition of any one of Embodiments 1 to 13, wherein the polymer or nanoparticle core polymer comprises alternating charged and uncharged segments comprising one or more of the following structural units of Formula (I) or Formula (II) or Formula (III):

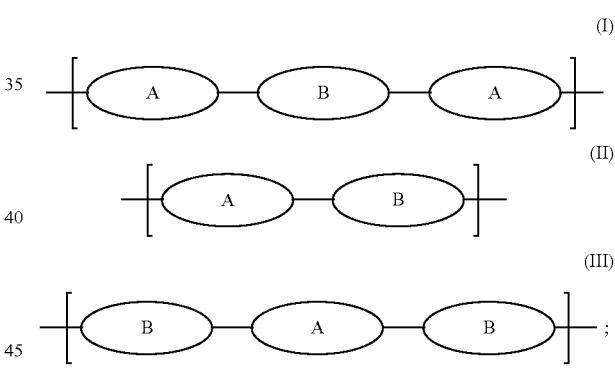

wherein
A is an uncharged segment comprising polyalkylene glycol;
B is a cationically charged segment comprising at least one polyhydroxy linkage comprising at least one pair of vicinal diols. In certain subset embodiments, A and B independently have number average molecular weights in a range 500 Da to about 5000 Da, greater than 5000 da to about 10 kDa, greater than 10 kDa to about 20 kDa, greater than 20 kDa to about 30 kDa, greater than 30 kDa to about 40 kDa, greater than greater than 40 kDa to about 50 kDa, or any combination thereof. In other subsets, either A or B, or both A and B have a number average molecular weight in a range of greater than 5000 Da to about 50,000 Da.

Embodiment 15. The polymer, polymer conjugate, or nanoparticle composition of Embodiment 14, wherein A is or comprises polyethylene glycol and an appropriate linking group.

Embodiment 16. The polymer, polymer conjugate, or nanoparticle composition of Embodiment 15 or 15, wherein the polyalkylene glycol has a nominal number averaged molecular weight in a range of from about 500 Daltons to about 50,000 Daltons. Additionally, or alternatively, in certain Aspects of this Embodiment, the polyalkylene glycol has a nominal number averaged molecular weight in a range of from about 500 Da to about 1 kDa, greater than 1 kDa to about 5 kDa, greater than 5 kDa to about 10 kDa, greater than 10 kDa to about 15 kDa, greater than 15 kDa to about 20 kDa, greater than 20 kDa to about 30 kDa, greater than 30 kDa to about 40 kDa, greater than 40 kDa to about 50 kDa, or any combination of two or more of these ranges.

Embodiment 17. The polymer, polymer conjugate, or nanoparticle composition of any one of Embodiments 14 to 16, where B is a cationically charged segment comprising at least one polyhydroxy sugar linkage comprising at least one pair of vicinal diols.

Embodiment 18. The polymer, polymer conjugate, or nanoparticle composition of any one of Embodiments 14 to 17, wherein B comprises at least one repeating subunit comprising a structure:
Note that the structure designated as

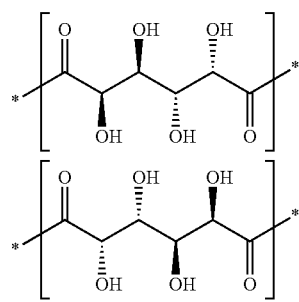

is functionally equivalent to that presented immediately preceding and this representation is intended to refer to both.

Embodiment 19. The polymer, polymer conjugate, or nanoparticle composition of any one of Embodiments 14 to 18, wherein B further comprises at least one repeating subunit comprising a structure:

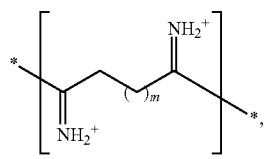

wherein m is 1, 2, 3, 4, 5, 6, 7, 8, 9, or 10, preferably 4-6 or 5.

Embodiment 20. The polymer, polymer conjugate, or nanoparticle composition of any one of Embodiments 14 to 19, wherein B comprises at least one repeating subunit comprising cMAP, whose subunit structure is represented as:

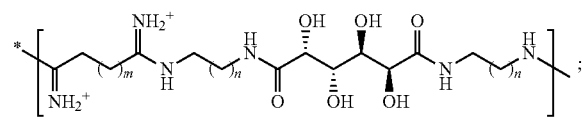

wherein
m is independently at each occurrence 1, 2, 3, 4, 5, 6, 7, 8, 9, or 10, preferably 4-6 or 5; and
n is independently at each occurrence 1, 2, 3, 4, or 5. In other related embodiments, m and n can be larger, for example to about 10.

Embodiment 21. The polymer, polymer conjugate, or nanoparticle composition of any one of Embodiments 14 to 20, described by a structure:

wherein
Chain A is

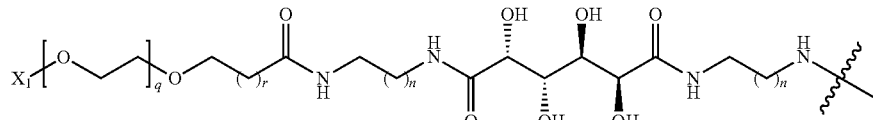

Chain B is

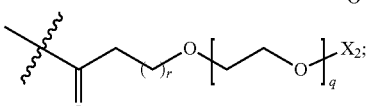

cMAP is

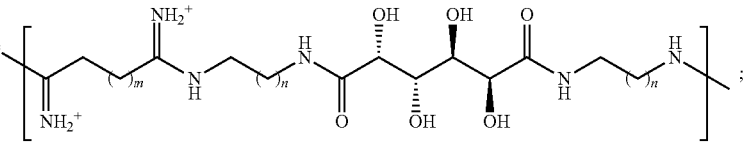

p and q are sufficient to provide a number average molecular weight for the subunits comprising cMAP and PEG, respectively, independently in a range of from about 500 Da to about 50,000 Da;

m is independently at each occurrence 1, 2, 3, 4, 5, 6, 7, 8, 9, or 10, preferably 4-6 or 5;

n and r are independently at each occurrence 0, 1, 2, 3, 4, or 5; and $X_1$ and $X_2$ are independently at each occurrence $C_{1-6}$ alkyl, optionally substituted with —OH, —COOH, —C(=O)O(alkyl), —C(=O)O(aryl), —NH$_2$, —NH(alkyl), —N(alkyl)$_2$, or a salt or protected analog thereof.

Note that, to meet the molecular weight restrictions, the numeric values for p corresponds to a range of from about 1 to about 100, preferably from about 10 to about 100, and the numeric values for q corresponds to as range from about 12 to about 1200. In subsets of these embodiments, q can also be in a range of from about 100 to about 500. In certain subsets of this Embodiment, p and q are sufficient to provide a number average molecular weight for the subunits comprising cMAP and PEG, respectively, independently in a range of from about 500 Da to about 1000 Da, greater than 1000 Da to about 5000 Da, greater than 5000 Da to about 10,000 Da, greater than 10,000 to about 25,000 Da, greater than 25,000 Da to about 50,000 Da, or any combination of two or more of these ranges, as well as the corresponding numeric values for these MW$_n$ ranges. In other subsets of this Embodiment, $X_1$ and $X_2$ are independently —(CH$_2$)$_{1-4}$—COOH and —(CH$_2$)$_{1-4}$—NH$_2$.

Embodiment 22. The polymer, polymer conjugate, or nanoparticle composition of any one of Embodiments 14 to 21, described by a structure:

p and q are sufficient to provide a number average molecular weight for the subunits comprising cMAP and PEG, respectively, independently in a range of from about 500 Da to about 50,000 Da;

m is independently at each occurrence 1, 2, 3, 4, 5, 6, 7, 8, 9, or 10, preferably 4-6 or 5;

n and r are independently at each occurrence 0, 1, 2, 3, 4, or 5;

z is equal to or greater than 1 (up to about 2, 4, 6, 8, or 10); and $X_2$ is independently at each occurrence $C_{1-6}$ alkyl, optionally substituted with —OH, —COOH, —C(=O)O(alkyl), —C(=O)O(aryl), —NH$_2$, —NH(alkyl), —N(alkyl)$_2$, or a salt or protected analog thereof, and.

$X_3$ is —OH, —COOH, —C(=O)O(alkyl), —C(=O)O(aryl), —NH$_2$, —NH(alkyl), —N(alkyl)$_2$, or a salt or protected analog thereof.

Again, as in Embodiment 21, to meet the molecular weight restrictions, the numeric values for p corresponds to a range of from about 1 to about 100, preferably from about 10 to about 100, and the numeric values for q corresponds to as range from about 12 to about 1200. In subsets of these embodiments, q can also be in a range of from about 100 to about 500. In certain subsets of this Embodiment, p and q are sufficient to provide a number average molecular weight for the subunits comprising cMAP and PEG, respectively, independently in a range of from about 500 Da to about 1000 Da, greater than 1000 Da to about 5000 Da, greater than 5000 Da to about 10,000 Da, greater than 10,000 to about 25,000 Da,

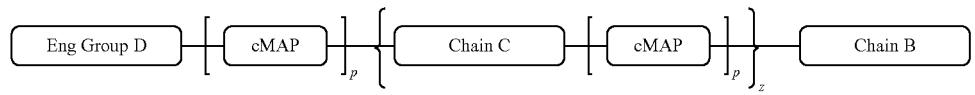

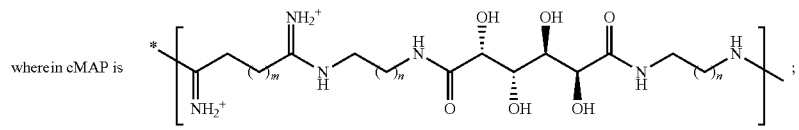

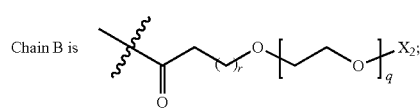

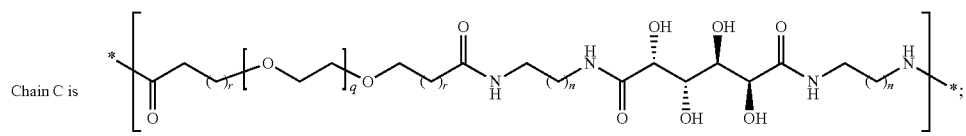

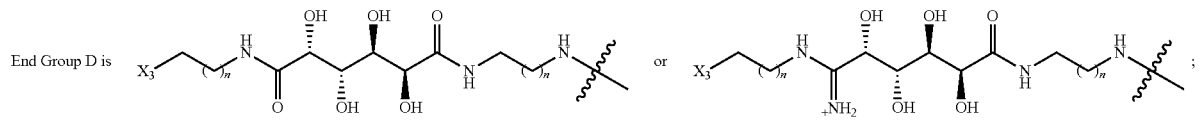

greater than 25,000 Da to about 50,000 Da, or any combination of two or more of these ranges, as well as the corresponding numeric values for these $MW_n$ ranges. In other subsets of this Embodiment, $X_1$ and $X_2$ are independently —$(CH_2)_{1-4}$—COOH and —$(CH_2)_{1-4}$—$NH_2$ Embodiment 23. The polymer, polymer conjugate, or nanoparticle composition of any one of Embodiments 13 to 21, described by a structure:

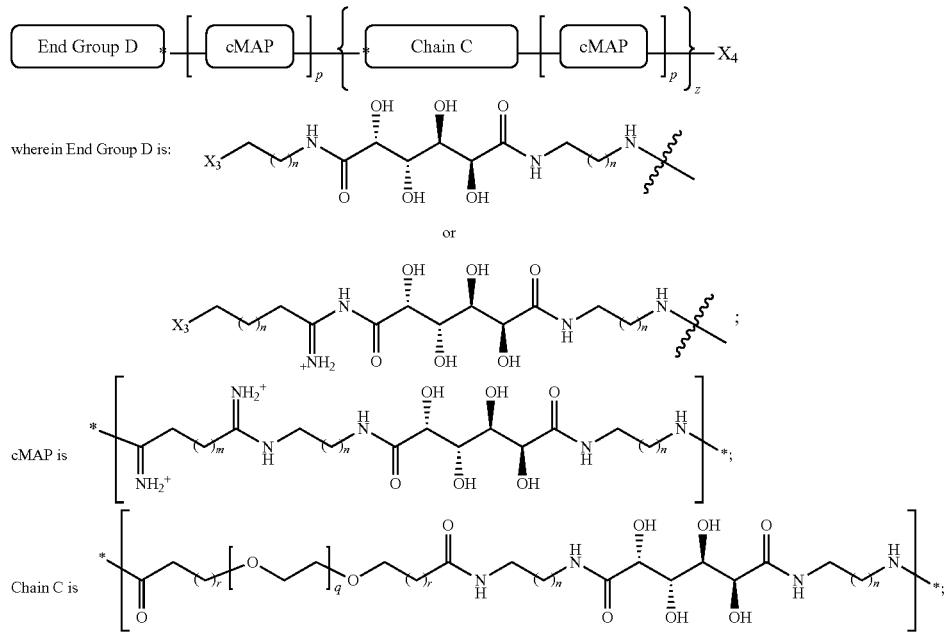

p and q are sufficient to provide a number average molecular weight for the subunits comprising cMAP and PEG, respectively, independently in a range of from about 500 Da to about 50,000 Da, preferably from about 1000 Da to about 5000 Da;

m is independently at each occurrence 1, 2, 3, 4, 5, 6, 7, 8, 9, or 10, preferably 4-6 or 5;

n and r are independently at each occurrence 0, 1, 2, 3, 4, or 5;

z is equal to or greater than 1 (up to about 2, 4, 6, 8, or 10); and $X_3$ and $X_4$ are independently at each occurrence —OH, —COOH, —C(=O)O(alkyl), —C(=O)O(aryl), —$NH_2$, —NH(alkyl), —N(alkyl)$_2$, or a salt or protected analog thereof.

Again, as in Embodiments 21 and 22, to meet the molecular weight restrictions, the numeric values for p corresponds to a range of from about 1 to about 100, preferably from about 10 to about 100, and the numeric values for q corresponds to as range from about 12 to about 1200. In subsets of these embodiments, q can also be in a range of from about 100 to about 500. In certain subsets of this Embodiment, p and q are sufficient to provide a number average molecular weight for the subunits comprising cMAP and PEG, respectively, independently in a range of from about 500 Da to about 1000 Da, greater than 1000 Da to about 5000 Da, greater than 5000 Da to about 10,000 Da, greater than 10,000 to about 25,000 Da, greater than 25,000 Da to about 50,000 Da, or any combination of two or more of these ranges, as well as the corresponding numeric values for these $MW_n$ ranges. In other subsets of this Embodiment, $X_1$ and $X_2$ are independently —$(CH_2)_{1-4}$—COOH and —$(CH_2)_{1-4}$—$NH_2$ Additionally, or alternatively, in certain Aspects of Embodiments 19 to 22, m is 4, 5, or 6, preferably 5.

Additionally, or alternatively, in certain Aspects of Embodiments 19 to 22, wherein n is 1.

Additionally, or alternatively, in certain Aspects of Embodiments 19 to 22, wherein r is 2, 3, or 4, preferably 3.

Embodiment 24. The polymer, polymer conjugate, or nanoparticle composition of any one of Embodiments 14 to 23, wherein p is sufficient to provide a number average molecular weight of the subunit comprising cMAP in a range of from about or greater than 5 kDa to about 15 kDa, from about or greater than 6 kDa to about 14 kDa, from about or greater than 7 kDa to about 13 kDa, from about or greater than 8 kDa to about 12 kDa, from about or greater than 9 kDa to about 11 kDa, or about 10 kDa. In some subset Embodiments, for example where the cMAP fragment has $MW_n$ of about 420 Da, this corresponds to p having numeric values in ranges of about 12 to about 36, from about 14 to about 33, from about 17 to about 31, from about 19 to about 29, from about 22 to about 26, or about 24.

Embodiment 25. The polymer, polymer conjugate, or nanoparticle composition of any one of Embodiments 20 to 24, wherein q is sufficient to provide a number average molecular weight of the subunit comprising PEG in a range of from about or greater than 500 Da to about 50 kDa, from about or greater than 1 kDa to about 40 kDa, from about or greater than 5 kDa to about 30 kDa, or from about or greater than 5 kDa to about 20 kDa. In some of these Embodiments, for example assuming ethylene glycol fragment has $MW_n$ of about 44 Da, this corresponds to q having numeric values in ranges of about 11 to about 1200, from about 23 to about 910, from about 110 to about 680, or from about 110 to about 450.

Embodiment 26. The polymer, polymer conjugate, or nanoparticle composition of any one of Embodiments 1 to 25, wherein the linker attaching the targeting agent to the polymer or nanoparticle core is cleavable when subject to conditions inside an endothelial cell of the blood-brain barrier, wherein the cleavage comprises hydrolysis, chemical reduction, or enzymatic cleavage of the linker.

Additionally, or alternatively, the cleavable linkage comprises one or more of an acetal, borate ester, a carboxylic ester, a diamino, a disulfide, a ketal, a hydrazone, an imine, a ketal, an orthoester, or a peptide linkage. Additionally, or alternatively, the cleavable linkage further comprises a polyethylene glycol (PEG) polymer moiety conjugated to the surface of the nanoparticle core by a pH sensitive linkage selected from the group consisting of nitrophenylboronic acid ester, carboxylic acid ester, diamino ketal, orthoester, acetal, ketal, imine, and hydrazone linkage. Additionally, or alternatively, where the surface of the nanoparticle core is or comprises a poly(lactic-co-glycolic acid) (PLGA) polymer or moiety, the pH sensitive linkage may be a carboxylic acid ester linkage, wherein the linker is dissociable when subject to pH conditions inside an endothelial cell of the blood-brain barrier. Additionally, or alternatively, the linker may comprise a polyethylene glycol (PEG) polymer moiety conjugated to the surface of the nanoparticle core by a peptide linkage, wherein the peptide linkage can be enzymatically cleaved to cause dissociation of the ligand from the nanoparticle when the nanoparticle is inside a brain endothelial cell).

A variety of linkers may be used to attach the targeting ligand to the polymer or nanoparticle core, and in some instances may be used with different nanoparticles. In some Aspects of this Embodiment, the cleavable linker may include a polypeptide or chemical bond that can be chemically or enzymatically cleaved to cause disassociation of the ligand from the nanoparticle when the nanoparticle is inside a brain endothelial cell. For example, the linker can incorporate an enzyme target sequence just before the attached ligand to facilitate cleavage of the ligand following entry into a cellular endosome, thereby separating the ligand from the nanoparticle. In one embodiment the linker may include a cathepsin cleavage site to promote disassociation of the ligand from the nanoparticle. Those skilled in the art will understand that other sequences targeted by enzymes could be employed in a similar manner to cause disassociation of the nanoparticle from its ligand, which will allow the nanoparticle to move into the parenchyma of the CNS following excretion by the cell. Alternatively, a proteasome degradation tag could also be incorporated into the linker to cause the ligand to be degraded, but leaving the nanoparticle itself intact, as this would effectively dissociate the ligand and the nanoparticle following cellular uptake. The use of linkers with particular chemical bonds that can be chemically cleaved, such as orthoesters, acetals, ketals, imines, and hydrazones, should also be understood to be within the scope of this disclosure, as those skilled in the art will appreciate that such bonds could be used to facilitate disassociation of a ligand from a conjugated nanoparticle.

In some Aspects of this Embodiment, the cleavable linker includes a disulfide bond that can be reduced to cause disassociation of the ligand from the nanoparticle when the nanoparticle is inside a brain endothelial cell. In one embodiment the disulfide bond may be placed between two component polymers bridging the nanoparticle and the ligand, such that upon reduction of the disulfide bond the nanoparticle and the ligand would be separated. In one Aspect of this Embodiment the linker is composed of two PEG polymers that are joined by a disulfide bond where one of the PEG polymers is conjugated to the nanoparticle core and the other is conjugated to a ligand that mediates targeting when linked to the nanoparticle core. After such a particle is endocytosed by a cell, the ligand can become disassociated from the nanoparticle, which will promote egress of the nanoparticle into the parenchyma of the CNS.

In some Aspects of this Embodiment, the linker may include a hydrolyzable chemical bond that can be disrupted at low pH to cause disassociation of the ligand from the nanoparticle when the nanoparticle is inside a brain endothelial cell. In one embodiment the hydrolyzable bond may be placed between two component polymers bridging the nanoparticle and the ligand, such that upon hydrolysis of the bond the nanoparticle and the ligand would be separated. In one embodiment the linker is composed of a PEG polymer conjugated to the nanoparticle core at one end and linked via a diamino ketal (DAK) to a ligand that mediates targeting. After such a particle is endocytosed by a cell, the ligand will become disassociated from the nanoparticle when it encounters a low pH environment, which will promote egress of the nanoparticle into the parenchyma of the CNS. In one Aspect, the targeting agent having a hydrolyzable chemical bond that can be disrupted at low pH to cause disassociation of the ligand from the nanoparticle could be formed by having a ligand attached to a DAK linker that is attached to PEG-orthopyridyl disulfide (OPSS), where the ligand and OPSS are at opposite ends of the targeting agent.

In some Aspects of this Embodiment, the linker may include a chemical bond having a pKa that can be disrupted at low pH to cause disassociation of the ligand from the nanoparticle when the nanoparticle is inside a brain endothelial cell. In one embodiment the hydrolyzable bond may be placed at one end of the targeting agent to mediate conjugation to the nanoparticle core. In this configuration, a shift in the pH that favors hydrolysis of the bond between the nanoparticle core and the targeting ligand would cause the core to be separated from the ligand on the targeting ligand. In one Aspect of this Embodiment, the targeting ligand linker comprises a borate ester linkage, that permit covalent bonding between the nanoparticle core and the targeting ligand, but once the particle is endocytosed by a cell, the ligand will become disassociated from the nanoparticle when it encounters a low pH environment sufficient to hydrolyze the borate ester, this hydrolysis promoting the egress of the nanoparticle into the parenchyma of the CNS Embodiment 27. The polymer, polymer conjugate, or nanoparticle composition of any one of Embodiments 1 to 26, comprising at least one borate ester of a (nitro)phenyl boronic acid-containing polymer comprising a structure:

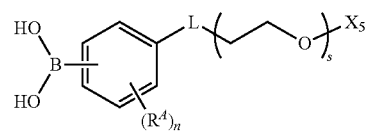

wherein
the polymer or nanoparticle core and the (nitro)phenyl boronic acid-containing polymer are reversible connected to one another by the borate condensation linkage between the (nitro)phenyl boronic acid moieties of the (nitro)phenyl boronic acid-containing polymer and at least one pair of vicinal diols of the polymer or nanoparticle core, $X_5$ being at the distal end of this connection;

$R^4$ is nitro (or other electron withdrawing group);

n is 0, 1, 2, 3, or 4, preferably 1;

s is a number in a range of from 2 to 2000;

L is a linking group between the phenyl ring and the polyethylene oxide linkage, the linking group comprising an amide, carbonate, ester, or disulfide group; and $X_5$ is a $C_{1-6}$ alkyl, optionally substituted with —OH, —COOH, —B(OH)$_2$—, —C(=O)O(alkyl), —C(=O)O(aryl), —NH$_2$, —NH(alkyl), —N(alkyl)$_2$, or —SH, and/or the at least one targeting agent coupled thereto.

In some Aspects of this Embodiment, s is any whole number between 20 and 1200. In certain embodiments, s may be any whole number between about 120 and about 180. In some embodiments, n may be any whole number between about 140 and 160. In some embodiments, s may be any one of 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, or 160. Alternatively, the PEG segment used with any of the linkers described herein may be about 2 kDa, about 5 kDa, about 6, kDa, about 7 kDa, about 8 kDa, about 9 kDa, about 10 kDa, about 11 kDa, about 12 kDa, about 13 kDa, about 14 kDa, or about 15 kDa.

Exemplary structures for the (nitro)phenyl boronic acid moiety include:

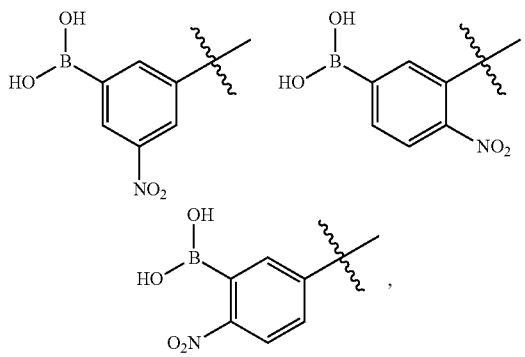

though it should be apparent that the borate —B(OH)$_2$ functional group can be ortho or para to the L group, as well as meta, and nitro group can occupy any position not otherwise occupied by the L or —B(OH)$_2$ groups.

Additionally, or alternatively, in certain Aspects of this Embodiment, at least one of these (nitro)phenyl boronic acid-containing polymer links or couples a single targeting agent to the polymer or nanoparticle core. That is, while each polymer or nanoparticle core may have a plurality of these (nitro)phenyl boronic acid-containing polymers attached thereto, in some independent Aspects, only one of these (nitro)phenyl boronic acid-containing polymers (on average) links the targeting agent to the polymer or nanoparticle core.

Additionally, or alternatively, in other Aspects of this Embodiment, two or more (e.g., 2, 3, 4, 5, 6, 7, 8, 9, 10, or more) of these (nitro)phenyl boronic acid-containing polymers each link or couple independent targeting agents to a single polymer or nanoparticle core, where the independent targeting agents may be the same or different.

Additionally, or alternatively, in other Aspects of this Embodiment, L is —(C$_{0-2}$alkylene-)NH—C(=O)—(C$_{0-2}$alkylene)-, —(C$_{0-2}$alkylene)-C(=O)—NH—(C$_{0-2}$alkylene)-, —(C$_{0-2}$alkylene)-O—C(=O)—(C$_{0-2}$alkylene)- or —(C$_{0-2}$alkylene)-C(=O)—O—(C$_{0-2}$alkylene)-.

Additionally, or alternatively, in other Aspects of this Embodiment, L is —NH—C(=O)—, —C(=O)—NH—, —O—C(=O)—, or —C(=O)—O—.

Embodiment 28. The polymer, polymer conjugate, or nanoparticle composition of any one of Embodiments 1 to 27, wherein the at least one targeting ligand independently comprises or consists of a nucleotide, polynucleotide, aptamer, peptide, oligopeptide, polypeptide, protein, polysaccharide, antibody or antibody fragment.

Additionally, or alternatively, and as described elsewhere herein, the at least one of the targeting ligands is one known to specifically bind to receptor or surface protein expressed by a brain endothelial cell that undergoes transcytosis. Targeting cellular proteins that undergo transcytosis may increase the likelihood of success of the provided methods because these cellular proteins are known to transport proteins and other molecules from one side of a cell to the other, often in a coordinated manner. Additionally, or alternatively, the targeting ligand that may be used in the compositions and with the described methods independently comprises or consists of, but are not limited to, transferrin, an antibody specific for the transferrin receptor, a polypeptide that specifically binds to the transferrin receptor, insulin, an antibody specific for the insulin receptor, a polypeptide that specifically binds to the insulin receptor, insulin-like growth factor 1, an antibody specific for the insulin-like growth factor receptor 1, a polypeptide that specifically binds to the insulin-like growth factor receptor 1, apolipoprotein E, angiopep-2, an antibody specific for low density lipoprotein receptor or lipoprotein receptor-related protein, a polypeptide that specifically binds to low density lipoprotein receptor or lipoprotein receptor-related protein; an antibody specific for diphtheria toxin receptor, or a polypeptide that specifically binds to diphtheria toxin receptor. Other cellular proteins capable of facilitating transcytosis that are known in the art may also be targeted by a ligand for carrying out the methods disclosed herein.

Additionally, or alternatively, the targeting ligand is or comprises any one of the foregoing targeting ligands that are known to associate with hematopoietic differentiation antigens (glycoproteins usually associated with CD groupings and include CD20, CD30, CD33, and CD52). Additionally, or alternatively, the targeting ligand is or comprises any one of the foregoing targeting ligands that are known to associate with growth factors such as epidermal growth factor receptor (EGFR; also known as ErbB1), ErbB2 (also known as HER2), ErbB3, MET, insulin-like growth factor 1 receptor (IGF1R), ephrin receptor A3 (EphA3), TNF receptor apoptosis-inducing ligand receptor 1 (TRAIL-R1), TRAIL-R2, and receptor activator of nuclear factor KO ligand (RANKL). Additionally, or alternatively, the targeting ligand is or comprises any one of the foregoing targeting ligands that are known to associate with proteins or growth factors that support the formation of new microvasculature, including vascular endothelial growth factor (VEGF), VEGF receptor (VEGFR), and integrins αVβ3 and α5β1. Additionally, or alternatively, the targeting ligand is or comprises any one of the foregoing targeting ligands that are known to associate with Stromal and extracellular matrix antigens that are therapeutic targets include fibroblast activation protein (FAP) and tenascin.

Embodiment 29. The polymer, polymer conjugate, or nanoparticle composition of any one of Embodiments 1 to 28, wherein the at least one targeting ligand is present in a range of from one to 1000, conjugated to the polymer or nanoparticle core by the linking groups. Additional or alternative Aspects of this Embodiment provide independently for the presence of 1, 2, 3, 4, or 5 targeting ligands per polymer or nanoparticle core. Additional or alternative Aspects of this Embodiment provide independently for the presence of an average of 1, 2, 3, 4, or 5 targeting ligands per polymer or nanoparticle core in a population of polymer or nanoparticle core. Additionally, or alternatively, each polymer or nanoparticle core may have attached thereto a number of targeting ligands in a range of from 1 to 5, from 5 to 10, from 10 to 15, from 15 to 20, from 20 to 50, from 50 to 100, from 100 to 200, from 200 to 300, from 300 to 400, from 400 to 500, or from 500 to 1000 per polymer or nanoparticle core, or a range of two or more of the foregoing ranges, for example from 1 to 10 or from 5 to 50 targeting ligands per polymer or nanoparticle core, either on an individual basis or on average for a population of the polymer or nanoparticle cores.

In each case, the targeting ligands may comprise the same or different chemical moieties suitable for this purpose.

In alternative, or additional Aspects of this Embodiment, the polymer or nanoparticle core(s) may contain additional cleavable linking groups that are not conjugated to the targeting ligands (i.e., the number of cleavable linking groups attached to the polymer or nanoparticle core is greater than the number of conjugated targeting ligands). For example, a given polymer or nanoparticle core may have 100 cleavable linking groups attached to the core, only 1, 2, 3, 4, or 5 of which are conjugated to a targeting ligand. The remaining cleavable linking groups may be free appendages (i.e., contain a functional group capable of binding to another chemical group, such as described elsewhere herein) and/or may serve as a binding site for one or more of the small or large molecule therapeutic agents or imaging agents described herein. In such Aspects of this Embodiment, the polymer or nanoparticle core may comprise 1, 2, 3, 4, or 5 cleavable linking group per polymer or nanoparticle core, wherein all or only a portion of which are conjugated to the at least one targeting ligand. Additional or alternative Aspects of this Embodiment provide independently for the presence of an average of 1, 2, 3, 4, or 5 cleavable linking groups per polymer or nanoparticle core in a population of polymer or nanoparticle core, wherein all or only a portion of which are conjugated to the at least one targeting ligand as set forth above. Additionally, or alternatively, each polymer or nanoparticle core may have attached thereto a number of cleavable linking groups in a range of from 1 to 5, from 5 to 10, from 10 to 15, from 15 to 20, from 20 to 50, from 50 to 100, from 100 to 200, from 200 to 300, from 300 to 400, from 400 to 500, or from 500 to 1000 per polymer or nanoparticle core, or a range of two or more of the foregoing ranges, for example from 1 to 10 or from 5 to 50 targeting ligands per polymer or nanoparticle core, either on an individual basis or on average for a population of the polymer or nanoparticle cores, wherein all or only a portion of which are conjugated to the at least one targeting ligand as set forth above.

In alternative, or additional Aspects of this Embodiment, the ratio of targeting agents to cleavable linking groups attached to the polymer or nanoparticle core may be about 100:1, about 50:1, about 20:1, about 10:1, about 7:1, about 5:1, about 4:1, about 3:1, about 2:1, or about 1:1. Alternatively, or alternatively, the relative distribution of cleavable linking groups and the targeting agents may be described in term of the percentage of total attached conjugates that are targeting agents, relative to the total cleavable linking groups. In some independent Aspects, the targeting ligands are conjugated to about 1%, 2%, 3%, 4%, 5%, 6%, 7%, 8%, 9%, 10%, 15%, 20%, 25%, 30%, 40%, 50%, 60%, 70%, 80%, 90%, 95%, 98%, or substantially 100% of the cleavable linking groups attached to the polymer or nanoparticle core. The ratios and percentages described herein may account for mixed populations of conjugates, such as embodiments where more than one targeting agent and/or spacer molecule is attached to a nanoparticle core.

Additionally, the nanoparticle core and targeting ligand can be conjugated by a linker that can facilitate disassociation of the ligand from the nanoparticle when inside a brain endothelial cell. In some of the described embodiments the linker may include a disulfide bond that can be reduced to cause disassociation of the ligand from the nanoparticle when the nanoparticle is inside a brain endothelial cell. As also disclosed elsewhere herein, the targeting ligand linker may include a polypeptide that can be enzymatically cleaved to cause disassociation of the ligand from the nanoparticle when the nanoparticle is inside a brain endothelial cell. In some of the described embodiments the linker may include a hydrolyzable chemical bond that can be disrupted at low pH to cause disassociation of the ligand from the nanoparticle when the nanoparticle is inside a brain endothelial cell. In some of the described embodiments the linker may include a chemical bond having a pKa that can be disrupted at low pH to cause disassociation of the ligand from the nanoparticle when the nanoparticle is inside a brain endothelial cell. In some of these Aspects, the linker comprises a nitrophenyl boronic acid when unbound to the nanoparticle that forms a nitrophenyl boronic ester to bind to the nanoparticle core, where decoupling of the linker and the nanoparticle core will be favored at acidic pH (e.g., about 6.8 to about 2.0). In other independent Aspects, the targeting agent may include a diamino ketal (DAK) linkage to facilitate disassociation of the nanoparticle and the ligand once inside a brain endothelial cell, where decoupling of the linker and the nanoparticle core will be favored at acidic pH. Additionally, the described methods may be carried out using a targeting agent with a linker having a disulfide bond that can facilitate disassociation of an attached ligand from the nanoparticle under reducing conditions encountered in a brain endothelial cell.

Additionally, or alternatively, while at least one targeting ligand is linked to the polymer or nanoparticle core by a cleavable linking group, not all targeting ligands need to be so linked. In other Aspects of this Embodiment the polymer or nanoparticle core may comprise a first targeting ligand and a second targeting ligand, wherein the first targeting ligand is linked by such a cleavable linkage, whereas the second targeting ligand is not, and the second targeting ligand is linked by a linker that is not amenable to disassociation from the nanoparticle core when inside of a brain endothelial cell, and that second targeting ligand targets the nanoparticle to a specific cell in the brain.

Embodiment 30. The polymer, polymer conjugate, or nanoparticle composition of any one of Embodiments 1 to 29, wherein the small molecule is a pharmaceutical compound useful in the treatment of Alzheimer's disease, Huntington's disease, Parkinson's disease, multiple sclerosis, or cancer, including brain cancer, including brain cancer metastasized from HER2-positive breast cancer.

In certain Aspects of this Embodiment, the small molecule is a neurotransmitter. Additionally, or alternatively, the small molecule is dopamine or serotonin.

In certain Aspects of this Embodiment, the small molecule is a chemotherapeutic. Additionally, or alternatively, the small molecule is one or more of Camptothecin, Erlotinib (Tarceva®), Gefitinib (Iressa®), Imatinib (Gleevec®), Irinotecan, Lapatinib, SN-38, or a derivative, metabolite, or prodrug thereof.

Additionally, or alternatively, the small molecule is or comprises abraxane, actinomycin, alitrerinoin, azacitidine, azathioprine, bexarotene, bleomycin, bortezomib, camptothecin, capecitabone, carboplatin, cisplatin, capecitabine, chlorambucil, cyclophosphamide, cytarabine, dacarbazine, docetaxel, doxifluiridine, daunorubcin, doxorubicin, epirubicin, epothilone, erlotinib, etoposide, 5-fluorouracil, folinic acid, gefitinib, gemcitabine, idarubicin, imatinib, irinotecan, mechlorethamine, melphalan, mercaptopurine, methotrexate, mitoxanrone, mustine, oxaliplatin, paclitaxel, prednisolone, procarbazine, romidepsin, tafluposide, taxotere, teniposide, thioguainine topotecan, tretinoin, valrubicin, vemurafenib, vinblastine, vincristine, vindesine, vinorelbine, vismodegib, vorinosat, or a derivative, metabolite, or prodrug thereof.

Additionally, or alternatively, the small molecule may include molecules more broadly described in U.S. Pat. Nos. 5,747,498; 6,900,221; 7,087,613; RE41065 (corresponding to Erlotinib); U.S. Pat. Nos. 5,457,105; 5,616,582; 5,770, 599 (corresponding to Gefitinib); U.S. Pat. Nos. 6,391,874; 6,713,485; 6,727,256; 6,828,320; and 7,157,466 (corresponding to Lapatinib), each of which is incorporated by reference herein in its entirety. In still other Aspects of this Embodiment, additionally, or alternatively, the small molecule may include any one of the fused heterocyclic compounds disclosed in WO97/13771, WO98/02437, WO00/44728, U.S. Pat. No. 6,596,878, US 2005/0148607, and US 2008/0214584; any one of the quinazoline derivatives disclosed in WO02/02552, WO01/98277, WO03/049740, WO03/050108, and U.S. Pat. No. 6,596,878; any one of the thienopyrimidine derivatives disclosed in WO03/053446 and U.S. Pat. No. 7,300,935; any one of the thienyl derivatives disclosed in U.S. Pat. No. 5,710,173; any one of the aromatic azole derivatives disclosed in WO01/77107, WO03/031442, U.S. Pat. Nos. 6,716,863 and 6,984,653; any one of the bicyclic or heterocyclic aryl compounds disclosed in WO 92/20642; any one of the vinylene-azaindole derivatives disclosed in WO94/14808; any one of the azaindoles disclosed in WO03/000688 and WO96/000226; any one of the 1-cyclopropyl-4-pyridyl-quinolones disclosed in U.S. Pat. No. 5,330,992; any one of the styryl compounds disclosed in U.S. Pat. Nos. 5,217,999 and 5,596,878; any one of the styryl-substituted pyridyl compounds disclosed in U.S. Pat. No. 5,302,606; any one of the tyrphostin-like compounds disclosed in U.S. Pat. No. 6,225,346; any one of the seleoindoles or selenides disclosed in WO94/03427; any one of the 1H-pyrrolo[2,3-b]pyridines disclosed in WO01/098299; any one of the tricyclic polyhydroxylic compounds disclosed in WO92/21660; any one of the 2-pyrazolin-5-ones disclosed in WO 01/01921), and benzylphosphonic acid compounds disclosed in WO91/15495) Each of these compounds have been described as compounds for use as tyrosine kinase inhibitors for use in the treatment of cancer. Each of these references is incorporated by reference herein in its entirety for all purposes, or at least for the compounds disclosed as useful in the treatment of cancer.

Alternatively, or additionally, the small molecule can also be "tagged" with radio-isotopes for molecular imaging of the tumor marker in vivo. Radio-labeled compounds are required for Positron Emission Tomography (PET) and Single Photon Emission Computed Tomography (SPECT). Such imaging enhancing agent can include at least one of tritium, boron-10, carbon-11, gallium-68, nitrogen-13, sulfur-35, iodine-131, or fluorine-18 at a level above the natural abundance of each element.

Embodiment 31. The polymer, polymer conjugate, or nanoparticle composition of any one of Embodiments 1 to 30, wherein the small molecule therapeutic compound is linked to the nanoparticle core by way of an optional linker. As set forth above, the small molecule therapeutic molecule may be chemically or electrostatically bonded to the polymer or nanoparticle core or may be encasulated within the structure of the nanoparticle core without being chemically or electrostatically bonded. For example, the nanoparticle may present a hydrophilic exterior surface in aqueous media, while having a hydrophobic pocket within its structure, allowing for the encapulation of a hydrophobic small molecule therapeutic to be encapsulated within that hydrophobic pocket.

The term "optional linker" in the context of this Embodiment refers to independent Aspects of this Embodiment where the attachment of the small molecule therapeutic compound to the nanoparticle core is either by a direct chemical bond or via a linking group. The linking group may be either chemically stable (i.e., able to maintain its structure in its presented or intended environment) or may be cleavable by any of the mechanisms associated with the term "cleavable" as set forth elsewhere herein. Additionally, or alternatively, this linking group may comprise one or more amino acid residues, such as a residue of arginine, histidine, lysine, aspartic acid, glutamic acid, serine, threonine, asparagine, glutamine, tyrosine, tryptophan, or a salt thereof. In but one non-limiting example of this concept, the small molecule therapeutic compound, camptothecin, is linked to a MAP polymer nanopolymer surface according to:

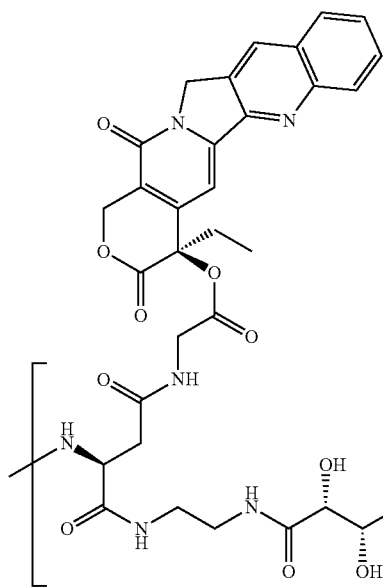
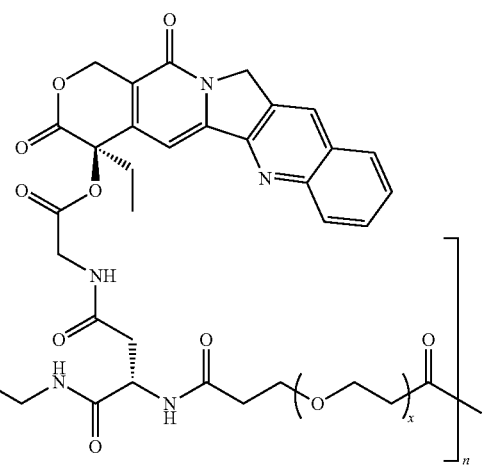

Embodiment 32. The polymer, polymer conjugate, or nanoparticle composition of any one of Embodiments 1 to 31, wherein the large molecule therapeutic agent is a nucleotide, polynucleotide, aptamer, peptide, oligopeptide, polypeptide, protein, polysaccharide, antibody or antibody fragment useful in the treatment of Alzheimer's disease, Huntington's disease, Parkinson's disease, multiple sclerosi, and cancer. In certain Aspects of this Embodiment, the large molecule is an antibody.

Additionally, or alternatively, the large molecule therapeutic agent is an antibody and the antibody is a monoclonal antibody. Additionally, or alternatively, the large molecule therapeutic agent is abciximab (Reopro), adalimumab, alemtuzumab (Campath), basiliximab (Simulect), belimumab (Benlysta), bevacizurnab (Avastin), bezlotoxumab (Zinplava), canakinumab (Ilaris), certolizumab pegol (Cimzia), cetuximab (Erbitux), daclizumab (Zenapax, Zinbryta), denosumab (Prolia, Xgeva), efalizumab (Raptiva), golimuimab (Simponi, Sirnponi Aria), inflectra (Remicade), ipilimumab (Yervoy), ixekizumab (Taltz), natalizumab (Tysabri), necitumumab (Portrazza), nivolumab (Opdivo), obinutuzumab (Gazyva), ocrelizumab (Ocrevus), ofatumumab (Arzerra), olaratumab (Lartruvo), onalizuiab (Xolair), palivizumab (Synagis), panitumumab (Vectibix), pembrolizumab (Keytruda), pertuzumab (Perjeta), ramucirumab (Cyramza), rituximab (Rituxan), secukinumab (Cosentyx), tocilizumab (Actemra), trastuzumab (Herceptin®), and/or ustekinumab (Stelara). Additionally, or alternatively, the large molecule therapeutic agent is a conjugated monoclonal antibody. Additionally, or alternatively, the large molecule therapeutic agent is a ibritumomab tiuxetan (Zevalin), Brentuximab vedotin (Adcetris), or Ado-trastuzumab emtansine (Kadcyla, also called TDM-1), denileukin diftitox (Ontak). Additionally, or alternatively, the large molecule therapeutic agent is one or more of ipilimumab, natalizumab, necitumumab, nivolumab, obinutuzumab, ocrelizumab, pembrolizumab, pertuzumab, or pamucirumab. Additionally, or alternatively, the large molecule therapeutic agent is one or more of adalimumab (Humira, Anjevita), Bevacizumab (Avastin), cetuximab (Erbitux) ipilimumab (Yervoy), natalizumab (Tysabri), necitumunab (Portrazza), nivolumab (Opdivo), obinutuzumab (Gazyva), ocrelizumab (Ocrevus), panitumumab (Vectibix), pembrolizumab (Keytruda), pertuzumab (Perjeta), rarnucirurnab (Cyramza) rituximab (Rituxan), trastuzumab (Herceptin). Additionally, or alternatively, the large molecule therapeutic agent is arcitumomab, ibritumomab, capromab pendetide, and/or tositumomab.

Additionally, or alternatively, the antibody includes one known to associate with hematopoietic differentiation antigens (glycoproteins usually associated with CD groupings and include CD20, CD30, CD33, and CD52). Additionally, or alternatively, the antibody includes one known to associate with growth factors such as epidermal growth factor receptor (EGFR; also known as ErbB1), ErbB2 (also known as HER2), ErbB3, MET, insulin-like growth factor 1 receptor (IGF1R), ephrin receptor A3 (EphA3), TNF receptor apoptosis-inducing ligand receptor 1 (TRAIL-R1), TRAIL-R2, and receptor activator of nuclear factor $\kappa\beta$ ligand (RANKL). Additionally, or alternatively, the antibody includes one known to associate with proteins or growth factors that support the formation of new microvasculature, including vascular endothelial growth factor (VEGF), VEGF receptor (VEGFR), and integrins $\alpha V\beta 3$ and $\alpha 5\beta 1$. Additionally, or alternatively, the antibody includes one known to associate with Stromal and extracellular matrix antigens that are therapeutic targets include fibroblast activation protein (FAP) and tenascin.

Additionally, or alternatively, the large molecule therapeutic agent is a polynucleotide. Within this Aspect, the polynucleotide is or comprises a genomic DNA, cDNA, mRNA, siRNA, shRNA, miRNA, antisense oligonucleotide, virus, or a chimeric polynucleotide. or a small molecule therapeutic agent. Additionally, or alternatively, the polynucleotide that is an RNA molecule, preferably an siRNA molecule.

Additionally, or alternatively, the large molecule therapeutic agent is a fusion protein. Additionally, or alternatively, the large molecule therapeutic agent is Abatacept, Alefacept (Amevive) Aflibercept, or Etanercept Additionally, or alternatively, in the context of this Embodiment, the large molecule therapeutic compound may be attached to the polymer or nanoparticle core either by a direct chemical bond or via a linking group. The linking group may be either chemically stable (i.e., able to maintain its structure in its presented or intended environment) or may be cleavable by any of the mechanisms associated with the term "cleavable" as set forth elsewhere herein. Additionally, or alternatively, this linking group may comprise one or more amino acid residues, such as for example arginine, histidine, lysine, aspartic acid, glutamic acid, serine, threonine, asparagine, glutamine, tyrosine, tryptophan, or a salt thereof.

Embodiment 33. The polymer, polymer conjugate, or nanoparticle composition of any one of Embodiments 1 to 32, wherein the composition is a nanoparticle, Embodiment 34. The nanoparticle of any one of claims 1 to 33, said nanoparticle being substantially spherical and having a cross-section dimension in a range of from about 20 nm to about 300 nm. Additional, or alternative Aspects of this Embodiment include those where the cross-section dimension of the nanoparticles are in a range of from 20 nm to 30 nm, from 30 nm to 40 nm, from 40 nm to 50 nm, from 50 nm to 60 nm, from 60 nm to 70 nm, from 70 nm to 80 nm, from 80 nm to 90 nm, from 90 nm to 100 nm, from 100 nm to 120 nm, from 120 nm to 140 nm, from 140 nm to 160 nm, from 160 nm to 180 nm, from 180 nm to 200 nm, from 200 nm to 220 nm, from 220 nm to 240 nm, from 240 nm to 260 nm, from 260 nm to 280 nm, from 280 nm to 300 nm, or any combination of two or more of these foregoing ranges, for example from 80 nm to 100 nm. In each of these cases, the dimensions refer to measurements obtained by dynamic light scattering, though any other method as known in the art may be used.

Embodiment 35. The nanoparticle of any one of claims 1 to 34, the nanoparticle having an average zeta potential of from about 0 mV to about −15.0 mV as measured by phase analysis light scattering. In certain Aspects of this Embodiment, the charge of the targeted nanoparticle is near neutral. Alternatively, or additionally, the zeta potential of the nanoparticles for use with the methods described herein can be characterized as having a range of from about 0 mV to about 0.5 mV, from about −0.5 mV to about −1 mV, from about −1 mV to about −2 mV, from about −2 mV to about −3 mV, from about −3 mV to about −4 mV, from about −4 mV to about −5 mV, from about −5 mV to about −6 mV, from about −6 mV to about −7 mV, from about −7 mV to about −8 mV, from about −8 mV to about −9 mV, from about −9 mV to about −10 mV, from about −10 mV to about −11 mV, from about −11 to about −12 mV, from about −12 mV to about −13 mV, from about −13 mV to about −14 mV, from about −14 mV to about −15 mV, or a combination of two or more of these ranges, for example, in a range of from about −5 mV to about −7 mV. In some Aspects of this Embodiment the described nanoparticle will have a zeta potential of −5.0, −5.1, −5.2, −5.3, −5.4, −5.5, −5.6, −5.7, −5.8, −5.9, −6.0, −6.1, −6.2, −6.3, −6.4, −6.5, −6.6, −6.7, −6.8, −6.9, −7.0, −7.1, −7.2, −7.3, −7.4, −7.5, −7.6, −7.7, −7.8, −7.9, or −8.0 mV.

Embodiment 36. The nanoparticle of any one of Embodiments 1 to 35, the nanoparticle further comprising an imaging agent. In certain Aspects of this Embodiment, the imaging agent is present in addition to the small molecule or large molecule therapeutic. In other independent Aspects of this Embodiment, the imaging agent is present in lieu of one or both of the small molecule or large molecule therapeutic. In certain Aspects of this Embodiment, the imaging agent is Cu-64.

Embodiment 37. A plurality of nanoparticles, each individual nanoparticle comprising the composition of any one of Embodiments 1 to 32 or described in terms of any one of Embodiments 33 to 36.

Embodiment 38. The plurality of nanoparticles of Embodiment 36, each individual nanoparticle being described by the composition of any one of Embodiments 1 to 32 or the characteristics of any one of Embodiments 33 to 36, the plurality of nanoparticles being substantially monodispersed, exhibiting a standard deviation in cross-sectional dimension (i.e., diameter) among the nanoparticles of less than 20%, 30%, 40%, 50%, or 60%, as measured by cryo-transmission electron microscopy (cryo-TEM).

Embodiment 39. A pharmaceutical composition comprising the polymer, polymer conjugate, or nanoparticle composition of any one of Embodiments 1 to 38, the composition comprising a biologically active agent and pharmaceutically acceptable carrier or excipient.

In certain Aspects of this Embodiment, the polymers, polymer-conjugates, and/or nanoparticles may exist as dispersions in aqueous media, said aqueous media optionally also containing buffers, surfactants, or other modifiers. The present disclosure also contemplates pharmaceutical compositions comprising one or more biologically active agents and any of the polymers or polymer conjugates or nanoparticles or plurality of nanoparticles described herein and a pharmaceutically acceptable vehicle, carrier or excipient.

Embodiment 40. A method of delivering enhanced levels of a therapeutic agent or imaging agent to a brain parenchyma of a subject having a neurological brain disorder, the method comprising systemically administering the nanoparticles of any one of Embodiments 1 to 38 or a pharmaceutical composition of Embodiment 39 to a patient in need of such enhanced delivery. Implicit in certain aspects of this description is that at least one of the therapeutic agents or imaging agents being ferried by the nanoparticle composition may itself be unable to make the passage across the blood brain barrier to achieve therapeutically effective amounts in the parenchyma without the use of the nanoparticles disclosed herein (i.e., the cargo falls outside the definition of small molecule capable of passing the blood brain barrier set forth elsewhere herein). In this regard, the bioavailability of the therapeutic or imaging agent is improved using the nanoparticle, relative to an administration of the therapeutic or imaging agent by itself. The description of enhanced delivery or enhanced levels is intended to reflect the ability of the disclosed nanoparticles to pass through the BBB, by transcytosis or other means, to deliver the cargo (therapeutic and/or imaging agents) at levels and/or rates higher than the cargo can be delivered themselves (without being ferried by the nanoparticles).

Additionally, or alternatively, further Aspects of this Embodiment comprise method of treating a neurological disorder in a patient, the methods comprising systemically administering a first small molecule therapeutic agent and/or a large molecule therapeutic agent to the patient in need of such treatment, wherein (a) the first small molecule therapeutic agent and/or the large molecule therapeutic agent is attached to a nanoparticle comprising a nanoparticle core and a targeting agent, the targeting agent comprising at least one targeting ligand attached to an external surface of the nanoparticle core by a linker having a cleavable linkage;
  (i) the external surface of the nanoparticle comprising a neutral and/or negatively charged mucic acid-containing polymer (MAP) (including substantially free of cationic mucic-acid containing polymer (cMAP));

(ii) the at least one targeting ligand having an affinity for binding to a receptor expressed by endothelial cells of the blood-brain barrier; and (iii) the cleavable linkage being cleavable when subject to conditions inside an endothelial cell of the blood-brain barrier, wherein the cleavage comprises hydrolysis, chemical reduction, or enzymatic cleavage of the linker; and wherein one or both of (iv) the small molecule therapeutic agent is optionally linked to the nanoparticle core by way of an optional linker; and/or (v) the large molecule therapeutic agent is linked to the nanoparticle by way of an optional linker; and (b) the administration of the first small molecule therapeutic agent and/or the large molecule therapeutic agent attached to the nanoparticle results in the delivery of the first small molecule therapeutic agent and/or the large molecule therapeutic agent past the blood brain barrier and into the subject's brain parenchyma in an amount is greater than would be delivered were the first small molecule therapeutic agent and/or the large molecule therapeutic agent not attached to the nanoparticle.

Additionally, or alternatively, in some further Aspects of this Embodiment, a useful figure of merit for measuring the utility of these methods is an enhancement ratio of the steady state amount of small or large molecule therapeutic or imaging agent present in the brain parenchyma, having passed through the blood brain barrier after systemic delivery through use of these nanoparticles, relative to the amount of small or large molecule therapeutic or imaging agent present in the brain parenchyma, having passed through the blood brain barrier after systemic delivery of the small or large molecule therapeutic or imaging agent by itself, under otherwise comparable conditions. In certain Aspects of this Embodiment, this enhancement ratio can range from 2 to 3 times, from 3 to 5 times, from 5 to 10 times, from 10 to 25 times, from 25 to 50 times, from 50 to 100 times, from 100 time to 500 times, or a combination of two or more of these foregoing ranges, depending on the nature of the therapeutic or imaging agent.

Additionally, or alternatively, the enhanced level of the therapeutic agent delivered by the nanoparticles to the brain parenchyma can be defined as an amount that is greater than is delivered using otherwise equivalent nanoparticles that do not contain the cleavable linker under the same conditions. Additionally, or alternatively, the method may be characterized as a method of delivering enhanced levels of a therapeutic agent to a brain parenchyma of a subject having a neurological brain disorder, said therapeutic agent being unable to achieve therapeutically effective levels in the brain parenchyma through systemic administration of the agent itself, the method comprising systemically administering a plurality of one or more of the nanoparticles described herein to the subject having the neurological brain disorder (including any of the diseases set forth elsewhere herein) and in need of delivery of an enhanced level of the therapeutic agent across a blood-brain barrier to the subject's brain parenchyma, the plurality of nanoparticles being administered at a dose rate sufficient to enhance the delivery of the chemotherapeutic agent to the brain parenchyma in therapeutically useful quantities that are higher than available by systematically administering the free therapeutic agent alone.

Additionally, or alternatively, the methods of treating a patient/subject having a neurological condition may include use of the disclosed nanoparticles in combination with conventional drug or other therapy. For example, while the nanoparticle compositions described herein have been described as especially useful for ferrying therapeutics and imaging agents (that are otherwise blocked to any practical extent), across the blood brain barrier, these disclosed nanoparticle compositions may also be used to complement conventional treatments involving the use of therapeutics that can, by themselves, pass the blood brain barrier. While the number of small molecule therapeutics capable of passing through the blood brain barrier is relatively small (e.g., less than 2% of small molecule therapeutics and essentially 100% of large-molecule therapeutics), some can make this passage, as described elsewhere herein.

Accordingly, independent Aspects of this Embodiment include those methods of treating a patient known or believed to have a neurological disorder, the method comprising systemically administering a composition described in any one of Embodiments 1 to 39 to a patient or subject in need of such treatment, wherein in the composition comprises at least one small and/or large molecule therapeutic agent and/or imaging agent that by itself is incapable of passing through the blood brain barrier in sufficient amounts to yield therapeutically effective amounts in the brain parenchyma of the patient or subject, where the systemic administration results in therapeutically effective amounts of the small and/or large molecule therapeutic agent and/or imaging agent in the brain parenchyma of the patient or subject.

Alternatively, or additionally, the method further comprises systemically administering to the patient or subject in need of such treatment, a second small and/or large molecule therapeutic agent and/or imaging agent, unattached to a nanoparticle described herein, that by itself is capable of passing through the blood brain barrier to deliver a therapeutically effective amount in the brain parenchyma. The nanoparticle composition and the unattached second small and/or large molecule therapeutic agent and/or imaging agent may be administered at the same time or at different times, within a given treatment regimen.

Additionally, or alternatively, in this context, the nanoparticle composition may further comprise at least one other small and/or large molecule therapeutic agent and/or imaging agent that, by itself, can pass through the blood brain barrier to achieve therapeutically effective levels in the brain parenchyma by itself.

In but one illustrative example of this latter concept, not intending to limit its scope in any way, such methods embrace the systemic co-administration, to a patient in need of treatment for a neurological condition, of (a) a conventional small molecule therapeutic agent that can pass the blood brain barrier by itself, with (b) a nanoparticle composition as disclosed herein, where the nanoparticle composition comprises a monoclonal antibody, wherein both the conventional small molecule therapeutic and the antibody are delivered past the blood brain barrier to the brain parenchyma in therapeutically effective amounts.

In certain Aspects of this Embodiment, the neurological brain disorder is one that requires direct intervention of the therapeutic or imaging agent in the brain. Additionally, or alternatively, the neurological condition is independently Alzheimer's disease, Huntington's disease, Parkinson's disease, multiple sclerosis, or brain cancer. In certain Aspects of this Embodiment, the neurological brain disorder is a brain cancer originating from the metastasis of other systemic, extracranial cancers, including brain cancer metastasized from HER2-positive breast cancer including brain cancer metastasized from HER2-positive breast cancer.

The methods of administering these compositions are set forth elsewhere herein.

EXAMPLES

The Examples are provided to illustrate some of the concepts described within this disclosure. While each Example is considered to provide specific individual embodiments of composition, methods of preparation and use, none of the Examples should be considered to limit the more general embodiments described herein. While the examples provided here focus on specific nanoparticle materials, it is believed that the principles described are relevant to other nanoparticle materials disclosed elsewhere herein. Accordingly, the descriptions provided here should not be construed to limit the disclosure, and the reader is advised to look to the nature of the claims as a broader description.

In these examples, efforts have been made to ensure accuracy with respect to numbers used (e.g. amounts, temperature, etc.) but some experimental error and deviation should be accounted for. Unless indicated otherwise, temperature is in degrees C., pressure is at or near atmospheric.

Summary of Approach:

Herein, murine models are shown to have a significant effect on the ability of therapeutics to traverse the BBB/BTB. Certain transferrin receptor (TfR)-targeted, therapeutic nanoparticles were designed and investigated herein as representative exemplars of these general design and treatment concepts. These exemplary nanoparticles were investigated as to their brain uptake and antitumor efficacy compared to non-targeted nanoparticles and free drug in three murine models. Two of the models used have been previously described in the literature and involve intracranial (IC) or intracardiac (ICD) injection of human breast cancer cells. A third model developed here involves intravenous (IV) injection of the cancer cells.

The present study focused on HER2-positive breast cancer brain metastasis because of the inadequate drug concentrations achieved in these tumors in the clinical setting. In contrast, the targeted nanoparticle delivery system described herein was found to be useful in delivering CPT to HER2-positive breast cancer brain metastases. Importantly, significant differences in efficacy as well as brain penetration of both TfR-targeted and non-targeted therapeutics were observed between the models, showing that the method of establishing brain metastases can affect brain uptake of therapeutic agents.

The present studies focused on understanding whether two types of breast cancer brain metastasis mouse models from the literature as well as a third, new model created in this study provide impaired drug delivery to brain metastases like what is observed for patients with HER2-positive, metastatic breast cancer. In patients, non-BBB-permeable agents were unable to accumulate in brain metastases in pharmacologically active amounts. However, this same delivery limitation was not observed in the IC model. These results showed that a non-BBB-penetrant small molecule (CPT) and a non-targeted nanoparticle therapeutic (ca. 30-40 nm diameter) could elicit a significant antitumor response as well as accumulate in high amounts in IC-established brain tumors. In contrast to the IC model, both the ICD and IV models provided for a more intact BBB/BTB. These results indicated that the ICD model may allow for a slightly increased permeability to small molecule drugs, but not to larger nanoparticle entities when compared to the IV model. Consistent with a modest uptake in healthy brain tissue, it is possible that the high number of microscopic tumor foci commonly observed throughout the brain following ICD injection may contribute to a slight net increase in parenchymal penetration as a whole. Nevertheless, this effect was minimal.

Most importantly, the present data show that the method of establishing brain tumors can dramatically affect the efficacy of therapeutics and their brain penetration. These findings suggested that, although the IC model allowed for consistent and reproducible tumor growth in the brain parenchyma and thus may be useful for studying basic biological mechanisms, this model must be used with caution for translational research with diseases where a non-permissive BBB is clinically relevant. While tumor burden is not as consistent in the ICD and IV models, our data support the use of these models if the experimenter is interested in transport properties of a given therapeutic.

Additionally, the present studies showed that TfR-targeted nanoparticles were capable of delivering a small molecule chemotherapeutic, CPT, to HER2-positive breast cancer brain metastases. TfR-targeted MAP-CPT nanoparticles significantly slowed tumor growth in the brain and demonstrated increased accumulation in brain metastases relative to free drug and non-targeted nanoparticles. The specific example of assembling a TfR-targeted nanoparticle system for CPT was selected to test the delivery strategy. CPT is not a particularly good drug for use with BT474 cells (relative to other breast cancer cell lines). Thus, it is encouraging to observe tumor growth delay when delivering CPT via targeted nanoparticles to the BT474-Gluc brain metastases. It is expected that TfR-targeted nanoparticles delivering therapeutic agents with greater potency will reveal even more significant tumor size reductions.

Further, TfR-targeted nanoparticles accumulated in significant amounts in healthy brain tissue when compared to free drug and non-targeted nanoparticles in all three models. This whole-brain penetration has implications for the selection of therapeutics that should be incorporated into this delivery system and of target diseases. In the case of brain cancers, the ability to penetrate not only tumor tissue, but also healthy tissue could be advantageous in accessing micrometastases or fingers of glioma tumors that are frequently the reason for treatment failure. For other brain diseases where whole-brain therapeutic exposure is highly desired, such as neurodegenerative diseases, this targeted nanoparticle system may offer a compelling approach to delivering therapeutics across an intact BBB.

Example 1. Summary

In the studies described herein, mucic acid-based, targeted nanoparticles designed to transcytose the BBB/BTB to deliver both a small molecule drug, camptothecin (CPT), and therapeutic antibody, Herceptin, and the combination was investigated as a means to treat brain metastases in mice. Treatment with BBB-targeted combination CPT/Herceptin nanoparticles significantly inhibited tumor growth compared to free CPT/Herceptin and BBB-targeted nanoparticles carrying CPT alone. Though not as efficacious, BBB-targeted nanoparticles carrying only Herceptin also elicited considerable antitumor activity. These results demonstrated the promise of the targeted nanoparticle system for the delivery of antibody alone or in combination with other drugs across the BBB/BTB to improve clinical outcomes.

Figure 3:
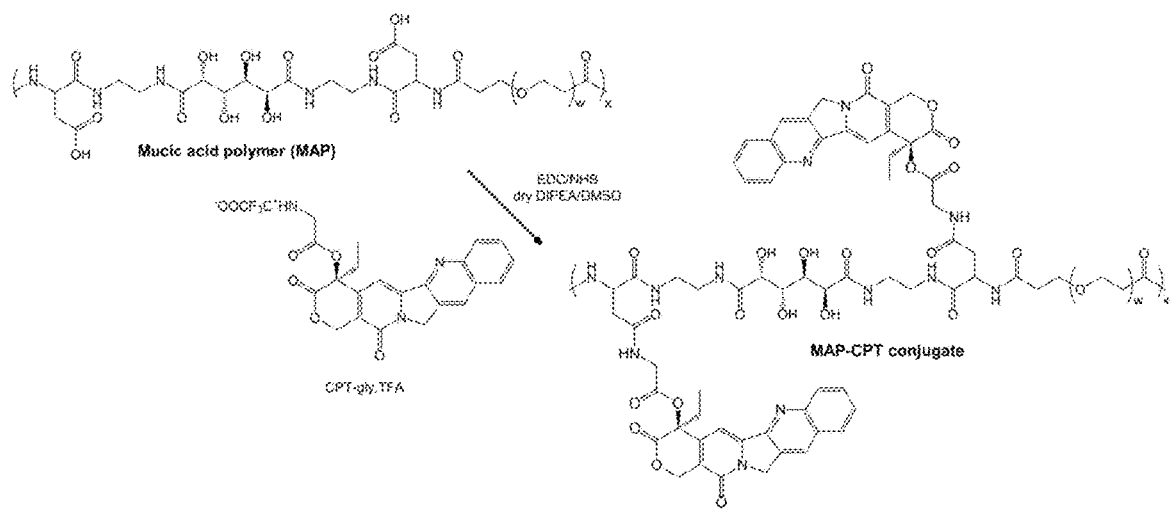
FIG. 3 shows a synthetic scheme of MAP-CPT polymer-drug conjugate. w~82 for 3.4 kDa PEG; x~20 for material used in this study.

MAP-CPT polymer-drug conjugate was prepared as described in FIG. 3. Properties of the material used in this study are provided in Table 1. MAP-CPT conjugate was then dialyzed against water to form nanoparticles with hydrophobic CPT molecules preferentially clustered in the core and mucic acid diols on the surface (FIG. 4(A)).

TABLE 1

Properties of MAP polymer and MAP-CPT polymer-drug conjugate

| Material | Property | Value |
|---|---|---|
| MAP Polymer | dn/dc (mL/g) | 0.14 |
| | MW$^a$ (kDa) | 68 |
| | Polydispersity$^b$ | 1.26 |
| MAP-CPT conjugate | Wt % CPT | 12. |

$^a$MW, molecular weight determined as $(M_w + M_n)/2$; $M_w$, weight average molecular weight; $M_n$, number average molecular weight.
$^b$Polydispersity determined as $M_w/M_n$.

Example 2. Materials and Methods $^1$H NMR spectra were acquired on a Varian 600 MHz spectrometer (Inova). Electrospray ionization (ESI) masses of small molecules were acquired on a Finnigan LCQ ion trap mass spectrometer. Matrix-assisted laser desorption/ionization-time-of-flight (MALDI-TOF) mass spectra for polymers were acquired on an Applied Biosystems Voyager DE-PRO.

Example 2.1 Synthesis of MAP-CPT Conjugate

Synthesis of Mucic Acid Dimethyl Ester. Methanol (360 mL) was added to mucic acid (15 g, 1 equiv, Alfa Aesar) in a 500 mL round-bottomed flask. To this was added concentrated sulfuric acid (1.2 mL, 0.3 equiv). The suspension was stirred and refluxed at 85° C. overnight. The mixture was cooled to room temperature and filtered through a Buchner funnel using Whatman Grade 5 filter paper. The solid was washed with methanol (600 mL), and recrystallized with a mixture of methanol (240 mL) and triethylamine (1.5 mL) at 85° C. for 1 h. The mixture was again cooled to room temperature and filtered. The solid was washed with methanol (600 mL), and dried under vacuum at 75° C. overnight to yield mucic acid dimethyl ester (14.2 g) as a white solid. $^1$H NMR (600 MHz, DMSO-d$_6$): 4.91 (d, 2H), 4.80 (q, 2H), 4.28 (d, 2H), 3.78 (q, 2H), 3.63 (s, 6H). ESI/MS: 261.0 [M+Na]$^+$.

Synthesis of N-Boc-Protected Mucic Acid Ethylenediamine. Methanol (225 mL) was added to mucic acid dimethyl ester (14.2 g, 1 equiv) in a 500 mL round-bottomed flask. To this was added triethylamine (21.7 mL, 2.6 equiv), and the mixture was stirred and refluxed at 85° C. for 30 min, forming a yellow suspension. N-Boc-ethylenediamine (24.6 mL, 2.6 equiv, AK Scientific) in methanol (55 mL) was added, and the reaction was stirred and refluxed at 85° C. overnight. The mixture was cooled to room temperature, and filtered through a Buchner funnel using Whatman Grade 5 filter paper. The solid was washed with methanol (750 mL), and recrystallized with methanol (350 mL) at 85° C. for 1.5 h. The mixture was again cooled to room temperature and filtered. The solid was washed with methanol (750 mL), and dried under vacuum at 75° C. overnight to yield N-Boc-protected mucic acid ethylenediamine (19.2 g) as a white solid. $^1$H NMR (600 MHz, DMSO-d$_6$): 7.71 (t, 2H), 6.81 (t, 2H), 5.13 (d, 2H), 4.35 (q, 2H), 4.09 (d, 2H), 3.77 (q, 2H), 3.12 (m, 4H), 2.98 (m, 4H), 1.36 (s, 18). ESI/MS: 517.1 [M+Na]$^+$.

Synthesis of Mucic Acid Ethylenediamine. N-Boc-protected mucic acid ethylenediamine (19.2 g) in a 500 mL round-bottomed flask was placed in a water bath. 3 N hydrochloric acid in methanol (325 mL) was added, and the reaction flask was sealed and vented with a needle. The suspension was stirred at 25° C. for 8 h. The slurry was filtered through a glass frit with a fine grain, and washed with methanol (900 mL) until the filtrate pH was close to neutral. The solid was dried under vacuum at 80° C. overnight to yield mucic acid ethylenediamine (11.5 g) as a white solid. $^1$H NMR (600 MHz, DMSO-d$_6$): 7.97-7.84 (m, 8H), 5.30 (d, 2H), 4.58 (d, 2H), 4.16 (d, 2H), 3.82 (m, 2H), 3.39-3.32 (m, 4H), 2.85 (m, 4H). ESI/MS: 295.0 [M+H]$^+$.

Synthesis of Mucic Acid Di(Asp(OBzl)-Boc). Mucic acid ethylenediamine (3 g, 1 equiv) was dissolved in 30 mL DMSO in a 250 mL round-bottomed flask. To this was added Boc-Asp(OBzl)-OSu (10.3 g, 3 equiv, Bachem) in acetonitrile (80 mL) and pyridine (3.2 mL, 5 equiv). The reaction was stirred and refluxed at 60° C. overnight. The mixture was cooled to room temperature, and acetonitrile was removed by rotary evaporation. The solution was precipitated by addition of nanopure water, and the precipitate was recrystallized with nanopure water (100 mL) at 85° C. for 1 h. The mixture was cooled to room temperature, filtered through a glass frit with a fine grain, and washed with nanopure water (200 mL). The recrystallization procedure was repeated with acetonitrile. The solid was dried under vacuum at 50° C. overnight to yield mucic acid di(Asp (OBzl)-Boc) (2.1 g) as a white solid. $^1$H NMR (600 MHz, DMSO-d$_6$): 7.94 (t, 2H), 7.76 (t, 2H), 7.37-7.31 (m, 10H), 7.06 (d, 2H), 5.13-5.08 (m, 6H), 4.37-4.32 (d, 2H), 4.30-4.28 (d, 2H), 4.14-4.12 (d, 2H), 3.81-3.79 (d, 2H), 3.18-3.09 (m, 8H), 2.79-2.57 (m, 4H), 1.38 (s, 18H). ESI/MS: 905.0 [M+H]$^+$.

Synthesis of Mucic Acid Di(Asp(OBzl)-amine). Dichloromethane (18 mL) was added to mucic acid di(Asp(OBzl)-Boc) (2.1 g, 1 equiv) in a 50 mL round-bottomed flask vented with argon. The flask was cooled to 0° C. in an ice bath, and trifluoroacetic acid (6 mL, 36 equiv) was added dropwise. The reaction was stirred for 8 h under argon, slowly equilibrating to room temperature. Solvent was removed by rotary evaporation. The solid was dissolved in dichloromethane (30 mL) and dried by rotary evaporation twice more, and then recrystallized with tetrahydrofuran (30 mL) at 55° C. for 1 h. The mixture was cooled to room temperature and filtered through a glass frit with a fine grain. The solid was washed with tetrahydrofuran (100 mL), and dried under vacuum at 50° C. overnight to yield mucic acid di(Asp(OBzl)-amine) (1.4 g) as a white solid. $^1$H NMR (600 MHz, DMSO-d$_6$): 8.46 (t, 2H), 8.21 (s, 6H), 7.80 (t, 2H), 7.39-7.35 (m, 10H), 5.19-5.16 (t, 2H), 5.13 (s, 4H), 4.41 (s, 2H), 4.15-4.13 (d, 2H), 4.06-4.04 (d, 2H), 3.83 (s, 2H), 3.22-3.16 (m, 8H), 3.02-2.83 (m, 4H). ESI/MS: 705.3 [M+H]+.

Synthesis of Mucic Acid Di(Asp-amine). Methanol (50 mL) was added to mucic acid di(Asp(OBzl)-amine) (1.4 g, 1 equiv) and 20% (w) palladium hydroxide on carbon (568 mg, 10 equiv) in a 100 mL round-bottomed flask. The reaction flask was sealed and vented with argon for 30 min. Hydrogen gas was added by a double-layered balloon, and the reaction was stirred for 24 h at room temperature. Catalyst was separated by centrifugation at 3220 g for 15 min, and the solvent removed by rotary evaporation. The solid was reconstituted in nanopure water, and the solution was filtered through a 0.2 µm Supor membrane Acrodisc syringe filter (Pall) and lyophilized to yield mucic acid di(Asp-amine) (1.1 g) as a white solid. $^1$H NMR (600 MHz, DMSO-d$_6$): 8.39 (t, 2H), 8.18 (broad, 6H), 7.77 (t, 2H), 5.18 (t, 2H), 4.46 (s, 2H), 4.12 (s, 2H), 3.96-3.94 (m, 2H), 3.79 (s, 2H), 3.21-3.11 (m, 8H), 2.84-2.65 (m, 4H). ESI/MS: 525.2 [M+H]$^+$. The product was stored under argon at −20° C.

Synthesis of Mucic Acid Polymer (MAP). Mucic acid di(Asp-amine) (220 mg, 1 equiv) and di(succinimidyl propionate)-PEG (3.4 kDa, 1 g, 1 equiv, JenKem) were equilibrated to room temperature for 1 h, then added to an oven-dried 10 mL round-bottomed flask. The reaction flask was sealed, and the two solids were dried under vacuum for 4 h. Anhydrous dimethyl sulfoxide (7 mL) was added under argon to dissolve the two solids. To this was added anhydrous N,N-diisopropylethylamine (205 μL, 4 equiv) dried over molecular sieves, and the solution was stirred under argon at room temperature for 42 h. The solution was dialyzed against dimethyl sulfoxide and nanopure water using a 10 kDa MWCO Spectra/Por 7 membrane (Spectrum), filtered through a 0.2 μm Supor membrane Acrodisc syringe filter (Pall) and lyophilized to yield MAP (983 mg) as a white, sponge-like solid. $^1$H NMR (600 MHz, DMSO-d$_6$): 8.11 (d, 1H), 8.08 (d, 1H), 7.83 (t, 1H), 7.79 (t, 1H), 7.73 (t, 2H), 4.49 (td, 2H), 4.14 (d, 2H), 3.69 (ddt, 2H), 3.59 (t, 4.3H), 3.53-3.43 (s-PEG), 3.18-3.07 (m, 8H), 2.61-2.43 (m, 4H), 2.38 (t, 4.3H).

Determination of MAP Molecular Weight. Polymer molecular weight was determined on a gel permeation chromatography (GPC) system equipped with an Agilent 1100 HPLC with binary pump and injector with 2 size exclusion columns in series (PL aquagel-OH 40 8 μm, Agilent) connected to Wyatt DAWN HELEOS light scattering and Wyatt Optilab rEX refractive index detectors. MAP was dissolved at six different concentrations in PBS, pH 7.4 and directly injected into the refractive index detector at 0.2 mL/min using a syringe pump to determine specific refractive increment, dn/dc. Absolute molecular weight was determined by injecting 100 μL of MAP dissolved at 4 mg/mL in PBS, pH 7.4 onto the column. PBS was used as the eluent at a flow rate of 0.7 mL/min, and the detected polymer peak was analyzed using ASTRA V Software.

Synthesis of MAP-CPT Conjugate. MAP was prepared and characterized as follows. Anhydrous dimethyl sulfoxide (10 mL) was added under argon to dissolve MAP (200 mg, 1 equiv) in a 25 mL round-bottomed flask. To this was added EDC (83 mg, 4 equiv) and NHS (32 mg, 3 equiv) dissolved in anhydrous dimethyl sulfoxide (3 mL), followed by 20-O-glycincamptothecin trifluoroacetic acid salt (CPT-gly·TFA, 170 mg, 3 equiv) dissolved in dimethyl sulfoxide (3 mL) and anhydrous N,N-diisopropylethylamine (56 μL) dried over molecular sieves. The reaction was stirred under argon at room temperature overnight. The solution was dialyzed against dimethyl sulfoxide 3 times and nanopure water 2 times using a 10 kDa MWCO Spectra/Por 7 membrane (Spectrum). Precipitate was removed by centrifugation at 3220 g for 15 min, and the supernatant was filtered through a 0.2 m Supor membrane Acrodisc syringe filter (Pall) to yield MAP-CPT conjugate as self-assembled nanoparticles in solution. A portion of this clear yellow solution was lyophilized to determine percent CPT conjugation. The remaining product was formulated into 0.9% (w/v) saline and stored at −20° C.

Determination of CPT Content in MAP-CPT. Lyophilized MAP-CPT was dissolved in dimethyl sulfoxide at 10 mg/mL, diluted to 0.1 mg/mL with 1 N NaOH, and incubated overnight. Fluorescence was measured at 370/440 nm (ex/em) using a Safire 2 multi-mode plate reader (Tecan). A calibration curve of known concentrations of CPT was prepared and used to determine the CPT concentration in the mixture.

Example 2.2. Synthesis of MAP-AF568 Conjugate

Anhydrous dimethyl sulfoxide (3 mL) was added under argon to dissolve MAP (30 mg, 1 equiv) in a 10 mL round-bottomed flask. To this was added EDC (13 mg, 4 equiv) and NHS (5 mg, 3 equiv) dissolved in anhydrous dimethyl sulfoxide (1 mL), followed by Alexa Fluor 568 hydrazide, sodium salt (AF568, 12 mg, 1 equiv) dissolved in dimethyl sulfoxide (1 mL). The reaction was stirred under argon at room temperature overnight. The solution was dialyzed against dimethyl sulfoxide 3 times and nanopure water 4 times using a 10 kDa MWCO Spectra/Por 7 membrane (Spectrum). The retentate was filtered through a 0.2 m Supor membrane Acrodisc syringe filter (Pall) to yield MAP-AF568 conjugate as self-assembled nanoparticles in solution. The product was then formulated into 0.9% (w/v) saline and stored at −20° C.

Example 2.3. Synthesis of CO$_2$H-PEG3.5k-nitroPBA and CO$_2$H-PEG5k-nitroPBA

Synthesis of 3-acyl chloride-5-nitrophenyl boronic acid. 3-carboxy-5-nitrophenyl boronic acid (nitroPBA, 100 mg, 1 equiv, Alfa Aesar) was added to an oven-dried 10 mL round-bottomed flask. The reaction flask was sealed and vented with argon. Anhydrous tetrahydrofuran with BHT inhibitor (4 mL) was added to dissolve the boronic acid, followed by anhydrous dimethylformamide (7 μL, 0.2 equiv). The flask was cooled to 0° C. in an ice bath, and oxalyl chloride (98 μL, 2.4 equiv) was added dropwise. After addition of oxalyl chloride, the ice bath was removed and the reaction was stirred under argon for 2 hrs. Solvent was evaporated under vacuum to yield 3-acyl chloride-5-nitrophenyl boronic acid (101 mg) as a yellow solid.

Synthesis of CO$_2$H-PEG3.5k-nitroPBA. 3-acyl chloride-5-nitrophenyl boronic acid (46 mg, 2 equiv) was added to an oven-dried 25 mL round-bottomed flask. The reaction flask was sealed, vented with argon, and cooled to 0° C. in an ice bath. Anhydrous DCM (5 mL was added to dissolve the boronic acid. Acetic acid-PEG3.5k-amine (3.5 kDa, 350 mg, 1 equiv, JenKem) was added to a separate oven-dried 10 mL round-bottomed flask. The flask was sealed and vented with argon. To this was added anhydrous N,N-diisopropylethylamine (35 μL, equiv) dried over molecular sieves, and anhydrous DCM (5 mL) to dissolve the PEG. The PEG solution was added dropwise to the boronic acid solution. The reaction flask was left in the ice bath to slowly warm to room temperature and stirred under argon overnight protected from light. Solvent was removed under vacuum, and the solid reconstituted in 0.5 N HCl (4 mL) and stirred for 15 min. The solution was filtered through a 0.2 m Supor membrane Acrodisc syringe filter (Pall) and dialyzed against nanopure water until constant pH using a 1 kDa MWCO Spectra/Por 7 membrane (Spectrum). The retentate was filtered through a 0.2 m Durapore PVDF membrane Millex syringe filter (Millipore), and lyophilized to yield CO$_2$H-PEG3.5k-nitroPBA (238 mg) as a white solid. $^1$H NMR (600 MHz, DMSO-d$_6$): 12.52 (s-COOH, 1H), 8.90 (t, 1H), 8.72 (m, 1H), 8.69 (m, 1H), 8.64 (m, 1H), 8.61 (s, 2H), 4.01 (s, 2H), 3.53-3.46 (s-PEG). MALDI: 3978.4.

Synthesis of CO2H-PEG5k-nitroPBA.

A similar synthesis procedure was followed using acetic acid-PEG5k-amine (5 kDa, 500 mg, 1 equiv, JenKem) to synthesize CO2H-PEG5k-nitroPBA. Solvent was removed under vacuum, and the solid reconstituted in 0.5 N HCl (5 mL) and stirred for 15 min. The solution was filtered through a 0.2 m Supor membrane Acrodisc syringe filter (Pall) and dialyzed against nanopure water until constant pH using a 15 mL Amicon Ultra 3 kDa spin filter (Millipore). The retentate was filtered through a 0.2 m Durapore PVDF membrane Millex syringe filter (Millipore), and lyophilized to yield CO2H-PEG5k-nitroPBA (452 mg) as a white solid. $^1$H NMR (600 MHz, DMSO-$d_6$): 12.52 (s-COOH, 1H), 8.90 (t, 1H), 8.73 (m, 1H), 8.68 (m, 1H), 8.65 (m, 1H), 8.62 (s, 2H), 4.00 (s, 2H), 3.53-3.46 (s-PEG). MALDI: 5476.7.

A similar procedure was followed using methoxy-PEG-amine (5 kDa, 500 mg, 1 equiv, JenKem) to synthesize OMe-PEG-nitroPBA. $^1$H NMR (600 MHz, DMSO-$d_6$): 8.90 (t, 1H), 8.72 (m, 1H), 8.69 (m, 1H), 8.64 (m, 1H), 8.60 (s, 2H), 3.54-3.48 (s-PEG), 3.23 (s, 2H). MALDI: 5825.4.

Example 2.4. Synthesis of Herceptin-PEG3.5k-nitroPBA and Tf-PEG5k-nitroPBA

Synthesis of Herceptin-PEG3.5k-nitroPBA. CO2H-PEG3.5k-nitroPBA (11.2 mg, 25 equiv), EDC-HCl (6.1 mg, 250 equiv), and NHS (5.5 mg, 375 equiv) were dissolved in 0.1 M MES buffer, pH 6.0 (0.33 mL), and stirred for 15 min at room temperature. The reaction mixture was then added to a 0.5 mL Amicon Ultra 3 kDa spin filter (Millipore), and centrifuged to isolate the activated nitroPBA-PEG3.5k-NHS ester. The ester was added to Herceptin (20 mg, 1 equiv) dissolved in 0.1 M PBS, 0.15 M NaCl, pH 7.4 (1 mL). The reaction was lightly agitated for 2 h at room temperature, and then dialyzed against 0.1 M PBS, 0.15 M NaCl, pH 7.4 using 0.5 mL Amicon Ultra 50 kDa spin filters (EMD Millipore) to remove excess PEG. A portion of this solution was dialyzed into 10 mM PB, pH 7.4, and conjugation was verified by MALDI-TOF using a sinapinic acid matrix. MALDI: 153063.6. The remaining Herceptin-PEG3.5k-nitroPBA was formulated into PBS, pH 7.4, and stored at 4° C.

Synthesis of Tf-PEG5k-nitroPBA. A similar procedure was followed using CO2H-PEG5k-nitroPBA (16 mg, 25 equiv) and human holo-Tf (10 mg, 1 equiv, Sigma) to prepare Tf-PEG5k-nitroPBA. Following dialysis against 0.1 M PBS, 0.15 M NaCl, pH 7.4 to remove excess PEG, the amount of iron loaded to the Tf after conjugation was verified by UV-VIS on a NanoDrop system (Thermo Scientific) using the ratio of A465/A280. This ratio was compared to that of the unreacted human holo-Tf, and a value ≥80% of the unreacted ratio confirmed adequate iron retention following synthesis steps. A portion of this solution was dialyzed into 10 mM PB, pH 7.4, and conjugation was verified by MALDI-TOF using a sinapinic acid matrix. MALDI 85210.7. The remaining Tf-PEG5k-nitroPBA was formulated into PBS, pH 7.4, and stored at 4° C.

Example 2.5. Preparation of Nanoparticles

To prepare TfR-targeted CPT nanoparticles, Tf-PEG5k-nitroPBA conjugates in PBS, pH 7.4 were added at 20× molar excess to MAP-CPT nanoparticles (20 Tf per particle). The solution was gently mixed by pipette and allowed to equilibrate for 10 min. To prepare Herceptin and combination CPT/Herceptin nanoparticles, Herceptin-PEG3.5k-nitroPBA conjugates in PBS, pH 7.4 were added at an equal molar ratio to either MAP-AF568 or MAP-CPT nanoparticles (1 Herceptin per particle), respectively. The solution was gently mixed and allowed to equilibrate as above. Tf-PEG5k-nitroPBA conjugates in PBS, pH 7.4 were then added at 20× molar excess to either Herceptin or combination CPT/Herceptin nanoparticles (20 Tf per particle) to form TfR-targeted Herceptin and TfR-targeted combination CPT/Herceptin nanoparticles, respectively. The solution was again mixed by pipette and allowed to equilibrate for 10 min. Nanoparticle formulations were filtered using a 0.45 m PTFE membrane Millex syringe filter (Millipore).

An analogous procedure was used with OMe-PEG-nitroPBA was used to prepare the corresponding non-targeted nanoparticles.

Example 2.6. Nanoparticle Characterization

Nanoparticles were characterized using a Brookhaven Instruments Corporation (BIC) ZetaPALS. Nanoparticles were diluted in PBS, pH 7.4 and hydrodynamic diameter was measured by dynamic light scattering (DLS) using BIC Particle Sizing Software. Particle formulations were diluted in 10 mM PB, pH 7.4 and zeta potential was measured using BIC PALS Zeta Potential Analyzer software with a target residual of 0.02. Five runs were performed for both the nanoparticle diameter and zeta potential measurements.

Example 2.7. Antitumor Efficacy

Intracardiac (ICD) Brain Metastasis Model. All animals were treated according to the NIH guidelines for animal care and use as approved by the Caltech Institutional Animal Care and Use Committee. BT474-Gluc cells, transduced with an expression cassette encoding Gluc and CFP separated by an internal ribosomal entry site using a lentiviral vector, were obtained from Dr. Jain at Harvard University. BT474-Gluc cells were maintained in RPMI 1640 supplemented with 10% (v/v) FBS in a humidified oven at 37° C. with 5% $CO_2$. 100,000 BT474-Gluc cells were suspended in 100 μL of RPMI and slowly injected into the left ventricle of female Rag2−/−; Il2rg−/− mice. Injections were performed blind, midway between the sternal notch and top of xyphoid process, and 13% anatomical left of sternum. Successful insertion into the left cardiac ventricle was confirmed by a bright red pulse of blood in the syringe. See FIGS. 5(A-C).

For the IC model, 50,000 BT474-Gluc cells in 2 μL RPMI were intracranially injected into the right cerebral hemisphere of female Rag2−/−; Il2rg−/− mice (Jackson Laboratory) using a stereotaxic apparatus at a rate of 0.1 μL/min. The coordinates for injection were 2 mm posterior, 1.5 mm lateral to bregma, and 2.5 mm depth from bregma. For the IV model, 2 M cells were suspended in 150 μL RPMI and slowly injected into the lateral tail vein of restrained female Rag2−/−; Il2rg−/− mice.

Tumor Size Monitoring. For ICD and IV models, formation of BT474-Gluc brain metastatic tumors was monitored by MRI every third week until macroscopic tumors were visible (~0.2 mm$^3$ in volume). Tumor growth was then monitored weekly by MRI, as for the IC model. Mice were anaesthetized with 1.5-2% (v/v) isoflurane in $O_2$ at a flow rate of 1-1.5 mL/min. T2-weighted 3D RARE images were acquired to assess the tumor volume. The image acquisition parameters were as follows: echo time: 6.1 ms; repetition time: 250 ms; rapid acquisition relaxation enhanced (RARE) factor: 4; number of averages: 4; field of view: 2.0 cm×1.2 cm×0.8 cm; matrix: 200×120×80 (100 m isotropic resolution). Tumor volume was determined manually from the T2 hyperintense tumor regions of the brain using Fiji software. For the IC model, tumor size was also monitored by measuring the activity of secreted Gluc in the blood. 20 μL of blood was collected weekly from the saphenous vein, mixed with 5 μL of 50 mM EDTA, and immediately frozen at −20° C. until time for analysis. Blood was transferred to an opaque 96-well plate (Nunc), and Gluc activity measured using the Pierce Gaussia Luciferase Flash Assay Kit, according to the manufacturer's protocol. Photon counts were acquired for 5 s following addition of coelenterazine using a Safire 2 multi-mode plate reader (Tecan). Pairwise group comparisons testing for statistically significant differences were performed using the Wilcoxon-Mann-Whitney test in MATLAB.

Treatments. Treatment began when brain metastatic tumors reached ~2 mm$^3$, as measured by MRI. Mice in each model were randomized into four groups of six mice per group. CPT at a dose of 4 mg/kg (in 20% DMSO, 20% PEG 400, 30% ethanol, and 30% 10 mM pH 3.5 phosphoric acid), Herceptin at 24 mg/kg (in PBS, pH 7.4), TfR-targeted CPT nanoparticles at 4 mg/kg (CPT basis, in PBS, pH 7.4), TfR-targeted Herceptin nanoparticles at 24 mg/kg (Herceptin basis, in PBS, pH 7.4), and TfR-targeted combination CPT/Herceptin nanoparticles at 4 and 24 mg/kg (CPT and Herceptin bases, respectively, in PBS, pH 7.4) were freshly prepared. The different formulations were systemically administered by lateral tail vein injection once per week for 4 weeks. Injections were standardized to 150 μL per 20 g body weight. The control treatment was 0.9% (w/v) saline. No gross signs of toxicity were observed from either the non-targeted or the targeted nanoparticles in these studies, though animals did have reactions to dosing with CPT alone.

Specific Binding of TfR Allows Targeted Nanoparticles to Cross an in Vitro Model of the BBB. To perform an initial screen of transcytosis capacity, we used the bEnd.3 immortalized mouse brain endothelial cell line in an established in vitro model of the BBB. Nanoparticles were added to the apical compartment of bEnd.3-coated transwells in serum-free DMEM and allowed to cross the model BBB for 8 h, after which the full volume of the basal compartment was removed and CPT content measured using HPLC.

Figure 6:
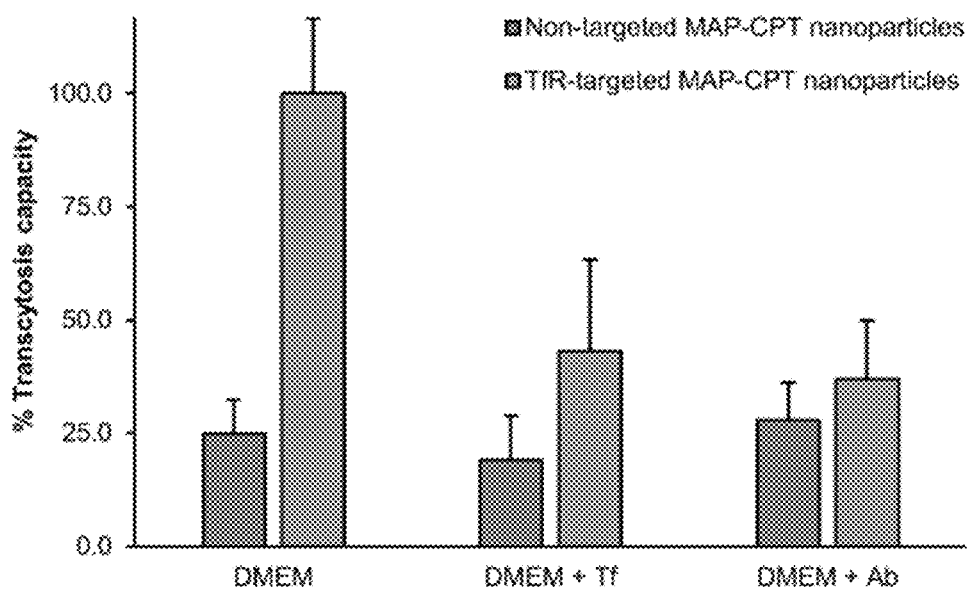
FIG. 6 shows apical to basal transport of non-targeted and TfR-targeted MAP-CPT nanoparticles in model BBB. TfR-targeted (blue) and non-targeted (gray) nanoparticles were added to apical wells in either serum-free DMEM (DMEM), or in the presence of either 2.5 mg/mL Tf (DMEM+Tf) or equimolar high-affinity anti-TfR Ab (DMEM+Ab). Data shown are the average of 4 wells for each group. Error bars indicate SE.

After 8 h, TfR-targeted MAP-CPT nanoparticles showed a significantly increased capacity to cross the bEnd.3 cells compared to non-targeted nanoparticles (FIG. 6). In addition, TfR-targeted nanoparticles showed a decreased ability to cross the model BBB when coincubated with serum concentrations of Tf, indicating TfR binding is essential to crossing. Interestingly, when coincubated with an equimolar amount of high affinity anti-TfR Abs, TfR-targeted nanoparticles also revealed a decreased ability to cross the transwells, consistent with previous reports of high-affinity Ab:TfR interactions leading to lysosomal trafficking.

Figure 5A:
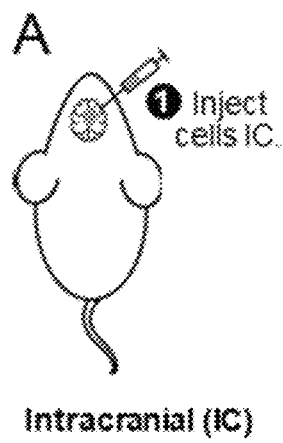
FIG. 5(A): Intracranial (IC) injection of tumor cells allows for direct establishment of brain metastases.
Figure 5B:
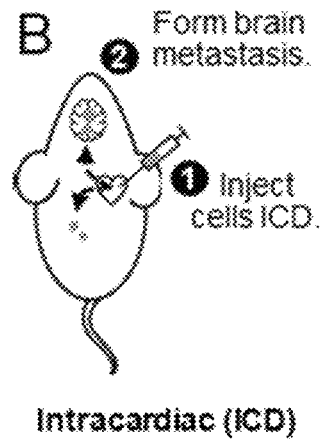
FIG. 5(B): Following intracardiac (ICD) injection into the left ventricle, tumor cells can head to brain vasculature, as well as to other organs. Some cells will successfully extravasate and form macroscopic brain tumors.
Figure 5C:
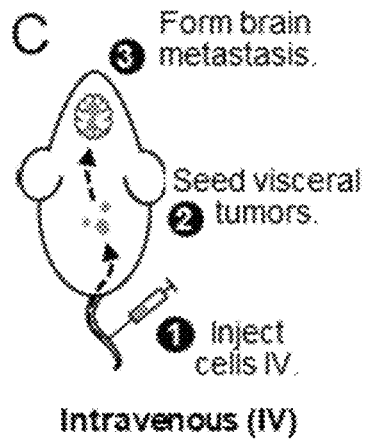
FIG. 5(C): After intravenous (IV) injection, most tumor cells will arrest in the lung capillary bed, as well as other sites, followed by subsequent metastasis to the brain.

Development of Mouse Model that Replicates the Metastasis Process in HER2-Positive Breast Cancer Brain Metastasis Patients. In an attempt to create a clinically representative, impermeable barrier to standard therapeutics, we developed a new model of HER2-positive breast cancer brain metastasis that reproduces human cancer dissemination. Metastasis models are illustrated in FIG. 5. HER2-positive BT474-Gluc cells were intravenously (IV) injected into Rag2$^{-/-}$; Il2rg$^{-/-}$ mice, and formation of brain metastases was monitored by MRI. This cell line was engineered to express Gaussia luciferase (Gluc) that can be used as a surrogate for tumor burden (29). Rag2$^{-/-}$; Il2rg$^{-/-}$ mice were chosen because they have shown the ability to allow multi-organ metastatic spread of HER2-positive breast cancer cell lines injected IV.

Figure 7A:
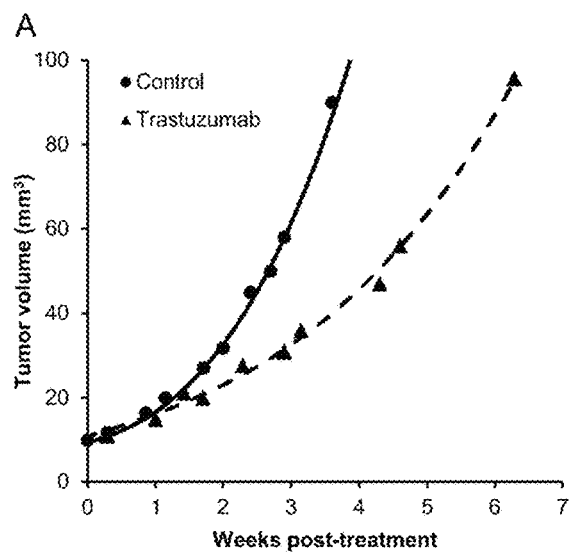
FIGS. 7(A-B) show the effect of anti-HER2 therapy on HER2-positive BT474-Gluc breast cancer brain metastases established in $Rag2^{-/-}$; $Il2rg^{-/-}$ mice. Trastuzumab at 5 mg/kg was administered twice weekly via intravenous tail vein injection, and treatment was initiated when tumors reached 10 mm$^3$ in volume. MRI was used to monitor brain tumor size and response to treatment. Tumors established by IC injection (FIG. 7(A)) showed significant delay in tumor progression, whereas those established by IV injection (FIG. 7(B)) did not.
Figure 7B:
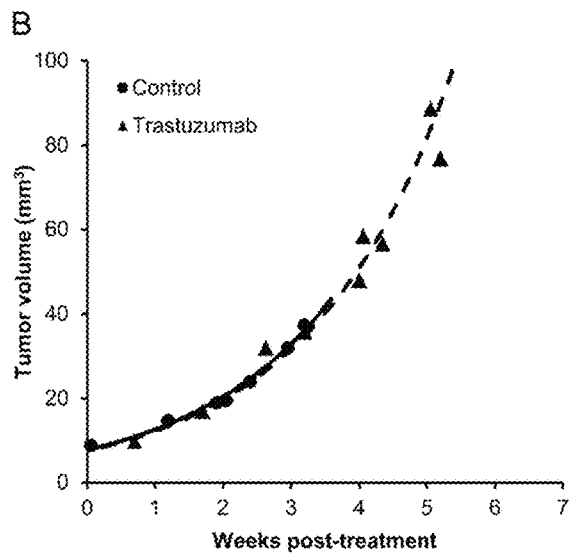

IV injection of BT474-Gluc cells reproduced the metastatic pattern observed in breast cancer patients, with multiple metastatic sites (Table 2). Importantly, brain tumors developed in a majority of the mice (>90%) before they succumbed to visceral tumor burden, with a distribution similar to that observed in patients. The median time to establishment of brain metastatic tumors visible by MRI was 4.2 months (range 2.9-6.1 months). We tested the effects of a standard anti-HER2 therapy, trastuzumab, on the growth of BT474-Gluc tumors established by IV injection versus the commonly used intracranial (IC) method. Treatment with trastuzumab led to delay in tumor progression when tumors were established by IC injection, suggesting this method of forming brain tumors may disrupt the BBB/BTB (FIGS. 7(A-B)). In contrast, trastuzumab failed to control tumor growth for tumors established IV, mimicking the clinical situation.

TABLE 2

Metastatic ability of human BT474-Gluc breast cancer cells in Rag2$^{-/-}$; Il2rg$^{-/-}$ mice following IV injection.

| Brain | Lung | Bone | Liver | Ovary | Lymph | Other* |
|-------|------|------|-------|-------|-------|--------|
| 22/24 | 24/24 | 6/8 | 16/17 | 24/24 | 24/24 | 19/24 |

Metastasis incidence provided by site per number of mice for which tissue type was analyzed.
*Other metastatic sites included kidney, salivary glands, and interscapular space.

Figure 8:
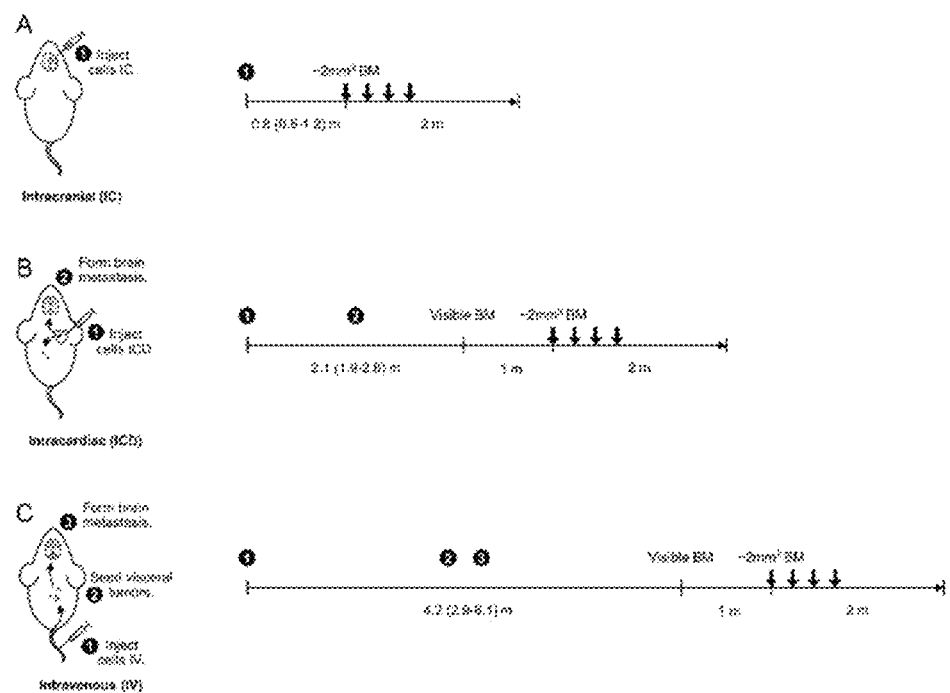
FIG. 8 provides a detailed illustration of intracranial (A), intracardiac (B), and intravenous (C) breast cancer brain metastasis models and timelines for efficacy study. Numbers below timeline indicate mean (range) time in months to establishment of visible brain metastases (BM; ~0.2 mm$^3$ in volume) by MRI. Thick arrows denote treatment schedule for the study, with 4 weekly doses administered once tumors reached ~2 mm$^3$ in volume.

Brain Tumors Show Significant Delay in Growth with TfR-Targeted Nanoparticles, but their Response Differs when Established by Different Methods. We compared the efficacy of TfR-targeted MAP-CPT nanoparticles, non-targeted MAP-CPT nanoparticles and CPT on the growth of BT474-Gluc brain metastatic tumors in Rag2$^{-/-}$; Il2rg$^{-/-}$ mice established by IC, ICD and IV methods (FIG. 8). After IC, ICD or IV injection of BT474-Gluc cells, formation of brain metastatic tumors was monitored by MRI. A total of six mice were used for each treatment group per model, and treatment was initiated when tumors reached 2 mm$^3$ in volume. This metastasis volume was chosen as an intermediate size between small micrometastases (0.1-1 mm$^3$) and large lesions (>4-10 mm$^3$). The different formulations were systemically administered by lateral tail vein injection once per week for 4 weeks at a dose of 4 mg/kg (CPT basis). Brain tumor volume was measured weekly by MRI. Blood Gluc activity was measured in addition only for the IC model, due to substantial extracranial tumor burden in the ICD and IV models.

Figure 9:
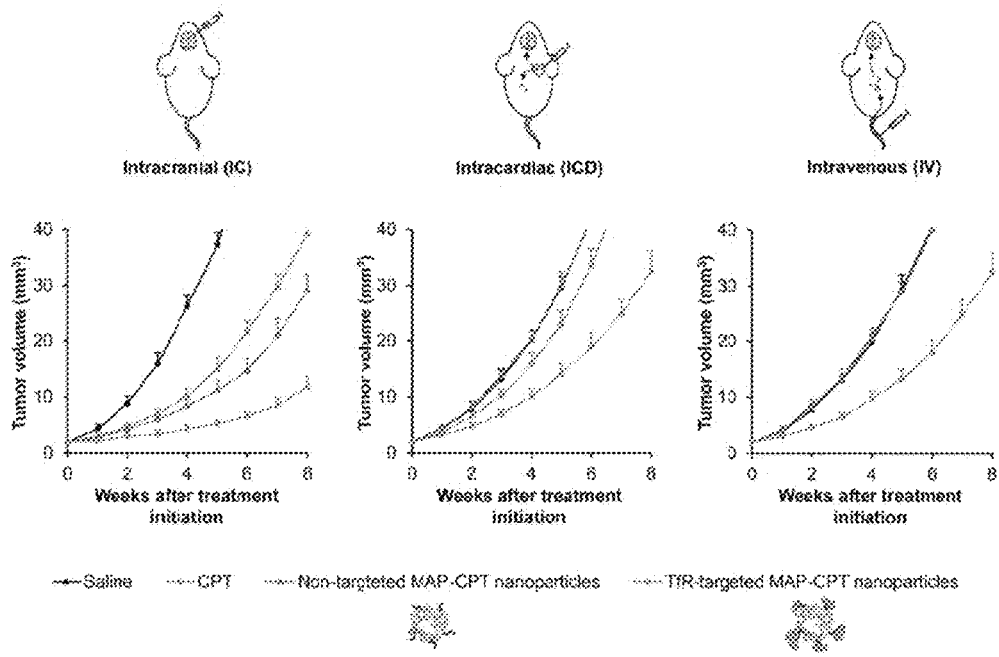
FIG. 9 shows data for brain tumors established using different methods show differential response to therapeutics. Tumor growth curves of BT474-Gluc metastatic brain tumors treated with CPT (orange, 4 mg/kg), non-targeted MAP-CPT nanoparticles (gray, 4 mg CPT/kg), and TfR-targeted MAP-CPT nanoparticles (blue, 4 mg CPT/kg) compared to saline (black) when established by IC (A), ICD (B), and IV injection (C). Data shown are the average of 6 mice per treatment group. Error bars indicate SE.
Figure 10:
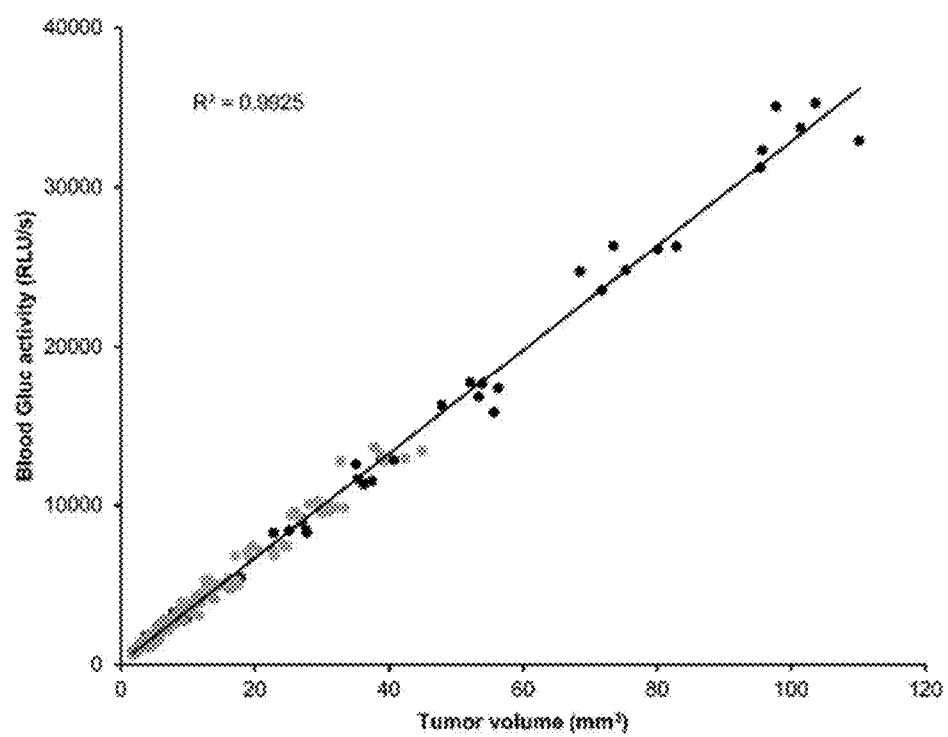
FIG. 10 shows blood Gluc activity of IC-established tumors is correlated with tumor volume, as measured by MRI, for each treatment group. Blood Gluc activity is plotted against tumor volume for saline (black), CPT (orange), non-targeted MAP-CPT nanoparticle (gray), and TfR-targeted MAP-CPT nanoparticle (blue) treatment groups. Linear regression was performed using MATLAB.
Figure 11A:
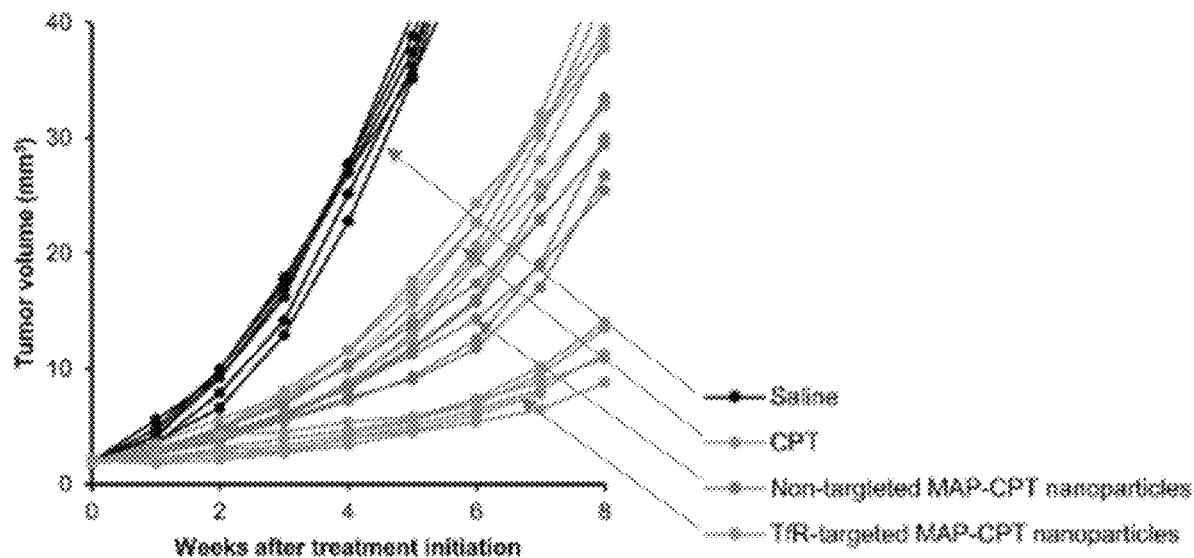
FIGS. 11(A-C) show individual tumor growth curves of BT474-Gluc metastatic brain tumors treated with CPT (orange, 4 mg/kg), non-targeted MAP-CPT nanoparticles (gray, 4 mg CPT/kg), and TfR-targeted MAP-CPT nanoparticles (blue, 4 mg CPT/kg) compared to saline (black) when established by IC (FIG. 11(A)), ICD (FIG. 11(B)), and IV injection (FIG. 11(C)). Open circles denote leptomeningeal metastases. 2 of 24 total metastases included in this study for both the ICD and IV models were leptomeningeal. All other brain tumors were intracerebral.
Figure 11B:
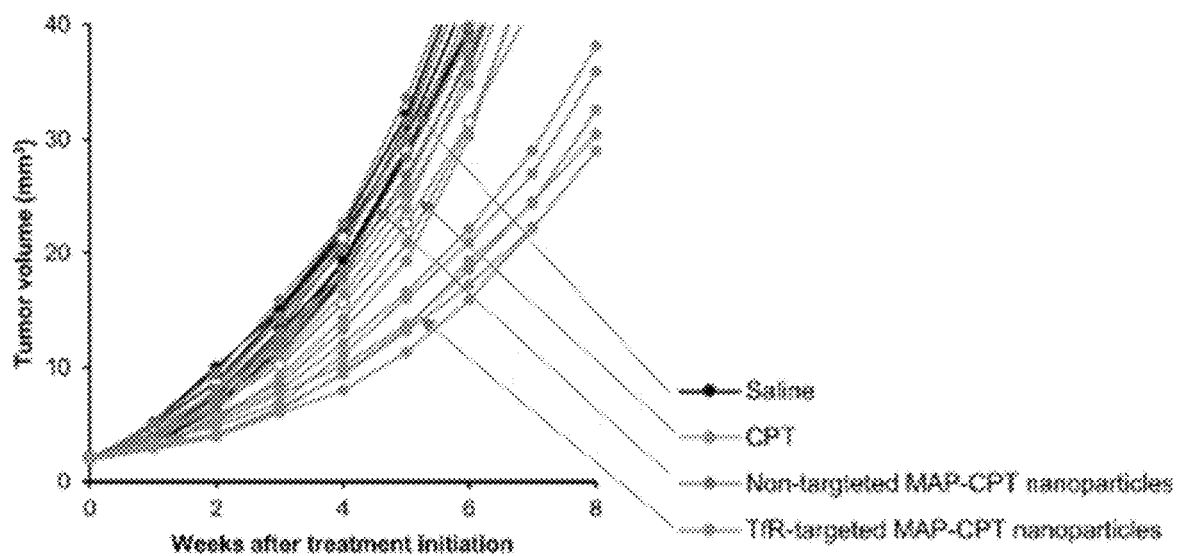
Figure 11C:
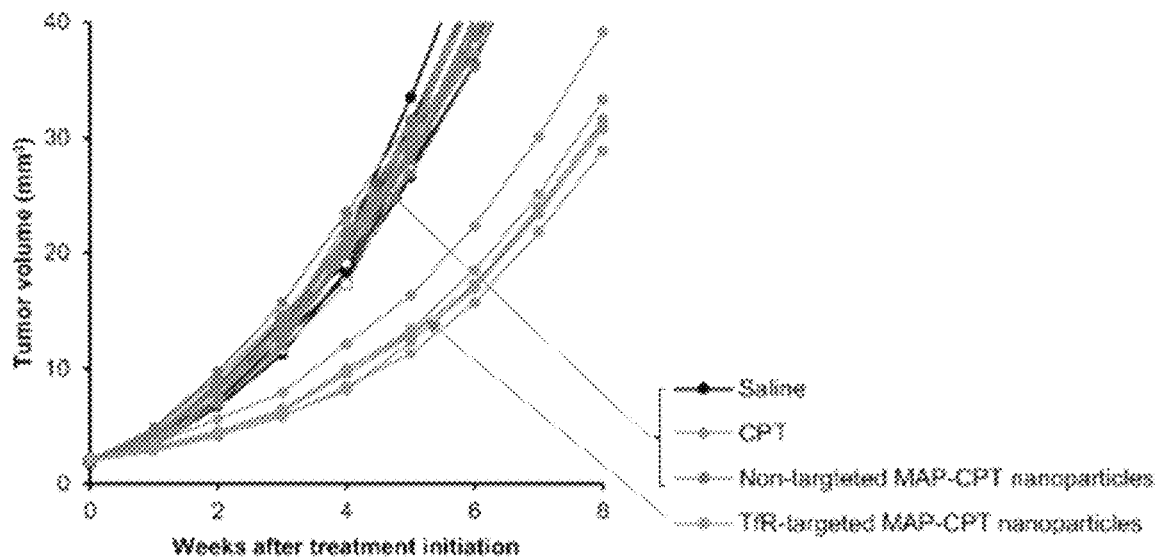

In mice bearing IC-established brain tumors, TfR-targeted MAP-CPT nanoparticles significantly delayed brain metastatic tumor growth compared to saline, resulting in an 8.4-fold decrease in mean tumor volume by the end of the study (FIG. 9 and Table 3). However, treatment with non-targeted MAP-CPT nanoparticles or CPT also led to substantial tumor growth inhibition (3.5- or 2.6-fold reduction in mean final tumor volume, respectively), supporting the hypothesis that artificial transport pathways may be introduced following IC tumor establishment. The blood Gluc activity for each treatment group correlated well with tumor volume, as measured by MRI (FIG. 10). Individual antitumor data are provided in FIGS. 11(A-C).

TABLE 3

Antitumor efficacy in Rag2$^{-/-}$; Il2rg$^{-/-}$ mice bearing human BT474-Gluc breast cancer metastatic brain tumors established by IC injection.

| | Mean tumor volume (mm$^3$) | Median tumor volume (mm$^3$) | P vs. saline |
|---|---|---|---|
| Saline | 101 | 100 | — |
| CPT (4 mg/kg) | 39 | 39 | 0.0022 |
| Non-targeted MAP-CPT nanoparticle (4 mg CPT/kg) | 29 | 30 | 0.0022 |
| TfR-targeted MAP-CPT nanoparticle (4 mg CPT/kg) | 12 | 12 | 0.0022 |

Data provided are mean and median tumor volumes at the end of the study. P values were calculated using the Wilcoxon-Mann-Whitney test.

TABLE 4

Antitumor efficacy in Rag2$^{-/-}$; Il2rg$^{-/-}$ mice bearing human BT474-Gluc breast cancer metastatic brain tumors established by ICD injection.

| | Mean tumor volume (mm$^3$) | Median tumor volume (mm$^3$) | P vs. saline |
|---|---|---|---|
| Saline | 87 | 88 | — |
| CPT (4 mg/kg) | 69 | 71 | 0.0022 |
| Non-targeted MAP-CPT nanoparticle (4 mg of CPT/kg) | 87 | 89 | 0.9372 |
| TfR-targeted MAP-CPT nanoparticle (4 mg of CPT/kg) | 33 | 32 | 0.0022 |

Data provided are mean and median tumor volumes at the end of the study. P values were calculated using the Wilcoxon-Mann-Whitney test.

TABLE 5

Antitumor efficacy in Rag2$^{-/-}$; Il2rg$^{-/-}$ mice bearing human BT474-Gluc breast cancer metastatic brain tumors established by IV injection.

| | Mean tumor volume (mm$^3$) | Median tumor volume (mm$^3$) | P vs. saline |
|---|---|---|---|
| Saline | 83 | 83 | — |
| CPT (4 mg/kg) | 86 | 86 | 0.5887 |
| Non-targeted MAP-CPT nanoparticle (4 mg of CPT/kg) | 84 | 84 | 0.9372 |
| TfR-targeted MAP-CPT nanoparticle (4 mg of CPT/kg) | 33 | 31 | 0.0022 |

Data provided are mean and median tumor volumes at the end of the study. P values were calculated using the Wilcoxon-Mann-Whitney test.

In contrast to results from the IC model, only treatment with TfR-targeted MAP-CPT nanoparticles resulted in substantial tumor growth delay compared to saline when tumors were established by ICD injection (2.6-fold decrease in mean tumor volume; FIG. 9(B) and Table 4). Interestingly, we observed a modest response with CPT treatment, but not with non-targeted MAP-CPT nanoparticles (although this difference was not significant).

Similar to the ICD model, with IV-established brain tumors, TfR-targeted MAP-CPT nanoparticles markedly slowed tumor growth compared to saline (2.5-fold decrease in mean tumor volume; FIG. 9(C) and Table 5). Notably, no tumor growth inhibition was observed with CPT or non-targeted MAP-CPT nanoparticles compared to saline in this model, more closely replicating the clinical situation.

Brain Uptake of Therapeutics Differs in Tumor, but not Healthy Tissue between Models. To ascertain whether differences in brain penetration of the therapeutics might explain the discordance in efficacy between brain metastasis models, we systemically administered an additional dose of each treatment at the end of the efficacy study. After 24 h, mice were anesthetized and perfused with PBS to clear any remaining nanoparticles or free drug from the bloodstream. Drug uptake into tumor and healthy brain tissue was quantified by HPLC as previously described.

Figure 12A:
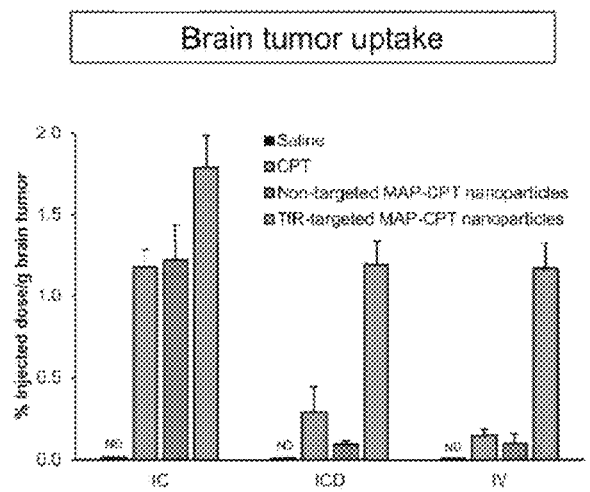
FIG. 12(A) shows brain uptake in BT474-Gluc tumor tissue as calculated by percent injected dose per g of tissue for different treatments.
Figure 12B:
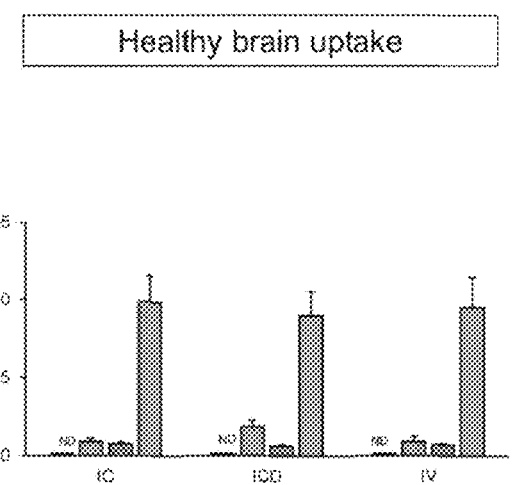
FIG. 12(B) Percent injected dose in healthy brain tissue. Brain uptake was determined 24 h after a 4 mg/kg dose (CPT basis). Data shown are the average of 4 mice per treatment group. Error bars indicate SE. ND, not detectable.
Figure 13:
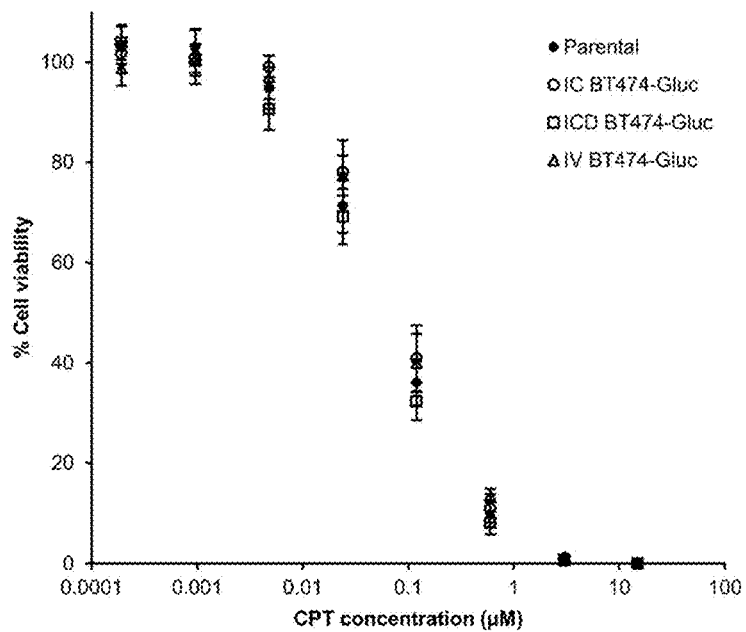
FIG. 13 shows BT474-Gluc cells isolated from brain tumors following IC-(circle), ICD-(square), and IV-establishment (triangle) as well as parental cells (solid circle) are similarly sensitive to CPT. Data shown are the average of 4 dose-response curves for each cell line. Error bars indicate SE.

Tumor tissue collected from IC-established, but not from ICD- and IV-established brain tumors showed significant accumulation of CPT and non-targeted MAP-CPT nanoparticles, consistent with the hypothesis that the barrier in IC-established tumors may be more permeable to therapeutics than what is observed in patients with HER2-positive disease (FIGS. 12(A-B)). In addition, cells isolated from BT474-Gluc tumors from all three models as well as the respective parental cells had comparable sensitivities to CPT in vitro (SI Appendix, FIG. 13), ruling out permanent, model-specific drug sensitivity as the origin for anti-tumor differences. Although there is evidence that brain-specific drug resistance mechanisms may also be important (7), these data strongly implicate BBB/BTB permeability to the therapeutic agents as a key mediator of the differential treatment response between the models in this study.

Example 3. Results and Discussions

Figure 14A:
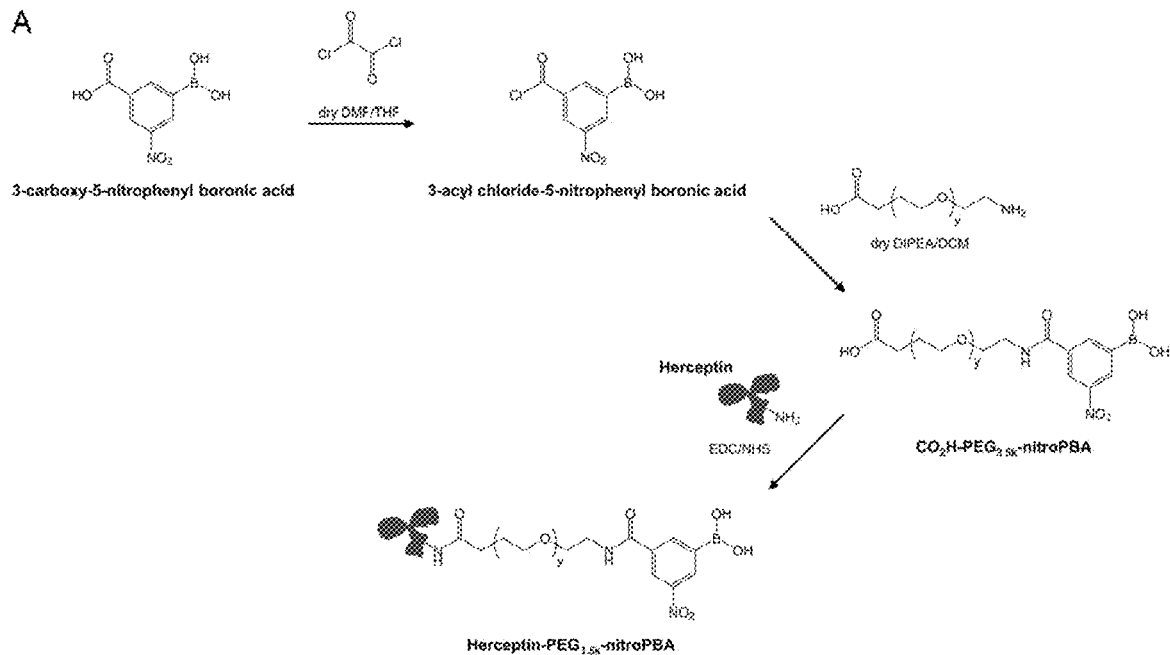
(FIG. 14(A)) Herceptin-PEG3.5k-nitroPBA. y~84 for 3.5 kDa PEG.
Figure 14B:
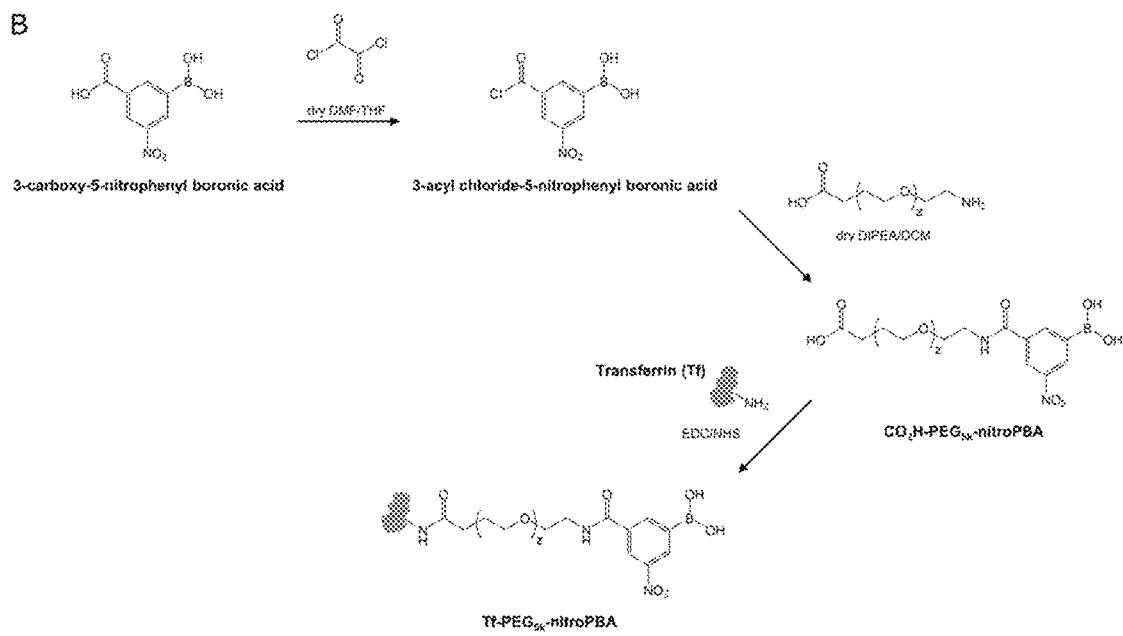
(FIG. 14(B)) Tf-PEG5k-nitroPBA. z~120 for 5 kDa PEG.

Conjugates of 3-carboxy-5-nitrophenyl boronic acid (nitroPBA)-Herceptin and Tf were synthesized by adding nitroPBA to 3.5-kDa polyethylene glycol (PEG), followed by conjugation of the polymer to Herceptin using EDC/NHS chemistry (FIG. 14(A)). A Tf-containing analog was prepared using 5-kDa PEG (FIG. 14(B)). The nitro-PBA boronic acid derivative was chosen because of its high binding constant and low pKa (ca. 6.8) values with MAP. As a result, the nitroPBA conjugates formed stable boronic acid esters with the nanoparticle in circulation, but quickly dissociated from the nanoparticle at pH<6.8 to provide ligand detachment during transcytosis.

Figure 4A:
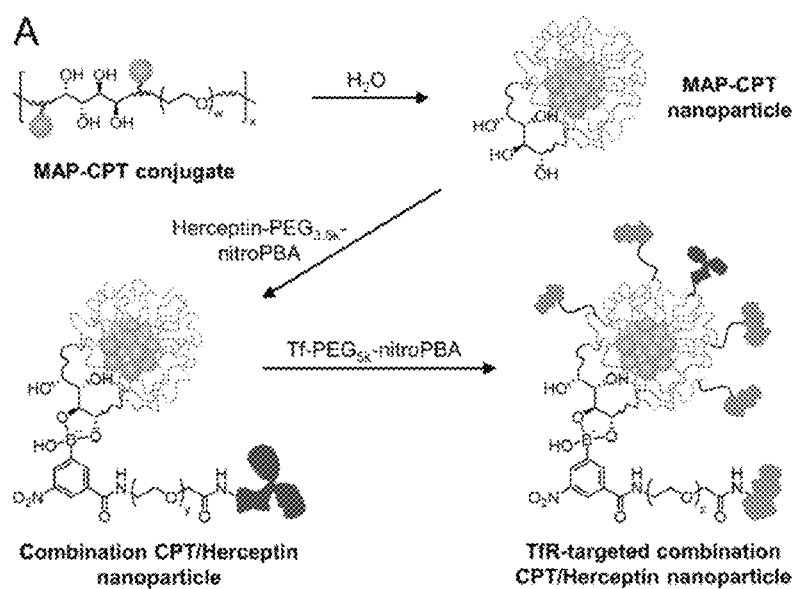
FIG. 4(A-C). Single-agent or combination drug and antibody nanoparticle delivery systems. Preparation of TfR-targeted combination CPT/Herceptin nanoparticle (FIG. 4(A)), TfR-targeted CPT nanoparticle (FIG. 4(B)) and TfR-targeted Herceptin nanoparticle (FIG. 4(C)) formulations. w~82 for 3.4 kDa PEG; x~20 for material used in this study; y~84 for 3.5 kDa PEG; z~120 for 5 kDa PEG.
Figure 4B:
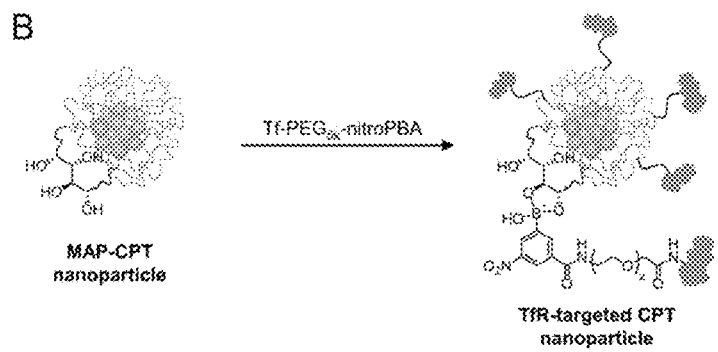
Figure 4C:
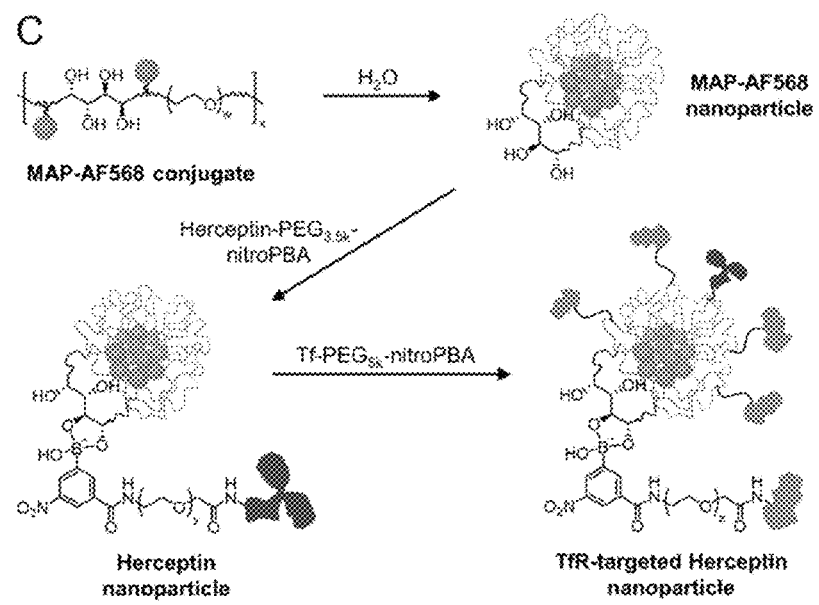
Figure 15:
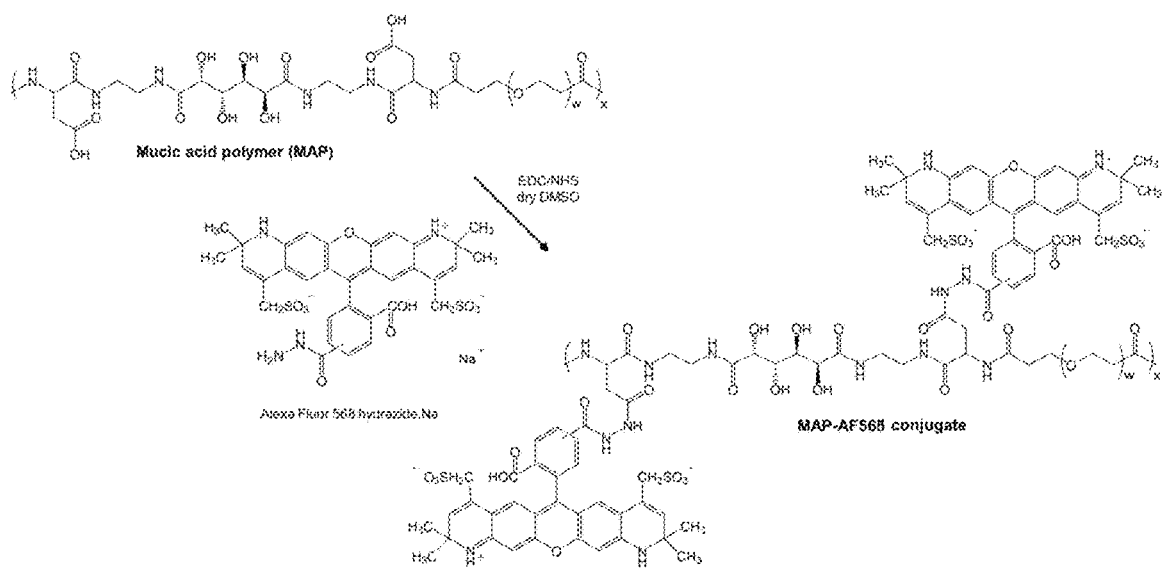
FIG. 15 shows schemes for synthesis of MAP-AF568 polymer conjugate. w~82 for 3.4 kDa PEG; x~20 for material used in Examples.

To assemble TfR-targeted combination CPT/Herceptin nanoparticles, Herceptin-PEG3.5k-nitroPBA conjugate was added to the MAP-CPT nanoparticles at a 1:1 molar ratio, followed by Tf-PEG5k-nitroPBA at a 20 molar excess in PBS, pH 7.4 (FIG. 4(A)). To compare the antitumor activity of nanoparticles containing only CPT, Tf-PEG5k-nitroPBA was directly added to the MAP-CPT nanoparticles at 20 molar excess (FIG. 2B). A Herceptin only nanoparticle control was prepared by conjugating a hydrophobic fluorophore (Alexa Fluor 568, AF568) lacking antitumor activity to the MAP polymer to promote the formation of nanoparticles upon dialysis in water (FIG. 15). Herceptin-PEG3.5k-nitroPBA and Tf-PEG5k-nitroPBA conjugates were added as above to the MAP-AF568 nanoparticles at 1:1 and 20:1 molar ratios, respectively, to form TfR-targeted Herceptin nanoparticles (FIG. 4(C)). Nanoparticles containing Herceptin were purposefully formulated with an average of one antibody per nanoparticle. Numerous antibodies can be added to the nanoparticles. However, adding just one allowed us to test the "worst-case scenario" for delivering an antibody to the brain. If brain delivery and antitumor activity was observed, it was likely that even better efficacy would be achievable with nanoparticles containing multiple antibodies.

Nanoparticle diameter and zeta potential measurements were performed on the above formulations to verify that the nanoparticles had properties appropriate for transcytosis from systemic administrations as well as diffusion through brain tissue, namely a sub-100-nm diameter and negative-near-neutral zeta potential. All three nanoparticle formulations had diameters between 30-40 nm, as measured by dynamic light scattering, and negative-near-neutral zeta potentials when measured in pH7.4 buffer (Tables 6(A-B)).

TABLE 6A

Nanoparticle formulations and characteristics

| Formulation | Nanoparticle diameter, pH 7.4, nm | Zeta potential, pH 7.4, mV |
|---|---|---|
| TfR-targeted CPT nanoparticle | 31.6 ± 1.3 | −1.07 ± 0.48 |
| TfR-targeted Herceptin nanoparticle | 34.1 ± 1.9 | −0.38 ± 0.75 |
| TfR-targeted combination CPT/Herceptin nanoparticle | 29.8 ± 1.6 | −1.22 ± 0.64 |

Data shown for hydrodynamic diameter and zeta potential are the average of 5 measurements ±1 SD.

TABLE 6B

Nanoparticle formulations and characteristics.

| Formulation | Nanoparticle diameter, pH 7.4, nm | Zeta potential, pH 7.4, mV | Nanoparticle diameter, pH 5.5, nm | Zeta potential, pH 5.5, mV |
|---|---|---|---|---|
| MAP-CPT nanoparticle | 37.8 ± 1.4 | −0.39 ± 0.78 | 38.2 ± 1.8 | −0.27 ± 0.84 |
| TfR-targeted MAP-CPT nanoparticle | 29.4 ± 1.2 | −1.32 ± 0.45 | 37.9 ± 1.3 | −0.51 ± 0.42 |
| Non-targeted MAP-CPT nanoparticle | 45.6 ± 1.7 | −0.57 ± 0.88 | 37.6 ± 1.9 | −0.43 ± 0.68 |

Data shown for hydrodynamic diameter and zeta potential are the average of 5 measurements ±1 SD.

The breast cancer brain metastasis model was established by intracardiac (ICD) injection of HER2-positive BT474-Gluc cells into Rag2−/−; Il2rg−/− mice. The present inventors have previously shown that the method used to form brain tumors in mice can dramatically affect the efficacy of therapeutics and their brain penetration. A marked antitumor response and brain accumulation of free CPT, a non-BBB-penetrant small molecule, and a non-targeted nanoparticle containing CPT in tumors that were established by stereotaxic intracranial injection was observed. In contrast, treatment with the nanoparticles lacking Tf to enable transcytosis gave no antitumor response in both the ICD model and a third model involving intravenous injection of the cancer cells that more closely replicated the metastasis process in patients was used. The ICD model, however, did allow CPT to penetrate and have a small antitumor effect while our new model did not. Here, the ICD model was chosen because it appeared to have an impermeable BBB/BTB to larger nanoparticle entities, and would allow comparison to other studies that have employed this method of creating brain metastases.

Figure 16:
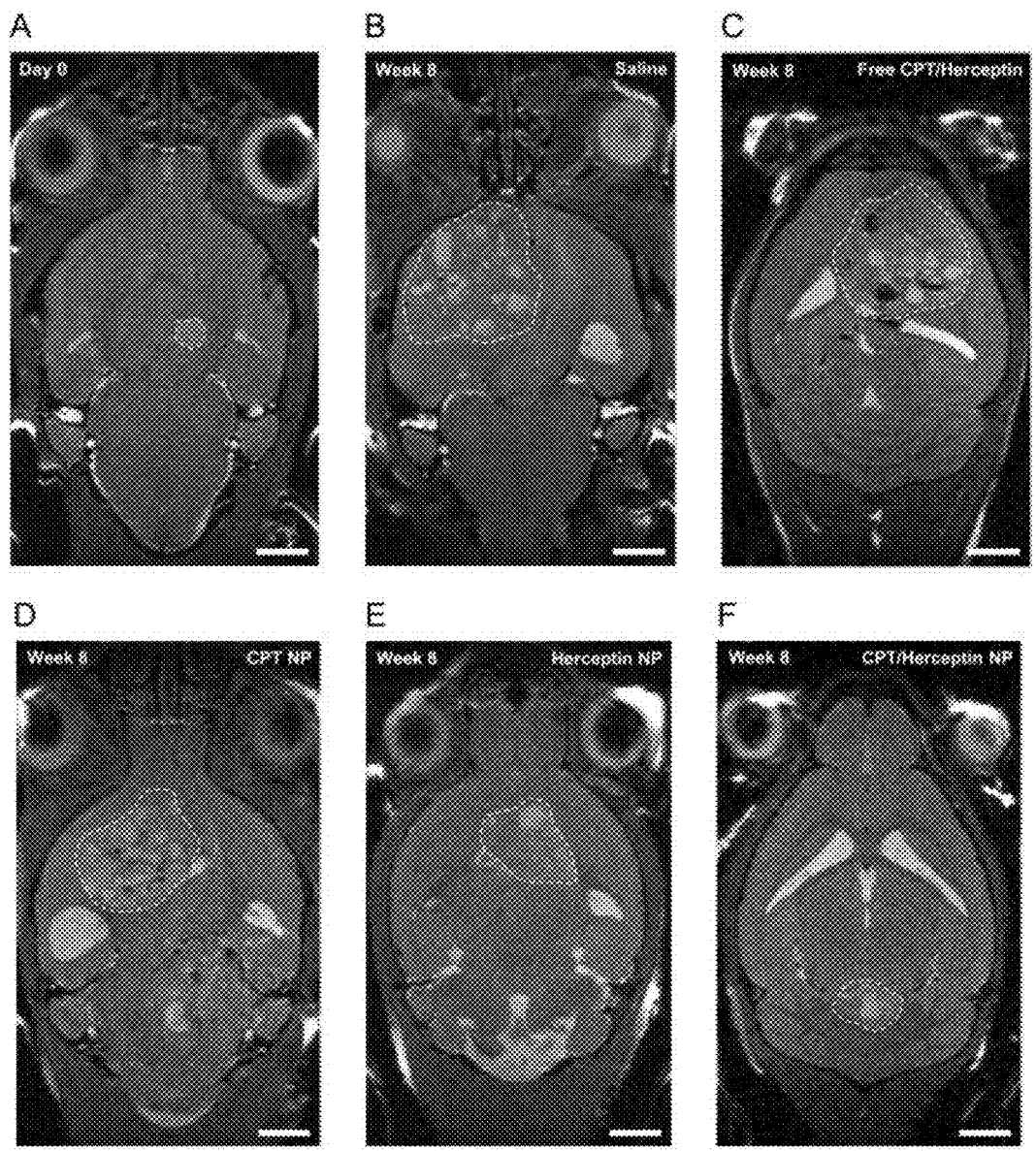
FIG. 16 shows representative MRI images of metastatic brain tumors at the start of treatment (A), and 8 weeks after the start of treatment with saline (B), free CPT and Herceptin (C), TfR-targeted CPT nanoparticles (D), TfR-targeted Herceptin nanoparticles (E) and TfR-targeted combination CPT/Herceptin nanoparticles (F). Dotted lines denote tumor margins. Formulations were systemically administered weekly for 4 weeks at a dose of 4 and/or 24 mg/kg (CPT and/or Herceptin bases, respectively). Scale bar, 2 mm; NP, nanoparticle.
Figure 17:
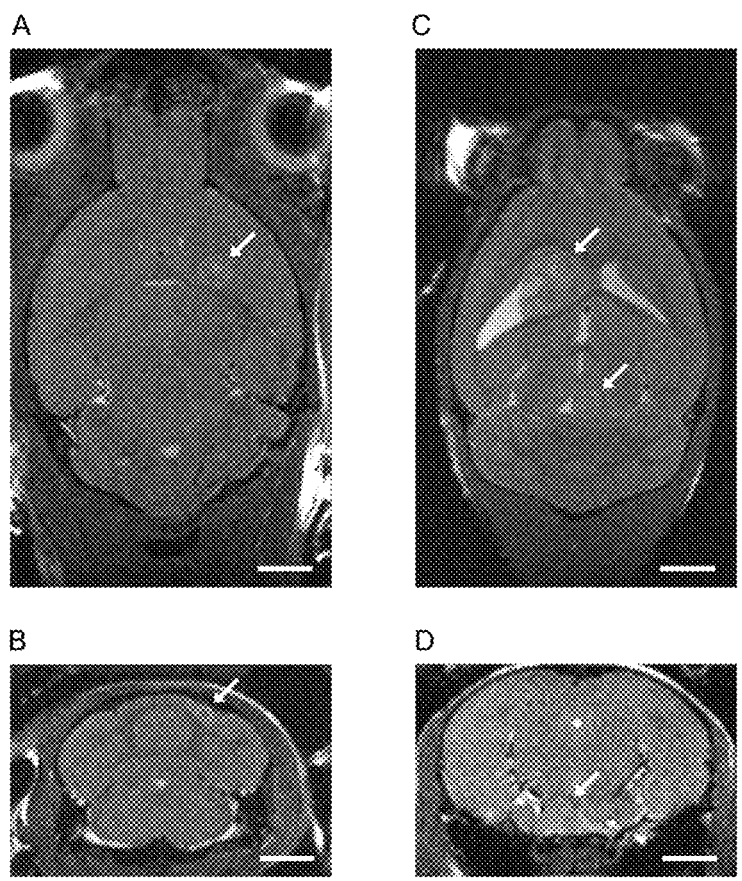
FIG. 17 shows images of metastatic brain tumors imaged by MRI following IV injection of BT474-Gluc cells. Intracerebral (A, B, C) and leptomeningeal metastases were detected (D). Most intracerebral metastases were in the cerebrum (A), with occasional metastases in the cerebellum (B). Multifocal metastases were occasionally observed (C). Leptomeningeal metastases most commonly grew in the subarachnoid space (D). Scale bar, 2 mm.

To assess how the incorporation of the therapeutic antibody affected the efficacy of the targeted nanoparticles, the antitumor activity of TfR-targeted combination CPT/Herceptin nanoparticles compared to TfR-targeted CPT nanoparticles, TfR-targeted Herceptin nanoparticles and combined free CPT and Herceptin in the ICD model were investigated. A saline treatment group was used as the control. Treatment was initiated when tumors reached 2 mm³ in volume. FIGS. 16 and 17 shows a representative MRI image of the metastatic tumors at the start of treatment. The different formulations were systemically administered weekly for 4 weeks at a dose of 4 and/or 24 mg/kg (CPT and/or Herceptin bases, respectively), and tumor volume was measured weekly by MRI for 8 weeks.

Figure 18:
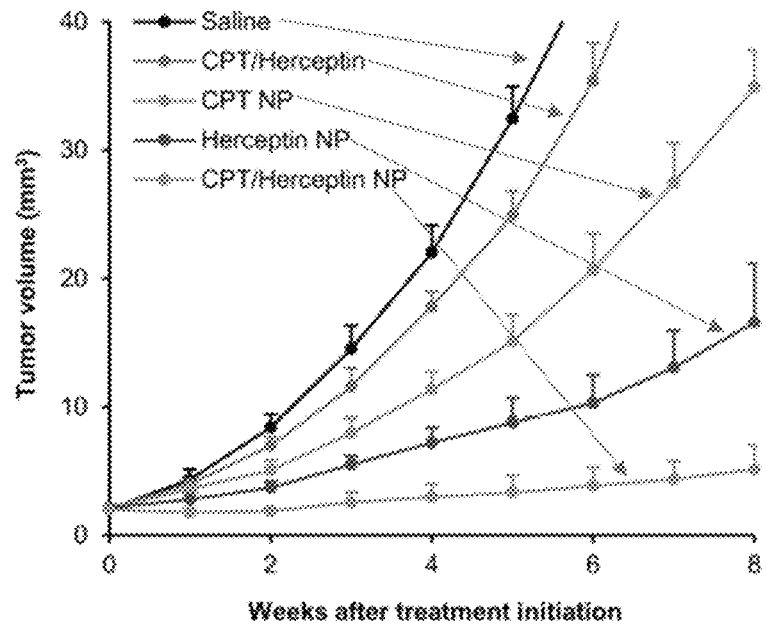
FIG. 18. Combined nanoparticle delivery of CPT and Herceptin inhibits brain metastatic tumor growth more effectively than nanoparticle delivery of either monotherapy and combined free drug. Tumor growth curves of BT474-Gluc metastatic brain tumors treated with free CPT and Herceptin (gray, 4 and 24 mg/kg, respectively), TfR-targeted CPT nanoparticles (orange, 4 mg CPT/kg), TfR-targeted Herceptin nanoparticles (purple, 24 mg Herceptin/kg) and TfR-targeted combination CPT/Herceptin nanoparticles (blue, 4 mg CPT/kg and 24 mg Herceptin/kg) compared to saline (black). Data shown are the average of 6 mice per treatment group. Error bars indicate SE.
Figure 19:
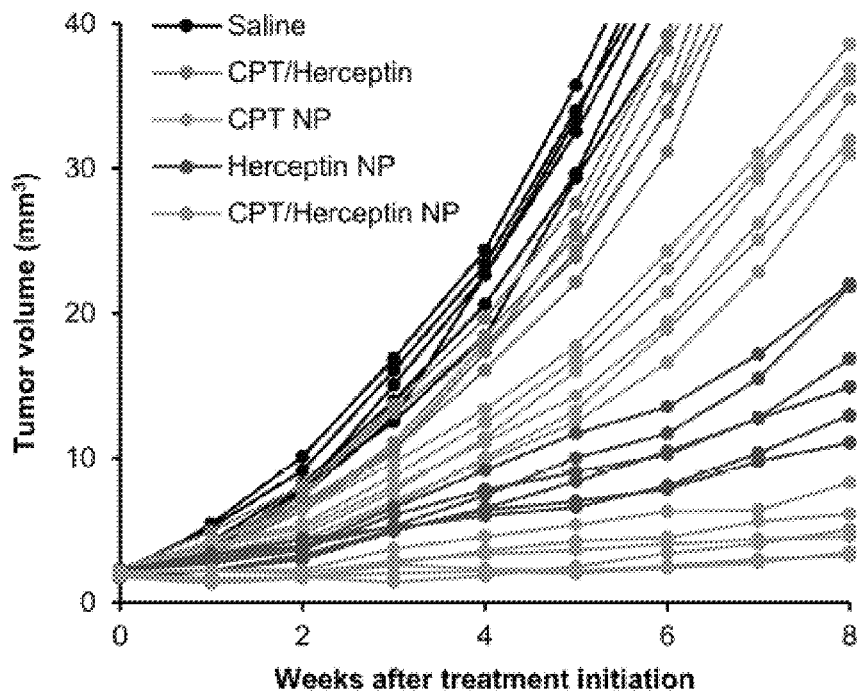
FIG. 19 shows individual tumor growth curves of BT474-Gluc metastatic brain tumors treated with CPT and Herceptin (gray, 4 and 24 mg/kg, respectively), TfR-targeted CPT nanoparticles (orange, 4 mg CPT/kg), TfR-targeted Herceptin nanoparticles (purple, 24 mg Herceptin/kg) and TfR-targeted combination CPT/Herceptin nanoparticles (blue, 4 mg CPT/kg and 24 mg Herceptin/kg) compared to saline (black). NP, nanoparticle.

FIG. 18 and Table 7 show the results from treating mice bearing brain tumors with the formulations described above. Data from individual animals are provided in FIG. 19. For the physical mixture of CPT and Herceptin, the tumor growth delay is not significantly different than previously observed for CPT alone.27 These results suggest that Herceptin is not penetrating the BBB/BTB to an extent to produce any antitumor activity, and are consistent with data published for Herceptin alone.

TABLE 7

Antitumor efficacy in Rag2−/−; Il2rg−/− mice bearing human BT474-Gluc breast cancer metastatic brain tumors.

| | Mean tumor volume (mm³) | Median tumor volume (mm³) | P vs. saline |
|---|---|---|---|
| Saline | 89 | 89 | — |
| CPT and Herceptin (4 and 24 mg/kg, respectively) | 72 | 74 | 0.0087 |
| TfR-targeted CPT nanoparticle (4 mg CPT/kg) | 35 | 35 | 0.0022 |
| TfR-targeted Herceptin nanoparticle (24 mg Herceptin/kg) | 17 | 16 | 0.0022 |
| TfR-targeted combination CPT/Herceptin nanoparticle (4 mg CPT/kg and 24 mg Herceptin/kg) | 5 | 5 | 0.0022 |

Data provided are mean and median tumor volumes at the end of the study. P values were calculated using the Wilcoxon-Mann-Whitney test.

The tumor growth delay from treatment with TfR-targeted CPT nanoparticles was as observed previously and showed the excellent reproducibility of both the model and the nanoparticle synthesis. Compared to previous data demonstrating no tumor growth delay with nanoparticles lacking Tf, these results suggested that the antitumor effects observed for this treatment are facilitated by targeted nanoparticle delivery of CPT alone.

TfR-targeted Herceptin nanoparticles gave a greater antitumor response than those containing CPT, suggesting that the nanoparticles can deliver functional antibodies into the brain via transcytosis. Itis also encouraging that significant antitumor activity can be achieved when only one antibody is on each nanoparticle. Future studies will explore variable amounts of antibody contents.

When both Herceptin and CPT are combined in a TfR-targeted nanoparticle, the best antitumor response was observed (compared to the data from Herceptin alone or CPT alone), and the antitumor effects appeared to bequite durable. Notably, the type of formulation for the combination (free drug vs. nanoparticle) greatly affected the outcome of the brain metastases, as shown in FIG. 18. MRI images further illustrate the differences between the tumors after treatment with the above formulations (FIG. 16). These results suggested that both the CPT and Herceptin are delivered to the brain via transcytosis of the nanoparticle and indicate that combination therapies will be possible with this type of delivery system.

In summary, TfR-targeted nanoparticles containing either the antibody Herceptin alone or in combination with the small molecule drug CPT were shown to deliver their payloads to intracranial breast cancer tumors to provide significant antitumor activity. These results not only show that functional antibodies can be delivered to the brain, but also that they can be used in combination with other drugs to provide enhanced antitumor activity. This initial study was performed with a single dose amount and a single dosing schedule. The dosing amount used here is well below what is possible with the nanoparticles and was selected in order to have proper comparison to free CPT administered near the maximum tolerated dose. Therefore, further studies with increasing dosing amounts and alternative dosing schedules are merited. Importantly, these results demonstrate the ability to deliver therapeutic combinations to treat brain metastases as well as other brain diseases.

The following references provide additional information useful for understanding the principles and issues associated with the present disclosure, and are incorporated by reference herein for all purposes, or at least for their discussions concerning issues directed to allowing for passage of pharmaceuticals and other pharmaceutically active materials across the BBB.

1. Cairncross, J. G., Kim, J. H., and Posner, J. B. (1980) Radiation therapy for brain metastases. *Ann. Neurol.* 7, 529-541.
2. Barnholtz-Sloan, J. S., Sloan, A. E., Davis, F. G., Vigneau, F. D., Lai, P., and Sawaya R. E. (2004) Incidence proportions of brain metastases in patients diagnosed (1973 to 2001) in the Metropolitan Detroit Cancer Surveillance System. *J. Cin. Oncol.* 22, 2865-2872.
3. Crivellari, D., Pagani, O., Veronesi, A., Lombardi, D., Nole, F., Thurlimann, B., Hess, D., Borner, M., Bauer, J., Martinelli, G., et al. (2001) High incidence of central nervous system involvement in patients with metastatic or locally advanced breast cancer treated with epirubicin and docetaxel. *Ann. Oncol.* 12, 353-356.
4. Lin, N. U., Amiri-Kordestani, L., Palmieri, D., Liewehr, D. J., and Steeg, P. S. (2013) CNS metastases in breast cancer: old challenge, new frontiers. *Cin. Cancer Res.* 19, 6404-6418.
5. Kennecke, H., Yerushalmi, R., Woods, R., Cheang, M. C., Voduc, D., Speers, C. H., Nielsen, T. O., and Gelmon, K. (2010) Metastatic behavior of breast cancer subtypes. *J. Cin. Oncol.* 28, 3271-3277.
6. Rostami, R., Mittal, S., Rostami, P., Tavassoli, F., and Jabbari B. (2016) Brain metastasis in breast cancer: a comprehensive literature review. *J. Neurooncol.* 127, 407-414.
7. Lin, N. U., and Winer, E. P. (2007) Brain metastases: the HER2 paradigm. *Cin. Cancer Res.* 13, 1648-1655.
8. Aversa, C., Rossi, V., Geuna, E., Martinello, R., Milani, A., Redana, S., Valabrega, G., Aglietta, M., and Montemurro, F. (2014) Metastatic breast cancer sybtypes and central nervous system metastases. *Breast* 23, 623-628.
9. Taskar, K. S., Rudraraju, V., Mittapali, R. K., Samala, R., Throsheim, H. R., Lockman, J., Gril, B., Hua, E., Palmieri, D., Polli, J. W., et al. (2012) Lapatinib distribution in HER2 overexpressing experimental brain metastases of breast cancer. *Pharm. Res.* 29, 770-781.
10. Morikawa, A., Peereboom, D. M., Thorsheim, H. R., Samala, R., Baylan, R., Murphy, C. G., Lockman, P. R., Simmons, A., Weil, R. J., Tabar, V., et al. (2015) Capecitabine and lapatinib uptake in surgically resected brain metastases from metastatic breast cancer patients: a prospective study. *Neuro. Oncol.* 17, 289-295.
11. Bohn, K. A., Adkins, C. E., Mittapali, R. K., Terrell-Hall, T. B., Mohammad, A. S., Shah, N., Dolan, E. L., Nounou, M. I., and Lockman, P. R. (2016) Semi-automated rapid quantification of brain vessel density using fluorescent microscopy. *J. Neurosci. Methods* 270, 124-131.
12. Oehrlich, N. E., Spineli, L. M., Papendorf, F., and Park-Simon, T. W. (2017) Clinical outcome of brain metastases differs significantly among breast cancer subtypes. *Oncol Lett.* 14, 194-200.
13. Shah, N., Mohammad, A. S., Saralkar, P., Sprowls, S. A., Vickers, S. D., John, D., Tallman, R. M., Lucke-Wold, B. P., Jarrell, K. E., Pinti, M., et al. (2018) Investigational chemotherapy and novel pharmacokinetic mechanisms for the treatment of breast cancer brain metastases. *Pharmacol. Res.* 132, 47-68.
14. Ramakrishna, N., Temin, S., Chandarlapaty, S., Crews, J. R., Davidson, N. E., Esteva, F. J., Giordano, S. H., Gonzalez-Angulo, A. M., Kirshner, J. J., Krop, I., et al. (2014) Recommendations on disease management for patients with advanced human epidermal growth factor receptor 2-positive breast cancer and brain metastases: American Society of Clinical Oncology clinical practice guideline. *J. Clin. Oncol.* 32, 2100-2108.
15. Pardridge, W. M. (2005) The blood-brain barrier: Bottleneck in brain drug development. *NeuroRx* 2, 3-14.
16. Lockman, P. R., Mittapalli, R. K., Taskar, K. S., Rudraraju, V., Gril, B., Bohn, K. A., Adkins, C. E., Roberts, A., Thorsheim, H. R., Gaasch, J. A., et al. (2010) Heterogeneous blood-tumor barrier permeability determines drug efficacy in experimental brain metastases of breast cancer. *Clin. Cancer Res.* 16, 5664-5678.
17. Mittapalli, R. K., Adkins, C. E., Bohn, K. A., Mohammad, A. S., Lockman, J. A., and Lockman, P. R. (2017) Quantitative fluorescence microscopy measures vascular pore size in primary and metastatic brain tumors. *Cancer Res.* 77, 238-246.
18. Osswald, M., Blaes, J., Liao, Y., Solecki, G., Gommel, M., Berghoff, A. S., Salphati, L., Wallin, J. J., Phillips, H. S., Wick, W., et al. (2016) Impact of blood-brain barrier integrity on tumor growth and therapy response in brain metastases. *Clin. Cancer Res.* 22, 6078-6087.
19. Mehta, A. I., Brufsky, A. M., and Sampson, J. H. (2013) Therapeutic approaches for HER2-positive brain metastases: circumventing the blood-brain barrier. *Cancer Treat. Rev.* 39, 261-269.
20. Mittapalli, R. K., Liu, X., Adkins, C. E., Nounou, M. I., Bohn, K. A., Terrell, T. B., Qhattal, H. S., Geldenhuys, W. J., Palmieri, D., Steeg, P. S., et al. (2013) Paclitaxel-hyaluronic nanoconjugates prolong overall survival in a preclinical brain metastases of breast cancer model. *Mol. Cancer Ther.* 12, 2389-2399.
21. Adkins, C. E., Nounou, M. I., Hye, T., Mohammad, A. S., Terrell-Hall, T., Mohan, N. K., Eldon, M. A., Hoch, U., and Lockman, P. R. (2015) NKTR-102 efficacy versus irinotecan in a mouse model of brain metastases of breast cancer. *BMC Cancer* 15, 685.
22. Mohammad, A. S., Griffith, J. I., Adkins, C. E., Shah, N., Sechrest, E., Dolan, E. L., Terrell-Hall, T. B., Hendriks, B. S., Lee, H., and Lockman, P. R. (2018) Liposomal irinotecan accumulates in metastatic lesions, crosses the blood-tumor barrier (BTB), and prolongs survival in an experimental model of brain metastases of triple negative breast cancer. *Pharm. Res.* 35.
23. Pardridge, W. M. (2007) Drug targeting to the brain. *Pharm. Res.* 24, 1733-1744.
24. Chen, Y., and Liu, L. (2012) Modern methods for delivery of drugs across the bloodbrain barrier. *Adv. Drug Deliv. Rev.* 64, 640-665.
25. Pardridge, W. M. (2017) Delivery of biologics across the blood-brain barrier with molecular trojan horse technology. *BioDrugs* 31, 503-519.
26. Uchida, Y., Ohtsuki, S., Katsukura, Y., Ikeda, C., Suzuki, T., Kamiie, J., and Terasaki T. (2011) Quantitative targeted absolute proteomics of human blood-brain barrier transporters and receptors. *J. Neurochem.* 117, 333-345.
27. Wyatt, E. A., and Davis, M. E. (2018) Method of establishing breast cancer brain metastases affects brain uptake and efficacy of targeted, therapeutic nanoparticles. *Bioeng. Tranls. Med doi:* 10.1002/btm2.10108.

28. Clark, A. J., and Davis, M. E. (2015) Increased brain uptake of targeted nanoparticles by adding an acid-cleavable linkage between transferrin and the nanoparticle core. *Proc. Natl. Acad Sci.* USA 112, 12486-12491.

29. Han, H., and Davis, M. E. (2013) Targeted nanoparticles assembled via complexation of boronic-acid-containing targeting moieties to diol-containing polymers. *Bioconjug. Chem.* 24, 669-677.

30. Wiley, D. T., Webster, P., Gale, A., and Davis, M. E. (2010) Transcytosis and brain uptake of transferrin-containing nanoparticles by tuning avidity to transferrin receptor. *Proc. Natl. Acad Sci.* USA 110, 8662-8667.

31. Nance, E. A., Woodworth, G. F., Sailor, K. A., Shih, T. Y., Xu, Q., Swaminathan, G., Xiang, D., Eberhart, C., and Hanes, J. (2012) A dense poly(ethylene glycol) coating improves penetration of large polymeric nanoparticles within brain tissue. *Sci. Transl. Med* 4, 149ra119.

32. Terrell-Hall, T. B., Nounou, M. I., El-Amrawy, F., Griffith, J. I. G., and Lockman, P. R. (2017) Trastuzumab distribution in an in-vivo and in-vitro model of brain metastases of breast cancer. *Oncotarget* 8, 83734-83744.

All references cited within this specification are incorporated by reference in their entireties for all purposes, or at least for their teachings in the context of their recitation.

What is claimed:

1. A method for slowing growth of a brain tumor by 82%-94%, the method comprising systemically administering, to a subject having the brain tumor, a nanoparticle comprising:
    (a) a nanoparticle core comprising a mucic acid-containing polymer;
    (b) transferrin joined to the nanoparticle core by a nitrophenyl boronic ester linkage to vicinal diols of the mucic acid-containing polymer;
    (c) trastuzumab; and
    (d) camptothecin.

2. The method of claim 1, wherein the brain tumor is metastasized from a HER2-positive breast cancer.

3. The method of claim 1, wherein the subject is a human.

4. The method of claim 1, wherein the nanoparticle core comprises a polymer containing units having the structure:

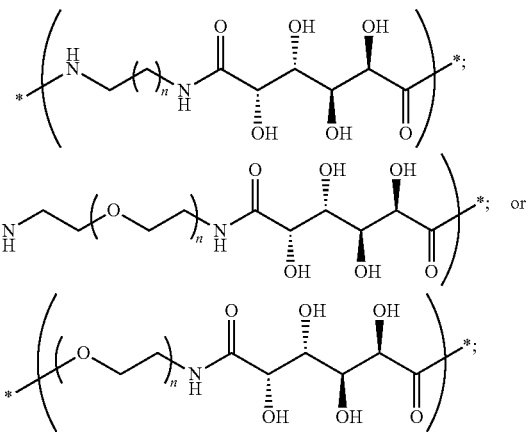

wherein n is from 1-20.

5. The method of claim 1, wherein the nanoparticle core comprises the structure:

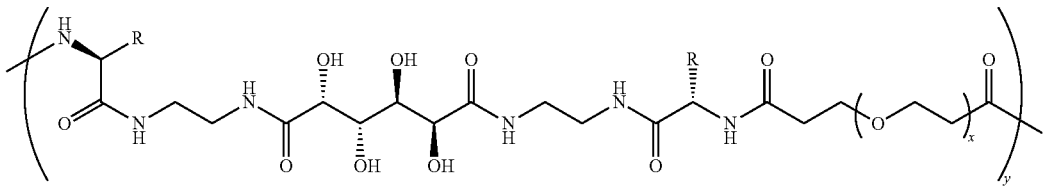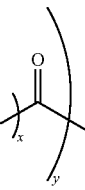

wherein:
x is from 15-100;
y is from 10-25; and
R is an amino acid, or salt thereof, coupled to one or more of transferrin, trastuzumab and/or camptothecin.

6. The method of claim 1, wherein the nanoparticle core comprises a polymer containing units having the structure:

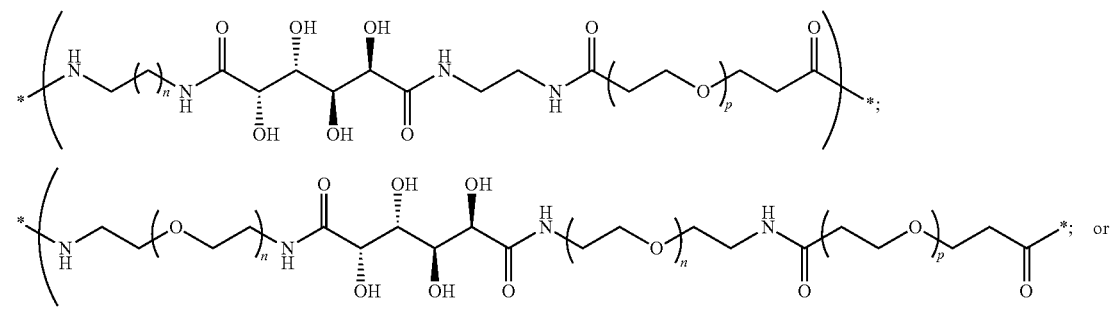

-continued

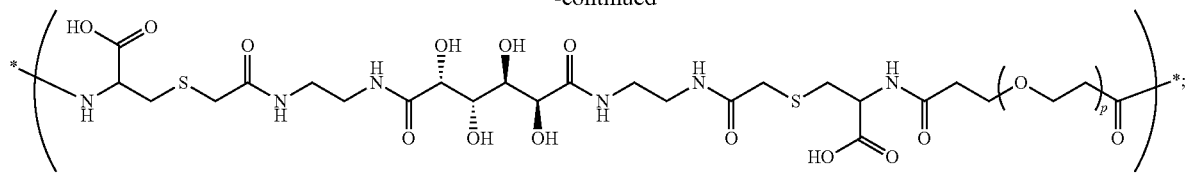

wherein:
n is from 1-20; and
p is from 20-200.

7. The method of claim 1, wherein the structure of (b) is:

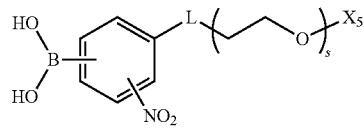

wherein:
s is from 2-2,000;
L is an amide, a carbonate, an ester or a disulfide group; and
$X_5$ is $C_{1-6}$ alkyl, optionally substituted with —OH, —COOH, —B(OH)$_2$, —C(=O)—O—alkyl, C(=O)—O-aryl, —NH$_2$, —NH(alkyl), —N(alkyl)$_2$ or —SH; with transferrin coupled thereto.

8. The method of claim 1, wherein the camptothecin is joined to the nanoparticle core by an amino acid.

9. The method of claim 1, wherein the nanoparticle comprises a unit structure:

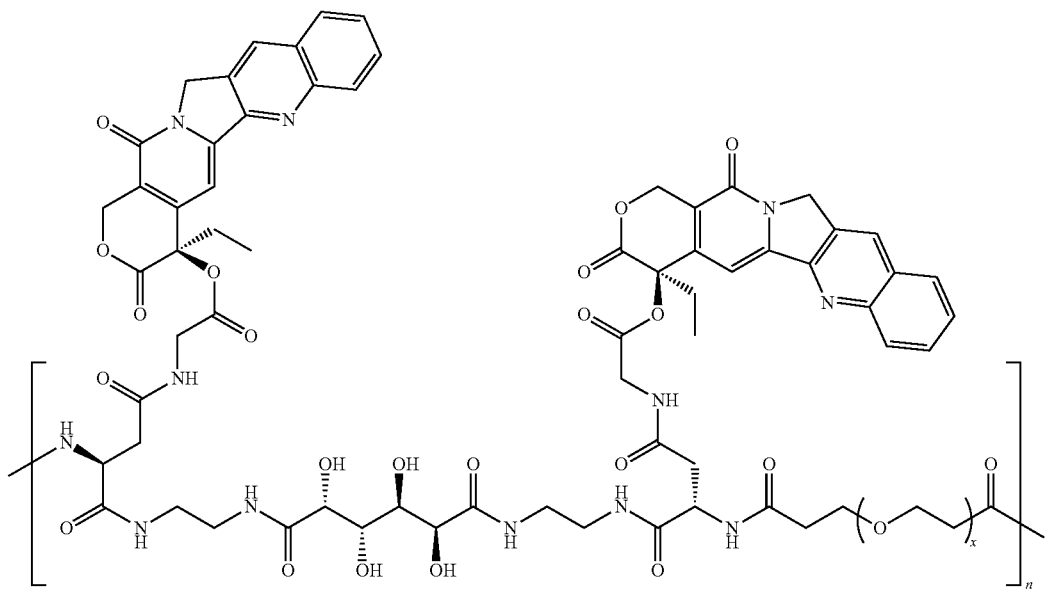

wherein:
x is from 15-100; and
n is from 1-20.

* * * * *